(12) United States Patent
Lipka et al.

(10) Patent No.: US 12,397,058 B2
(45) Date of Patent: Aug. 26, 2025

(54) METABOLICALLY STABLE PRODRUGS

(71) Applicants: TSRL, Inc., Ann Arbor, MI (US); Regents of the University of Michigan, Ann Arbor, MI (US)

(72) Inventors: Elke Lipka, Ann Arbor, MI (US); Eric Simon, Chelsea, MI (US); Andy D. White, Pinckney, MI (US); Kim M. Hutchings, Dexter, MI (US); Xinmin Gan, Ann Arbor, MI (US)

(73) Assignees: TSRL, Inc., Ann Arbor, MI (US); Regents of the University of Michigan, Ann Arbor, MI (US)

( * ) Notice: Subject to any disclaimer, the term of this patent is extended or adjusted under 35 U.S.C. 154(b) by 494 days.

(21) Appl. No.: 17/254,517

(22) PCT Filed: Jun. 26, 2019

(86) PCT No.: PCT/US2019/039198
§ 371 (c)(1),
(2) Date: Dec. 21, 2020

(87) PCT Pub. No.: WO2020/006050
PCT Pub. Date: Jan. 2, 2020

(65) Prior Publication Data
US 2021/0401992 A1    Dec. 30, 2021

Related U.S. Application Data

(60) Provisional application No. 62/689,887, filed on Jun. 26, 2018.

(51) Int. Cl.
| | | |
|---|---|---|
| *A61K 9/00* | (2006.01) | |
| *A61K 47/54* | (2017.01) | |
| *A61P 31/20* | (2006.01) | |
| *C07F 9/40* | (2006.01) | |
| *C07F 9/6512* | (2006.01) | |
| *C07F 9/655* | (2006.01) | |
| *C07F 9/6558* | (2006.01) | |
| *C07F 9/6574* | (2006.01) | |

(52) U.S. Cl.
CPC .......... *A61K 47/545* (2017.08); *A61K 9/0053* (2013.01); *A61P 31/20* (2018.01); *C07F 9/4065* (2013.01); *C07F 9/6512* (2013.01); *C07F 9/6551* (2013.01); *C07F 9/65586* (2013.01); *C07F 9/65742* (2013.01)

(58) Field of Classification Search
CPC .... C07F 9/4065; C07F 9/6512; C07F 9/6551; C07F 9/65586; C07F 9/65742; C07F 9/65583; C07F 9/6561; C07F 9/65616
See application file for complete search history.

(56) References Cited

U.S. PATENT DOCUMENTS

| | | | |
|---|---|---|---|
| 6,002,029 A | 12/1999 | Hostetler et al. | |
| 6,027,150 A | 2/2000 | Flewitt et al. | |
| 8,569,321 B2 | 10/2013 | Ware et al. | |
| 8,962,829 B1 | 2/2015 | Ware, Jr. et al. | |
| 2006/0111276 A1 | 5/2006 | McKenna et al. | |
| 2007/0003608 A1 | 1/2007 | Almond et al. | |
| 2011/0263535 A1 | 10/2011 | McKenna et al. | |
| 2014/0288025 A1 | 9/2014 | Milne et al. | |

FOREIGN PATENT DOCUMENTS

| | | | | |
|---|---|---|---|---|
| GB | 2208648 A | * | 4/1989 | ........... C07D 211/90 |
| WO | WO1996/15132 A1 | | 5/1996 | |
| WO | 1997/22613 A1 | | 6/1997 | |
| WO | 2004/083155 A2 | | 9/2004 | |
| WO | 2005/080406 A2 | | 9/2005 | |

OTHER PUBLICATIONS

Chemical Abstracts Registry No. 66889-94-9, indexed in the Registry file on STN CAS Online Nov. 16, 1984. (Year: 1984).*
Hall et al., Pharmaceutical Research (1985), 5, pp. 233-238. (Year: 1985).*
PubChem CID 938, National Center for Biotechnology Information. PubChem Compound Summary for CID 938, Nicotinic acid. https://pubchem.ncbi.nlm.nih.gov/compound/Nicotinic-acid. Accessed Jun. 8, 2023, create date Sep. 16, 2004. (Year: 2004).*
Extended European Search Report for European Application No. 19824668.8, Jun. 17, 2022.

(Continued)

*Primary Examiner* — Laura L Stockton
(74) *Attorney, Agent, or Firm* — Weston R. Gould; Dinsmore & Shohl LLP

(57) ABSTRACT

Provided are prodrugs of various therapeutic agents that provide enhanced bioavailability of the therapeutic agent, and methods of treatment conditions in a subject by administration of the one or prodrugs. As provided herein a prodrug includes a therapeutic agent covalently attached to a cap, the cap having a structure according to formula (I) where: $R^1$ is a branched or linear substituted or unsubstituted C2-C6 alkyl, alkenyl, or alkynyl; X is $-S(0)_2-$; $R^2$ is a branched or linear substituted or unsubstituted C4-C20 alkyl, alkenyl, or alkynyl; and $R^3$ is $-H$, C3-C5 cycloalkyl, C3-C5 cycloheteroalkyl, $-C(CH_3)_3$, $-CF_3$, $-C(CF_3)_3$, or a substituted or unsubstituted phenyl.

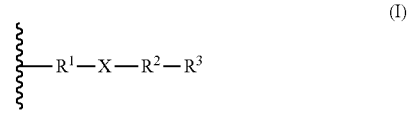

(I)

15 Claims, 4 Drawing Sheets

(56) References Cited

OTHER PUBLICATIONS

Sofia, M. et al., Discovery of a ß-d-2'-deoxy-2'-a-fluoro-2'-ß-C-methyluridine nucleotide prodrug (PSI-7977) for the treatment of hepatitis C virus, J. Med. Chem., 53(19):7202-7218, Oct. 14, 2010.
Ruiz, J. et al., Synthesis, metabolic stability and antiviral evaluation of various alkoxyalkyl esters of cidofovir and 9-(S)-[3-hydroxy-2-(phosphonomethoxy) propyl] adenine, Bioorganic & Medicinal Chemistry, 19(9): 2950-2958, May 1, 2011.

* cited by examiner

METABOLICALLY STABLE PRODRUGS

CROSS-REFERENCE TO RELATED APPLICATIONS

This application is a National Stage Entry under 35 U.S.C. § 371 of International Patent Application No. PCT/US2019/039198, filed Jun. 26, 2019, which depends from and claims priority to U.S. Provisional Application No. 62/689,887 filed Jun. 26, 2018, the entire contents of which are incorporated herein by reference.

TECHNICAL FIELD

The present disclosure generally relates to prodrugs of antiviral agents.

BACKGROUND

It is conventional to couple a substrate moiety to an active drug species such that an enzyme associated with the target site acts on the substrate moiety to generate an active species at a desired locality. This prodrug in vivo activation strategy provides benefits in that the concentration of an active compound at the local site of enzymatic cleavage may be increased. Additionally, the moiety of the prodrug provides limited exposure to the active compound, which reduces side effects. Enzymes useful in prodrug activation have been described and include enzymes such as thymidine kinase, cytosine deaminase, and purine nucleoside phosphorylase, as described in U.S. Pat. Nos. 5,338,678; 5,552,311; 6,017,896; and 6,027,150. While the basic concept of coupling a substrate moiety to an active species is known, this approach has met with limited therapeutic success owing to difficulty in transporting the prodrug into a particular type of cell, and the presence of a cleavage enzyme in cell types other than those targeted for therapeutic interaction with the active drug species.

Some active drug species utilized in the treatment of viral diseases are highly polar and charged causing the drug to be strongly hydrophilic. Hydrophilic drugs often have a low ability to transport across the lipid-bilayer of cellular membranes, thereby causing low bioavailability forcing the drug to be delivered intravenously. The high polarity also limits the amount of the antiviral agent that can penetrate the infected cell. To overcome low bioavailability and to increase the cellular concentration at the active drug site, the drug can be altered synthetically to increase its lipophilicity. A lipophilic prodrug designed to be released in the infected cells would make the polar antiviral agent more lipophilic to improve oral bioavailability and transport into cells. As examples, foscarnet and cidofovir are two highly polar antiviral agents that could benefit from a lipophilic prodrug strategy.

Foscarnet (phosphonoformic acid, PFA) is a potent inhibitor of herpesvirus, influenza, and retroviral polymerases and has antiviral activity efficacy in human infections caused by herpes simplex virus (HSV1 and HSV2) cytomegalovirus (CMV) and human immunodeficiency virus type 1 (HIV1).

Cidofovir (HPMPC) is known for its broad-spectrum activity against all DNA viruses. It has been shown to have therapeutic potential not only against cytomegalovirus including acyclovir resistant virus, but also against other herpes viruses such as herpes simplex virus 1 and 2, varicella zoster virus, Epstein Barr virus, as well as herpes viruses 6, 7, and 8. Cidofovir also has antiviral activity against adenoviruses, papovaviruses such as papillomavirus and polyomavirus, pox viruses (including small pox), and hepadnaviruses such hepatitis B.

The 2'-F, 2'-C-Methyluridine-5'monophosphate is highly active against single strand RNA viruses, especially those in the Flaviviridea family that cause human diseases such as Hepatitis C, Dengue fever, West Nile encephalitis and Zika fever among others. This compound targets the viral RNA dependent RNA polymerase being recognized as a natural substrate that induces a chain termination of the RNA and an inhibition of viral replication. Once in a cell the monophosphate is converted to the triphosphate the compound can stay in the cell for up to 38 hours. The monophosphate, however, cannot readily enter the cell necessitating a prodrug strategy. Some prodrugs have been developed (Sofia, et al., *J. Med. Chem.*, 2010; 53:7202-7218) that deliver the drug specifically and completely to the liver for treating Hepatitis C infection. Prodrugs with a wider tissue distribution, however, are still needed to treat other diseases.

Foscarnet and cidofovir have been used successfully to treat CMV retinitis, and in particular are useful for acyclovir and ganciclovir-resistant herpes simplex viruses, but several limitations prevent their practical use as general antiretroviral agents. These include the lack of orally bioavailable formulations necessitating intravenous administration and with certain toxicities. These limitations for cidofovir and foscarnet are due in part to their polarity and anionic nature at physiological pH. These physicochemical properties also impede intracellular uptake of cidofovir and foscarnet. The low intracellular uptake warrants higher therapeutic doses, which contributes to an increase in toxicity. As a result, both cidofovir and foscarnet have adverse effects including renal impairment, serum electrolyte and hemoglobin disturbances, seizures, and local genital irritation/ulceration.

Many active drugs must be administered in relatively high dosage to compensate for the intrinsically low intracellular uptake of the active drug. The polarity and negatively-charged structure of the active drug impairs transport across the cellular membrane, which compromises its ability to deliver therapeutic levels to infected cells. Ongoing needs exist to develop formulation and administration strategies that can deliver active drugs, illustratively cidofovir and foscarnet, to infected areas (e.g. cells and tissues) at levels that efficiently treat the diseased area while maintaining the concentration of the active drug at levels that do not induce toxicity. Other lipophilic prodrug approaches have been reported (US 2011/0263535A1, US 2007/003608A1), but these strategies result in too great a lipophilicity imparted to the drugs resulting in poorer water solubility and a tendency of the prodrug to be metabolized before reaching the infected cell.

Thus, there exists a need for a prodrug strategy to improve bioavailability of hydrophilic bioactive molecules. There also exists a need for methods and compositions to treat viral infections with highly polar antiviral agents, illustratively those that have been proven to be effective against ganciclovir and acyclovir resistant viruses and which utilize lipophilic prodrugs designed for improved solubility, to limit undesired metabolism, and reduce the side effects of the parent drugs.

SUMMARY

The present disclosure reveals that drug lipophilicity can be modulated with the insertion of a sulfonyl group ($SO_2$) into the lipid chain that provides enough lipophilicity to overcome deficits of the parent drugs and also provides improved physical properties.

According to some embodiments, a prodrug includes a therapeutic agent and one or more caps bound to the therapeutic agent. Optionally, 1, 2, 3, 4, or more caps may be bound to the therapeutic agent. Each of the one or more caps individually may having a structure according to formula (I):

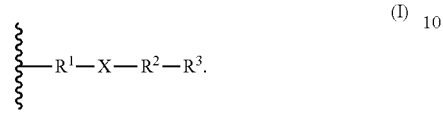

In formula (I): $R^1$ is a branched or linear substituted or unsubstituted C2-C6 alkyl, alkenyl, or alkynl; X is —S(O)$_2$—; $R^2$ is a branched or linear substituted or unsubstituted C4-C20 alkyl, alkenyl, or alkynyl; $R^3$ is —H, a substituted or unsubstituted C3-C5 cycloalkyl, a substituted or unsubstituted heterocycle with 4-6 atoms, C3-C5 cycloheteroalkyl, —C(CH$_3$)$_3$, —CF$_3$, —C(CF$_3$)$_3$, or a substituted or unsubstituted phenyl. Furthermore, when $R^3$ is a heterocycle of 4-5 atoms, the heteroatoms may be oxygen, sulfur, nitrogen, or a combination thereof. Optionally, when $R^3$ is —H, $R^2$ is chosen from: branched or linear substituted or unsubstituted C4-C16 alkyl, alkeneyl, or alkynyl; branched substituted or unsubstituted C17 alkyl, alkeneyl, or alkynyl; or branched or linear substituted or unsubstituted C18-C20 alkyl, alkenyl, or alkynyl.

The therapeutic agent of the prodrug optionally has a structure according to formula (II):

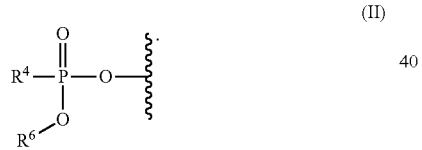

In formula (II) $R^4$ is optionally chosen from the following groups: —COOR$^5$ and

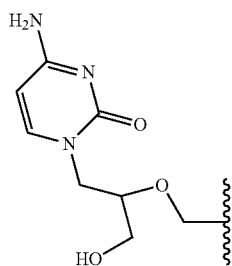

where $R^5$ is independently H or a C1-C4 substituted or unsubstituted linear or branched alkyl and $R^6$ is H or —R$^1$XR$^2$R$^3$ (Formula I).

Optionally, $R^4$ in formula (II) is

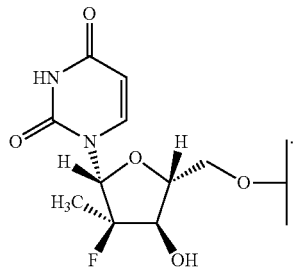 [SMILES: CC(C)OC[C@H]1O[C@@H](n2ccc(=O)[nH]c2=O)[C@](C)(F)[C@@H]1O]

Optionally, $R^4$ in formula (II) is

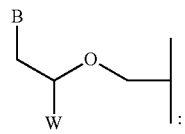

where B=A and W=CH$_2$OH and the therapeutic agent is(S)-9-[(2S)-3-hydroxy-2-phosphonylmethoxypropyl] adenine ((S)-HPMPA);

or B=A and W=H and the therapeutic agent is phosphonomethoxy-ethyl-adenine (PMEA);

or B=DAP and W=CH$_3$ and the therapeutic agent is 9-[2-(R)-(phosphonomethoxy) propyl]-2,6-diaminopurine ((R)-PMPDAP);

or B=A and W=CH$_2$F and the therapeutic agent is(S)-9-(3-fluoro-2-phosphonylmethoxypropyl) adenine ((S)-FPMPA);

or B=DAP and W=CH$_2$F and the therapeutic agent is(S)-9-[3-fluoro-2-phosphonylmethoxypropyl]diaminopurine ((S)-FPMPDAP);

or B=G and W=CH$_2$F and the therapeutic agent is(S)-9-(3-fluoro-2-phosphonylmethoxypropyl) guanine ((S)-FPMPG);

or B=DAP and W=CH$_2$F and the therapeutic agent is (R)-(S)-9-[3-fluoro-2-phosphonylmethoxypropyl]diaminopurine ((R)-FPMPDAP);

or B=G and W=CH$_2$F and the therapeutic agent is (R)-9-(3-fluoro-2-phosphonylmethoxypropyl) guanine (R)-FPMPG;

or B=7-deaza-G and W=H and the therapeutic agent is 7-deaza-9-(2-phosphonylmethoxyethyl) guanine (7-deaza-PMEG);

or B=8-aza-G and W=H and the therapeutic agent is 9-(2-phosphonylmethoxyethyl)-8-aza-guanine (PME-8-aza-G);

or B=8-aza-G and W=CH$_3$ and the therapeutic agent is (R)-(2-(phosphonomethoxy) propyl)-8-aza-guanine ((R)-PMP-8-aza-G);

or B=DAPy and W=H and the therapeutic agent is 6-[2-(phosphonomethoxy) ethoxy]-2,4-diaminopyrimidine (PMEO-DAPy);

or B=DAPy and W=CH$_3$ and the therapeutic agent is (R)-6-[2-(phosphonomethoxy) ethoxy]-2,4-diaminopyrimidine ((R)-PMPO-DAPy);

and the structural definitions of the abbreviations for B are:

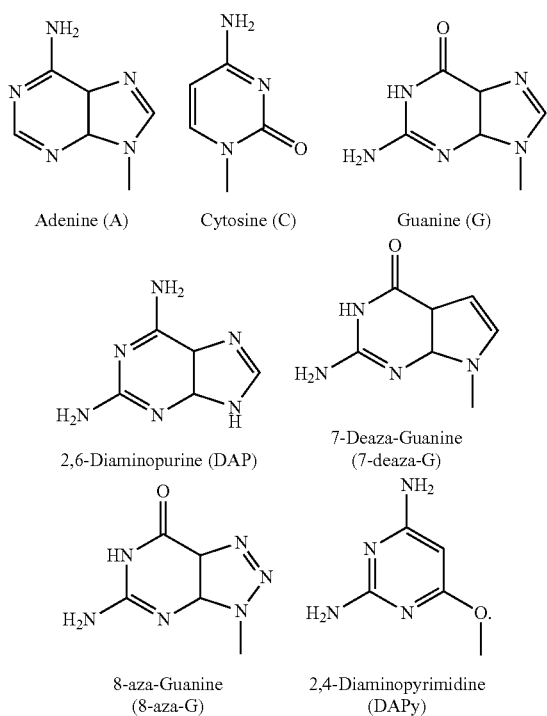

In further particular embodiments, a method of treatment includes administration of a prodrug having a cap according to formula (I) and a therapeutic agent according to formula (II) to a subject having a viral infection or a viral associated disease.

In embodiments, methods of treatment include oral administration of the prodrug having a cap according to formula (I) and a therapeutic agent according to formula (II).

In further embodiments, use of a compound described herein is provided. For example, use of prodrug having a cap according to formula (I) and a therapeutic agent according to formula (II) for the treatment of a subject with a viral disease. For example, with respect to viral diseases the improvement from treatment can be a lowering of the virus titer or a reduction in the symptoms or discomfort associated with the viral disease. The amount of lowering or reduction will vary depending on such particulars as the type of virus infection, the condition being treated, the actual prodrug and therapeutic agent being used and the severity of the condition and the characteristics of the patient.

In further embodiments the treatment with the prodrug of formula (I) and the therapeutic agent of formula (II) is to inhibit viral replication in viral infected cells in culture, in an isolated organ, in a person or in an animal. In the method of inhibiting viral replication or in treating a viral infection the virus is a DNA virus which may include, but are not limited to members of the Herpesviridae, Adenoviridae, Poxviridae, and Papillomaviridae. Examples of particular viruses include but are not limited to the sensitive and resistant strain of Herpes simplex I, Herpes simplex II, cytomegalovirus, Vericella-Zoster Virus, Epstein-Barr Virus, Human Herpes Viruses type 6 and 8, Papilloma virus, BK virus, and Adenovirus.

BRIEF DESCRIPTION OF THE DRAWINGS

The aspects set forth in the drawings are illustrative and exemplary in nature and not intended to limit the subject matter defined by the claims. The following detailed description of the illustrative aspects can be understood when read in conjunction with the following drawings in which:

DETAILED DESCRIPTION

Figure 1:
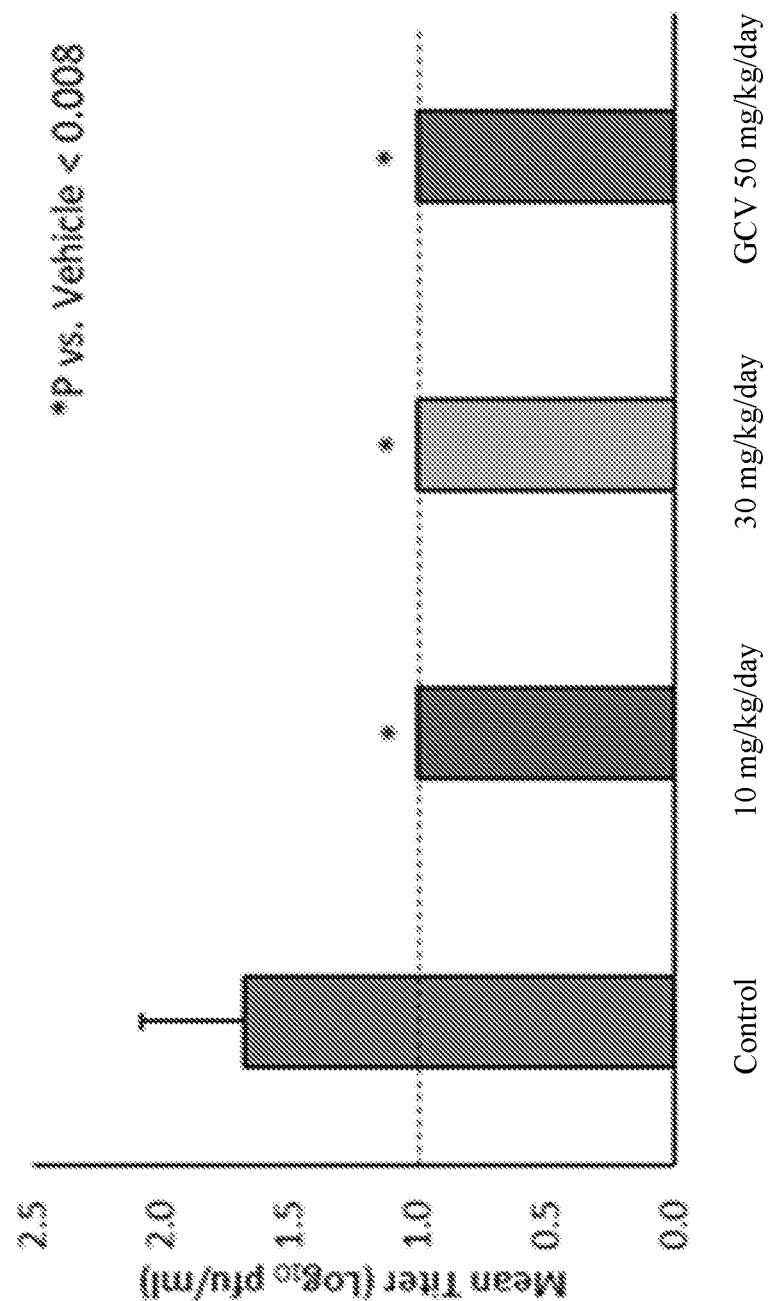
FIG. 1 illustrates in vivo efficacy of compound 122 against mCMV infection relative to ganciclovir (GCV) or vehicle control measured in liver following PO dosing.

The prodrugs of this disclosure enhance the bioavailability of a desired therapeutic agent. Bioavailability is defined herein as the amount of drug systemically available in comparison to the total amount of drug delivered to an individual. Bioavailability is typically expressed as percent (%) bioavailability and is generally measured by comparing plasma levels of drug after oral administration to plasma levels of drug after intravenous administration. This definition includes first pass metabolism, that is gut and liver metabolism, which when it occurs, occurs before the drug is available systemically. Thus, highly metabolized drugs may be completely absorbed but have a bioavailability less than 100 percent. Bioavailability is directly related to the fraction of a drug absorbed or "fraction absorbed", which refers to the percent of a total orally delivered drug dose transported or diffused across the luminal membranes of the gastrointestinal tract into the portal vein.

The term "independently selected" is used herein to indicate that the R groups, such as, $R^1$, $R^2$, $R^3$, $R^4$, and $R^5$, can be identical or different (e.g., $R^1$, $R^2$, $R^3$, $R^4$, and $R^5$ may all be substituted alkyls or $R^1$ and $R^2$ may be a substituted alkyl and $R^3$ may be an aryl, etc). A chemical name associated with an R group is intended to convey the chemical structure that is recognized in the art as corresponding to that of the chemical name. Thus, chemical names are intended to supplement and illustrate, not preclude, the structural definitions known to those of skill in the art.

When used to describe certain carbon atom-containing chemical groups, a parenthetical expression having the form "Cx-Cy" means that the unsubstituted form of the chemical group has from x carbon atoms to y carbon atoms, inclusive of x and y. For example, a C4-C20 alkyl is an alkyl group or radical having from 4 to 20 carbon atoms in its unsubstituted form. As another example, C2-C6 alkyl is an alkyl group or radical having from 2 to 6 carbon atoms in its unsubstituted form.

The term "alkyl" means a saturated straight or branched saturated hydrocarbon radical of from x to y carbon atoms. The carbons of the radical may be substituted or unsubstituted.

The term "alkenyl" means an unsaturated straight or branched hydrocarbon radical of from x to y carbon atoms and includes at least one carbon-carbon double bond. The carbons of the radical may be substituted or unsubstituted.

The terms "alkynyl" means an unsaturated straight or branched hydrocarbon radical of from x to y carbon atoms and includes at least one carbon-carbon triple bond. The carbons of the radical may be substituted or unsubstituted.

The term "cycloalkyl" means a saturated cyclic hydrocarbon radical of from x to y carbon atoms. For example, Cx-Cy cycloalkyl is defined as having from x to y carbon atoms. Examples of unsubstituted ($C_3$-$C_8$) cycloalkyl are cyclopropyl, cyclobutyl, cyclopentyl, cyclohexyl, cycloheptyl, cyclooctyl.

The term "saturated" means lacking carbon-carbon double bonds, carbon-carbon triple bonds, and (in heteroatom-containing groups) carbon-nitrogen, carbon-phosphorous, and carbon-silicon double bonds. The term "unsaturated" means containing one or more carbon-carbon double bonds, carbon-carbon triple bonds, and (in heteroatom-containing groups) carbon-nitrogen, carbon-phosphorous, and carbon-silicon double bonds.

The term "heteroatom," refers to an atom other than hydrogen or carbon. Examples of groups containing one or more than one heteroatom include $P(R^P)_2$, $P(R^P)$, $N(R^N)_2$, $N(R^N)$, N, O, $OR^C$, S, $SR^C$, S(O), and $S(O)_2$, or other groups containing one or more of the foregoing wherein R is a linear, branched, or cyclic alkyl, alkenyl, or alkynl.

The term "heterocycle" means a cyclic, optionally fused cyclic, radical containing any number equal to or greater than 3, optionally 4-10, total ring atoms of which at least one atom is a carbon atom. The heteroatoms of the heterocycles may include $N(R^N)_2$, $N(R^N)$, N, O, $OR^C$, S, $SR^C$, S(O), and $S(O)_2$, wherein each of the heteroalkyl are unsubstituted or substituted. Examples of heterocycles with 4-6 total atoms (as an example) are oxetane, tetrahydofuran, morpholine, furan, piperazine, pyridine, thiazole, oxazole, tetrahydropyran, and thiomorpholine dioxide.

The term "substituted" means that at least one hydrogen atom (—H) bonded to a carbon atom or heteroatom of a corresponding unsubstituted compound or functional group is replaced by a substituent. Examples of such substituents are F, Cl, Br, OH, $CF_3$, $NH_2$, $NHR^N$, $N(R^N)_2$. The term "—H" means a hydrogen or hydrogen radical that is covalently bonded to another atom. "Hydrogen" and "—H" are interchangeable, and unless clearly specified have identical meanings.

The prodrugs of the present disclosure may have a chiral center. In such circumstances both an R and an S form are specifically disclosed and are optional embodiments of the recited or claimed structure unless otherwise presented herein. In some embodiments a compound is provided as an isolated enantiomer or as a racemic mixture.

The prodrugs of the present disclosure include a therapeutic agent according to formula (II) for the treatment of a disease state, and a cap or promoiety that is covalently bound to the therapeutic agent. The prodrugs of this disclosure have utility as a therapeutic agent for the treatment of a variety of disease states.

Embodiments of this disclosure include prodrugs that include a therapeutic agent and one or more caps where the therapeutic agent is covalently bound to the cap, optionally 1, 2, 3, 4, or more caps. The cap having a structure according to formula (I)

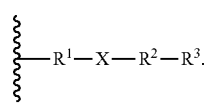

(I)

In formula (I), $R^1$ is a branched or linear substituted or unsubstituted C2-C6 alkyl, alkeneyl, or alkynl; X is —$S(O)_2$—; $R^2$ is chosen from a branched or linear substituted or unsubstituted C4-C20 alkyl, alkenyl, or alkynyl; $R^3$ is chosen from —H, a substituted or unsubstituted C3-C5 cycloalkyl, a substituted or unsubstituted heterocycle with 4-6 atoms in the cycle, substituted phenyl, —$C(CH_3)_3$, —$CF_3$, —$C(CF_3)_3$, or —$C_6F_5$. Furthermore, when $R^3$ is a heterocycle of 4-5 atoms in the cycle, wherein the heteroatoms may be oxygen, sulfur or nitrogen. Optionally, when $R^3$ is —H, $R^2$ is chosen from: branched or linear substituted or unsubstituted C4-C16 alkyl, alkenyl, or alkynyl; branched substituted or unsubstituted C17 alkyl, alkenyl, or alkynyl; or branched or linear substituted or unsubstituted C18-C20 alkyl, alkenyl, or alkynyl The therapeutic agent of the prodrug of this disclosure has a structure according to formula (II):

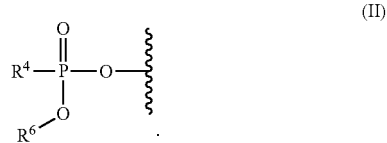

(II)

In some aspects of formula (II), $R^4$ is chosen from the following groups: —$COOR^5$ or

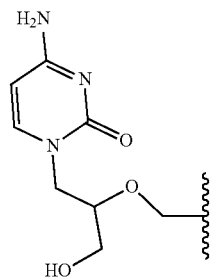

where $R^5$ is independently H or a C1-C4 substituted or unsubstituted linear or branched alkyl radical; and $R^6$ is H, a substituted or unsubstituted heterocycle with 4-6 atoms in the cycle, substituted or unsubstituted phenyl, or —$R^1XR^2R^3$ (formula I).

Optionally, $R^4$ in formula (II) is

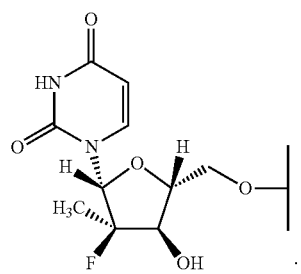 [SMILES: CC(C)OC[C@H]1O[C@@H](n2ccc(=O)[nH]c2=O)[C@](C)(F)[C@@H]1O]

Optionally, $R^4$ in formula (II) is

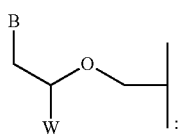

where B=A and W=$CH_2OH$ and the therapeutic agent is (S)-HPMPA;
or B=A and W=H and the therapeutic agent is PMEA;
or B=DAP and W=$CH_3$ and the therapeutic agent is (R)-PMPDAP;
or B=A and W=$CH_2F$ and the therapeutic agent is (S)-FPMPA;
or B=DAP and W=$CH_2F$ and the therapeutic agent is (S)-FPMPDAP;
or B=G and W=$CH_2F$ and the therapeutic agent is (S)-FPMPG;
or B=DAP and W=$CH_2F$ and the therapeutic agent is (R)-FPMPDAP;
or B=G and W=$CH_2F$ and the therapeutic agent is (R)-FPMPG;
or B=7-deaza-G and W=H and the therapeutic agent is 7-deaza-PMEG;
or B=8-aza-G and W=H and the therapeutic agent is PME-8-aza-G;
or B=8-aza-G and W=$CH_3$ and the therapeutic agent is (R)-PMP-8-aza-G;
or B=DAPy and W=H and the therapeutic agent is PMEO-DAPy;
or B=DAPy and W=$CH_3$ and the therapeutic agent is (R)-PMO-DAPy
and the structural definitions of the abbreviations for B are:

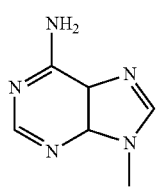 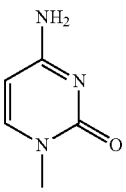 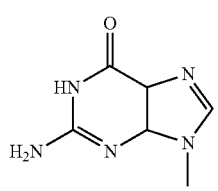

Adenine (A)　　Cytosine (C)　　Guanine (G)

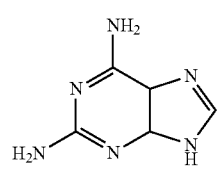 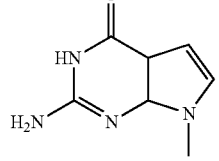

2,6-Diaminopurine (DAP)　　7-Deaza-Guanine (7-deaza-G)

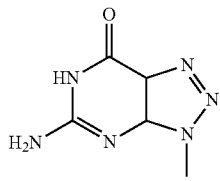 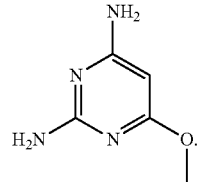

8-aza-Guanine (8-aza-G)　　2,4-Diaminopyrimidine (DAPy)

In one or more embodiments of formula (I) of the prodrug, $R^3$ is cyclopropyl, cyclobutyl, 2-trifluoromethyl cyclopropane-1-yl, 1-trifluoromethyl cyclopropane-1-yl, or —$CF_3$. In some embodiments, $R^3$ is a radical having a structure according to formula (III) or formula (IV):

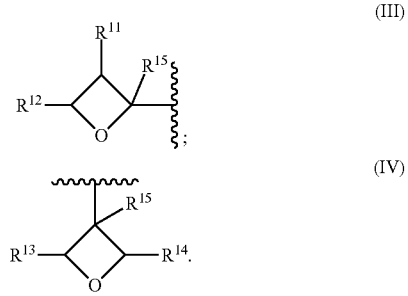

In formula (III) and formula (IV), $R^{11}$, $R^{12}$, $R^{13}$, $R^{14}$, or $R^{15}$ are independently chosen from a C1-C12 alkyl radical, —$CF_3$, —OH, or —H.

In one or more embodiments of formula (I) of the prodrug, $R^2$ is linear C4-C20 alkyl. Optionally, $R^2$ is chosen from —$CH_2CH_2$—, —$(CH_2)_3$—, —$(CH_2)_4$—, —$(CH_2)_5$—, —$(CH_2)_6$—. In other embodiments, $R^2$ is branched C4-C20 alkyl, such as —$CH_2C^*HCH_3$, and —$(CH_2)C^*(H)(CH_3)$, in which "C*" denotes a carbon atom from which a hydrogen atom is removed to form a secondary alkyl radical.

In one or more embodiments of formula (I) of the prodrug, $R^3$ is cyclobutyl, $R^2$ is —$CH_2(CH_2)_{12}CH_2$—, and $R^1$ is —$CH_2(CH_2)_2CH_2$—.

In illustrative aspects, a composition is provided herein according to formula (V):

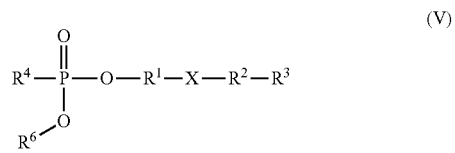

wherein $R^1$ is a linear substituted or unsubstituted C2-C6 alkyl, alkeneyl, or alkynl; X is —$S(O)_2$—; $R^2$ is a linear substituted or unsubstituted C4-C20 alkyl, alkenyl, or alkynyl; $R^3$ is chosen from —H, —$C(CH_3)_3$, —$CF_3$, —$C(CF_3)_3$, —$C_6F_5$, formula (III), or formula (IV); $R^4$ is chosen from the following groups: —$COOR^5$ or

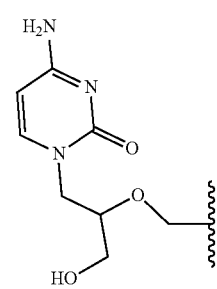

where $R^5$ is independently H or a C1-C4 substituted or unsubstituted linear or branched alkyl radical; or wherein $R^4$ is

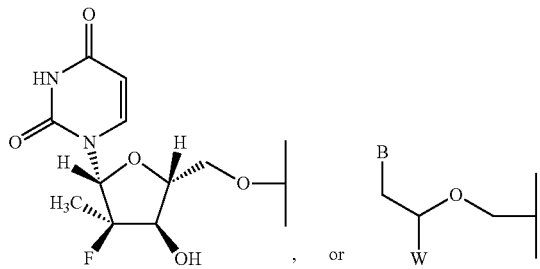

wherein B and W are as defined above; where $R^6$ is H, a substituted or unsubstituted heterocycle with 4-6 atoms in the cycle, substituted or unsubstituted phenyl, or —$R^1XR^2R^3$ (formula (I)); or salt thereof.

In some aspects, a prodrug composition is provided herein according to formula V wherein $R^1$ is a linear substituted or unsubstituted C2-C6 alkyl, alkeneyl, or alkynl; X is —$S(O)_2$—; $R^2$ is a linear substituted or unsubstituted C4-C20 alkyl, alkenyl, or alkynyl; $R^3$ is chosen from —H, —$C(CH_3)_3$, —$CF_3$, —$C(CF_3)_3$, —$C_6F_5$, formula (III), or formula (IV); $R^4$ is —$COOR^5$ where $R^5$ is independently H or a C1-C4 substituted or unsubstituted linear or branched alkyl radical; and $R^6$ is H or —$R^1XR^2R^3$ (formula (I)); or salt thereof.

In some aspects, a prodrug composition is provided herein according to formula (V) wherein $R^1$ is a linear substituted or unsubstituted C2-C6 alkyl, alkeneyl, or alkynl; X is —$S(O)_2$—; $R^2$ is a linear substituted or unsubstituted C4-C20 alkyl, alkenyl, or alkynyl; $R^3$ is chosen from —H, —$C(CH_3)_3$, —$CF_3$, —$C(CF_3)_3$, —$C_6F_5$, formula (III), or formula (IV); $R^4$ is

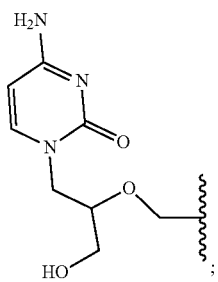 [SMILES: *COC(CO)Cn1ccc(N)nc1=O]

and $R^6$ is H or —$R^1XR^2R^3$ (formula (I)); or salt thereof.

In some aspects, a prodrug composition is provided herein according to formula (V) wherein $R^1$ is a linear substituted or unsubstituted C2-C6 alkyl, alkeneyl, or alkynl; X is —$S(O)_2$—; $R^2$ is a linear substituted or unsubstituted C4-C20 alkyl, alkenyl, or alkynyl; $R^3$ is chosen from —H, —$C(CH_3)_3$, —$CF_3$, —$C(CF_3)_3$, —$C_6F_5$, formula (III), or formula (IV); $R^4$ is

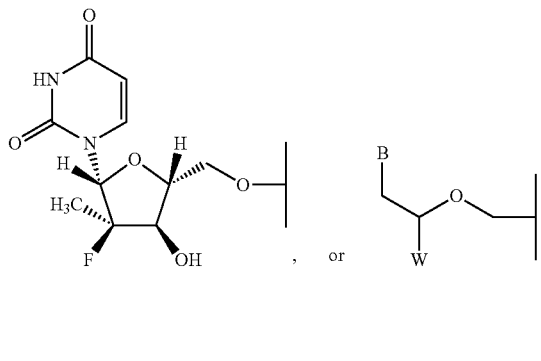

wherein B and W are as defined above and $R^6$ is H or —$R^1XR^2R^3$ (formula (I)); or salt thereof.

In some aspects, a prodrug composition is provided herein according to formula (V) wherein $R^1$ is a linear unsubstituted C2-C6 alkyl; X is —$S(O)_2$—; $R^2$ is a linear unsubstituted C4-C20 alkyl; $R^3$ is chosen from —H, —$C(CH_3)_3$, —$CF_3$, —$C(CF_3)_3$, —$C_6F_5$, formula (III), or formula (IV); $R^4$ is —$COOR^5$ where $R^5$ is H or a C1-C4 unsubstituted linear alkyl radical; and $R^6$ is H or —$R^1XR^2R^3$ (formula (I)); or salt thereof.

In some aspects, a prodrug composition is provided herein according to formula (V) wherein $R^1$ is a linear unsubstituted C2-C6 alkyl; X is —$S(O)_2$—; $R^2$ is a linear unsubstituted C4-C20 alkyl; $R^3$ is chosen from —H, —$C(CH_3)_3$, —$CF_3$, —$C(CF_3)_3$, —$C_6F_5$, formula (III), or formula (IV); $R^4$ is

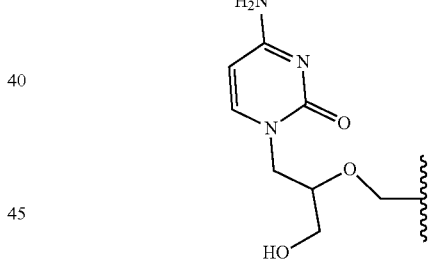

and $R^6$ is H or —$R^1XR^2R^3$ (formula (I)); or salt thereof.

In some aspects, a prodrug composition is provided herein according to formula (V) wherein $R^1$ is a linear unsubstituted C2-C6 alkyl; X is —$S(O)_2$—; $R^2$ is a linear unsubstituted C4-C20 alkyl; $R^3$ is chosen from —H, —$C(CH_3)_3$, —$CF_3$, —$C(CF_3)_3$, —$C_6F_5$, formula (III), or formula (IV); $R^4$ is —$COOR^5$ where $R^5$ is independently H or a C1-C4 unsubstituted linear alkyl radical; and $R^6$ is H; or salt thereof.

In some aspects, a prodrug composition is provided herein according to formula (V) wherein $R^1$ is a linear unsubstituted C2-C6 alkyl; X is —$S(O)_2$—; $R^2$ is a linear unsubstituted C4-C20 alkyl; $R^3$ is chosen from —H, —$C(CH_3)_3$, —$CF_3$, —$C(CF_3)_3$, —$C_6F_5$, formula (III), or formula (IV); $R^4$ is

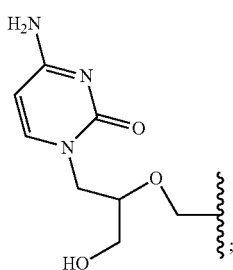

and $R^6$ is H; or salt thereof.

In some aspects, a prodrug composition is provided herein according to formula (V) wherein $R^1$ is a linear unsubstituted C2-C6 alkyl; X is —S(O)$_2$—; $R^2$ is a linear unsubstituted C4-C20 alkyl, alkenyl, or alkynyl; $R^3$ is chosen from —H, —C(CH$_3$)$_3$, —CF$_3$, —C(CF$_3$)$_3$, —C$_6$F$_5$, formula (III), or formula (IV); $R^4$ is

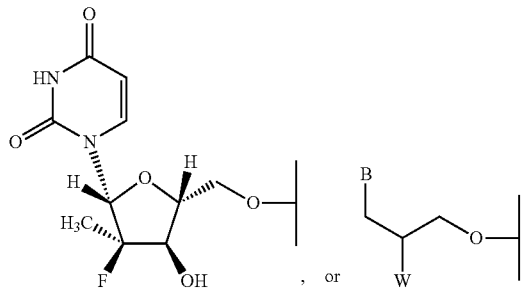

wherein B and W are as defined above and $R^6$ is H; or salt thereof.

In some aspects, a prodrug composition is provided herein according to formula (V) wherein $R^1$ is a linear unsubstituted C2-C6 alkyl; X is —S(O)$_2$—; $R^2$ is a linear unsubstituted C4-C20 alkyl; $R^3$ is chosen from —H, —C(CH$_3$)$_3$, —CF$_3$, —C(CF$_3$)$_3$, —C$_6$F$_5$, formula (III), or formula (IV); $R^4$ is —COOR$^5$ where $R^5$ is independently H or a C1-C4 unsubstituted linear alkyl radical; and $R^6$ is phenyl or —R$^1$XR$^2$R$^3$ (formula (I)); or salt thereof.

In some aspects, a prodrug composition is provided herein according to formula (V) wherein $R^1$ is a linear unsubstituted C2-C6 alkyl; X is —S(O)$_2$—; $R^2$ is a linear unsubstituted C4-C20 alkyl; $R^3$ is chosen from —H, —C(CH$_3$)$_3$, —CF$_3$, —C(CF$_3$)$_3$, —C$_6$F$_5$, formula (III), or formula (IV); $R^4$ is

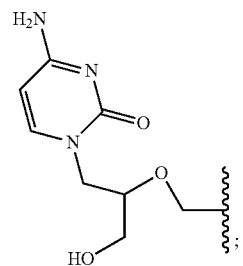

and $R^6$ is a phenyl —R$^1$XR$^2$R$^3$ (formula (I)); or salt thereof.

In some aspects, a prodrug composition is provided herein according to formula (V) wherein $R^1$ is a linear unsubstituted C2-C6 alkyl; X is —S(O)$_2$—; $R^2$ is a linear unsubstituted C4-C20 alkyl, alkenyl, or alkynyl; $R^3$ is chosen from —H, —C(CH$_3$)$_3$, —CF$_3$, —C(CF$_3$)$_3$, —C$_6$F$_5$, formula (III), or formula (IV); $R^4$ is

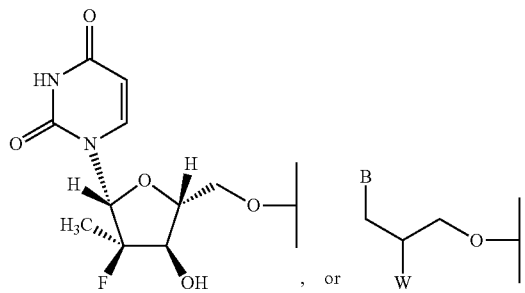

wherein B and W are as defined above and $R^6$ is a phenyl or —R$^1$XR$^2$R$^3$ (formula (I)); or salt thereof.

Illustrative embodiments of prodrugs as provided herein include but are not limited to:

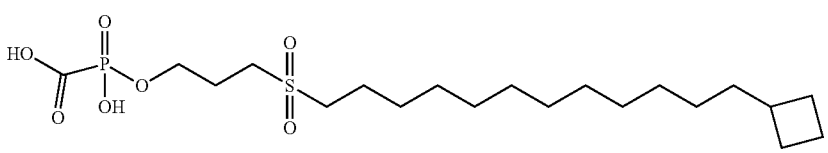

101

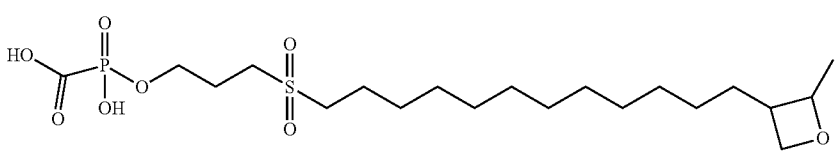

102

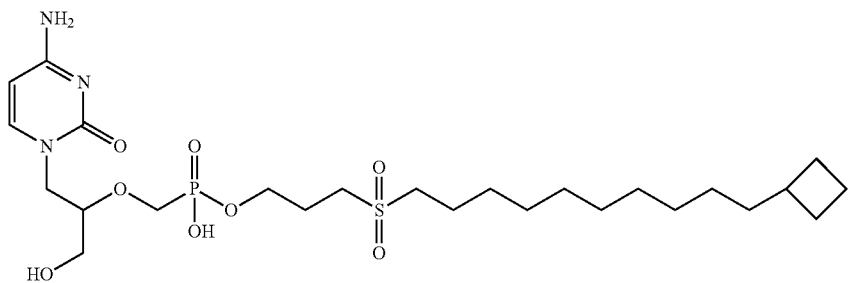
103
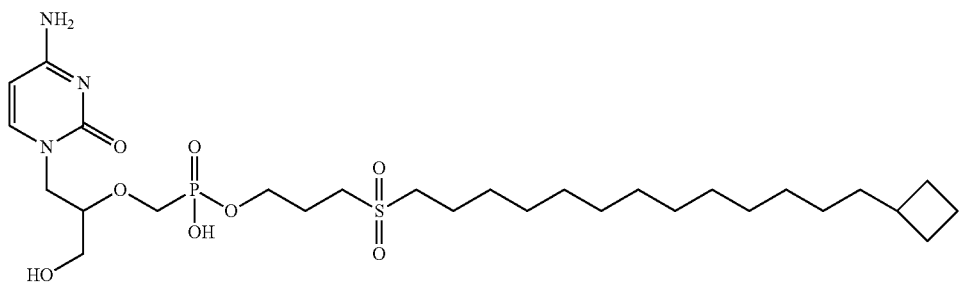
104
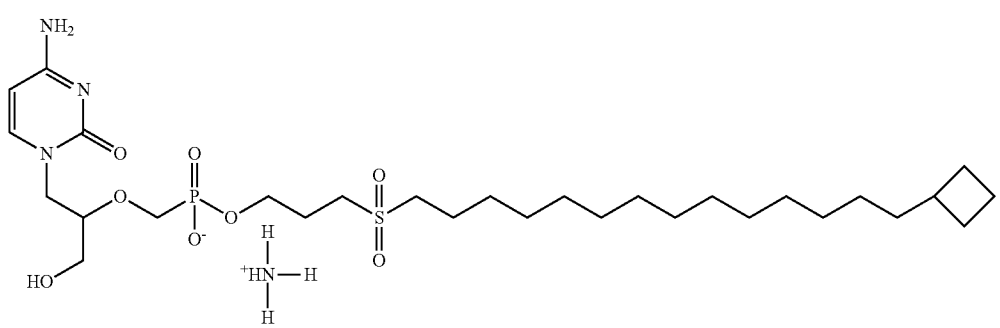
105
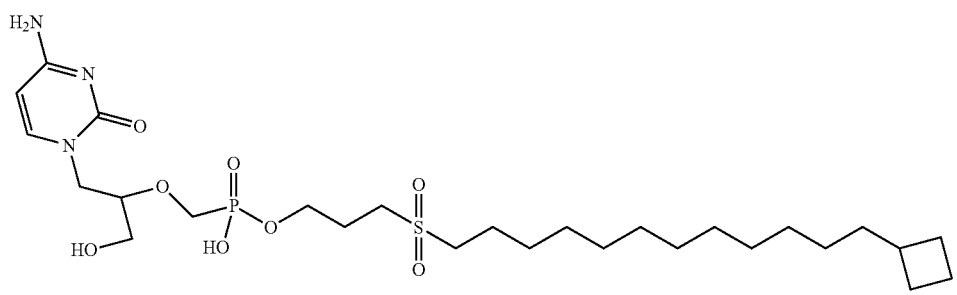
106
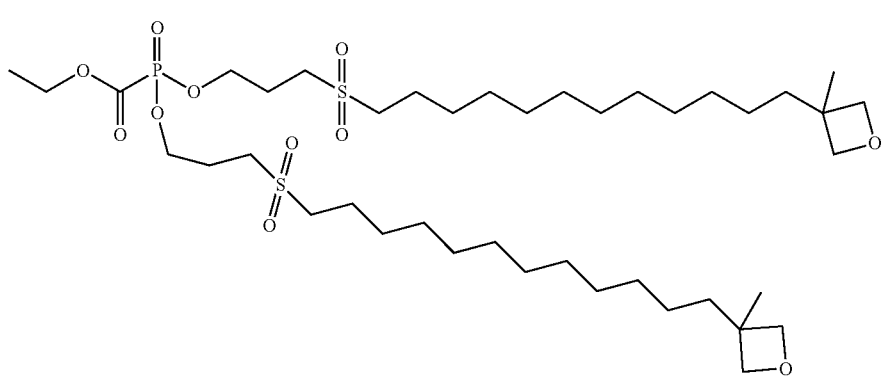
107

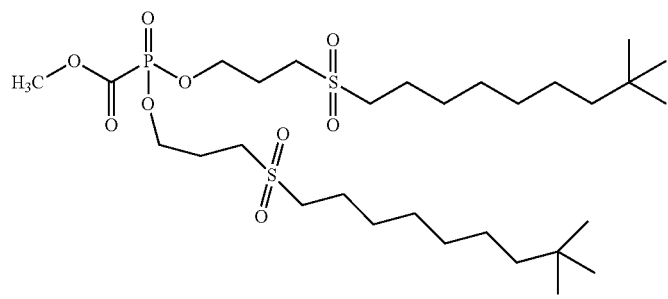
108
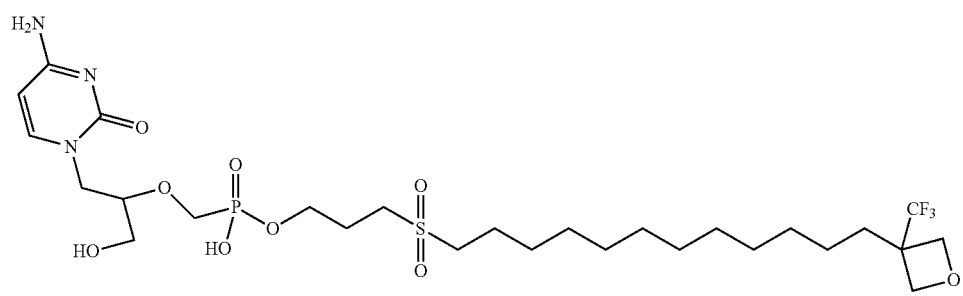
109
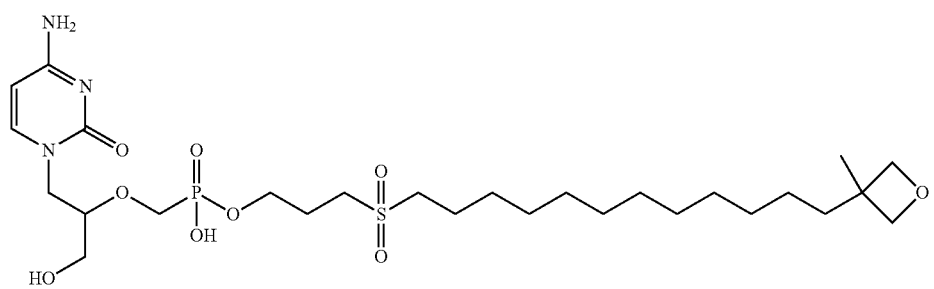
110
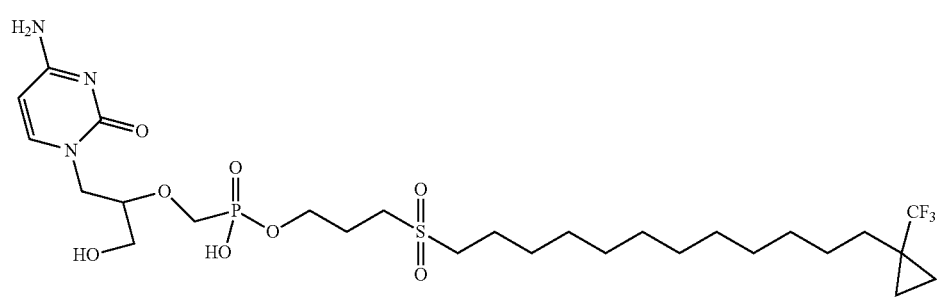
111
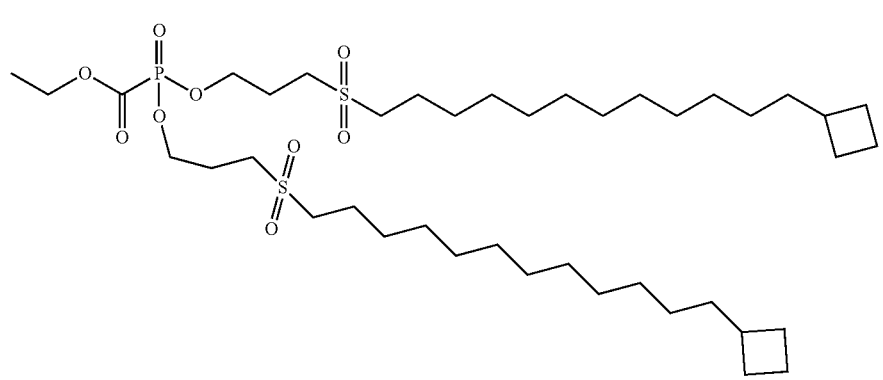
112

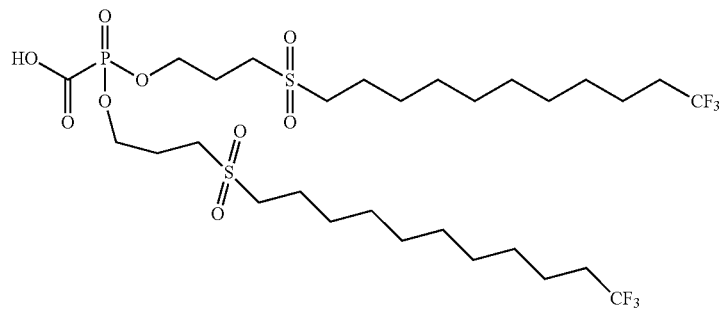
113
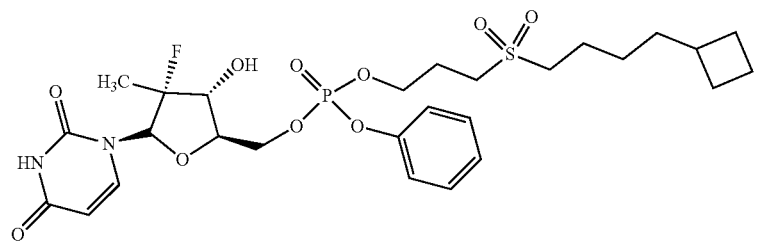
114
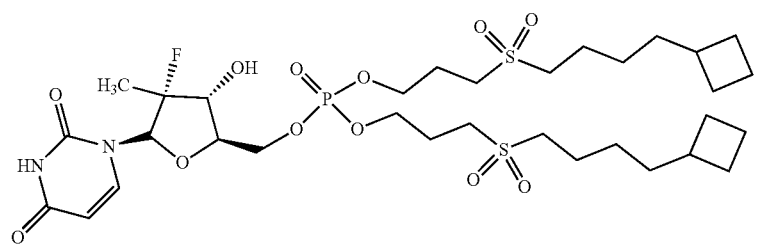
115
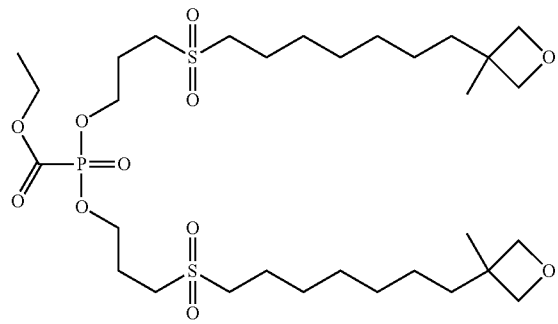
116
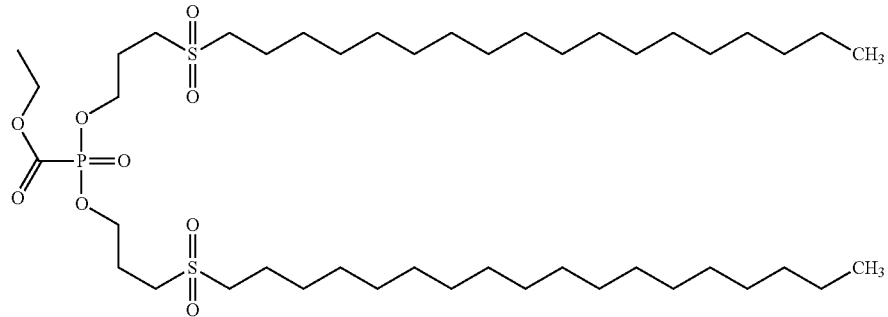
117

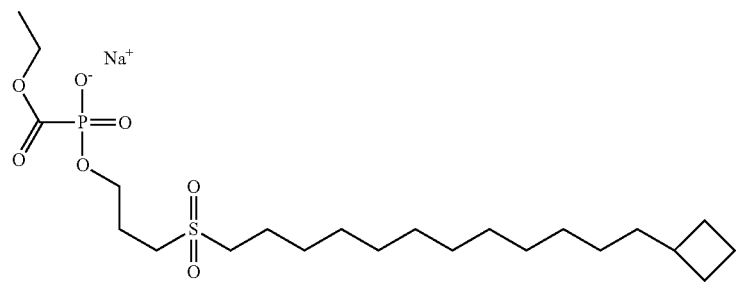

118

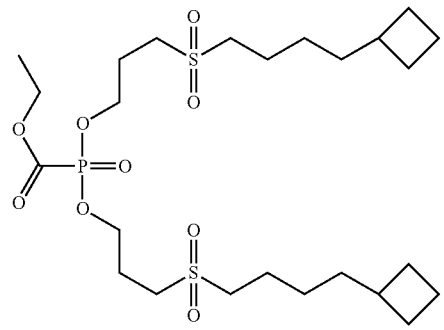

119

It is appreciated that prodrugs according to the present disclosure are readily created to treat a variety of herpes virus related diseases illustratively including shingles, chicken pox, blisters or sores on the mouth or genital organs, cytomegalovirus infections after organ transplants, mononucleosis, and certain cancers. In embodiments, the prodrugs of this disclosure are formulated for administration to a human individual, and bioavailability and fraction absorbed measurements refer to measurements made in humans. However, it is appreciated that the prodrugs of this disclosure and method of treatment may be indicated in non-human applications as well. Thus, an inventive prodrug is advantageously administered to a non-human organism such as a rodent, bovine, equine, avian, canine, feline or other such species wherein the organism possesses an enzyme and a membrane transporter for which the prodrug is a substrate.

In embodiments, methods of treating a patient according to the present disclosure include administering a therapeutically effective amount of the prodrug having a cap according to formula (I) and a therapeutic agent according to formula (II) to an organism in need.

In one or more embodiments, methods for delivering the therapeutic agent according to formula (II) to an individual include administering to a subject one prodrug or more than one prodrug as described herein to the gastrointestinal lumen or other desired site of interest of the subject. As used herein, the terms "subject" and "patient" are synonymous and refer to a human or non-human animal, optionally a mammal including non-primates such as cows, pigs, horses, goats, sheep, cats, dogs, avian species and rodents; a non-human primate such as monkeys, chimpanzees, and apes; and a human, also optionally denoted specifically as a "human subject". It is appreciated that a subject is optionally a cell, tissue, or organ.

The presently provided compositions address the relatively low bioavailability of the therapeutic agent, more effectively target the therapeutic agent to the desired site of action such as the site of infection or infected cell, tissue, or organ, reduce toxicity by reducing the amount of drug required to elicit a therapeutic effect in a subject, cause the distribution of the therapeutic agent in the subject to be optimized or targeted, or any combination thereof. In some embodiments, the prodrugs as provided herein include as a therapeutic agent component therapeutic agents characterized by bioavailability in a human of 30 percent or less, optionally 10% or less, optionally 5% or less. Optionally, a therapeutic agent has a molecular weight in the range of 100-1000 Daltons.

Variable dosing regimens are operative in the method of treatment. While single dose treatment is effective in producing therapeutic effects, it is noted that longer courses of treatment such as several days to weeks have previously been shown to be efficacious in prodrug therapy (Beck et al., Human Gene Therapy, 6:1525-30 (1995)). While dosimetry for a given inventive prodrug will vary, dosimetry will depend on factors illustratively including target cell mass, effective active species, specifically the therapeutic agent according to formula (II), cellular concentration, transporter efficiency, systemic prodrug degradation kinetics, and secondary enzymatic cleavage that reduces active species lifetime.

The prodrug of this disclosure may be administered by a route determined to be appropriate for a particular subject by one skilled in the art. For example, the prodrug is administered orally; parenterally, such as intravenously; by intramuscular injection; by intraperitoneal injection; transdermally; or rectally. The exact dose of prodrug required is appreciated to vary from subject to subject, depending on the age, weight and general condition of the subject, the severity of the disease being treated, the particular pharmaceutical species, the mode of administration, and the like. An appropriate dose is readily determined by one of ordinary skill in the art using only routine experimentation given the teachings herein. Generally, dosage is in the range of about 0.5 to 500 mg/kg, optionally 0.5 to 100 mg/kg, 0.5 to 20 mg/kg, or 25-100 mg/kg where each dosage is on a per day basis.

Depending on the intended mode of administration, the prodrug can be in pharmaceutical compositions in the form of solid, semi-solid or liquid dosage forms, such as, for example, tablets, suppositories, pills, capsules, powders, liquids, or suspensions, preferably in unit dosage form suitable for single administration of a precise dosage. Time-release preparations are specifically contemplated as effective dosage formulations. The compositions will include an effective amount of the selected substrate in combination with a pharmaceutically acceptable carrier and, in addition, may include other medicinal agents, pharmaceutical agents, carriers, or diluents. Further, a prodrug may be formulated as a pharmaceutically acceptable salt.

Solid formulations may include conventional nontoxic solid carriers. A non-limiting list of nontoxic solid carriers include pharmaceutical grades of mannitol, lactose, starch, magnesium stearate, sodium saccharine, talc, cellulose, glucose, sucrose and magnesium carbonate. Liquid pharmaceutically administrable compositions may be prepared by dissolving or dispersing an active compound with optimal pharmaceutical adjuvants in an excipient, such as water, saline, aqueous dextrose, glycerol, or ethanol, to thereby form a solution or suspension. If desired, the pharmaceutical composition to be administered may also contain minor amounts of nontoxic auxiliary substances such as wetting or emulsifying agents, pH buffering agents, for example, sodium acetate or triethanolamine oleate. Actual methods of preparing such dosage forms are known, or will be apparent, to those skilled in this art; for example, see Remington's The Science and Practice of Pharmacy (20$^{th}$ Edition).

For oral administration, fine powders or granules may contain diluting, dispersing, and/or surface-active agents, and may be presented in water or in a syrup, in capsules or sachets in the dry state or in a nonaqueous solution or suspension wherein suspending agents may be included, in tablets wherein binders and lubricants may be included, or in a suspension in water or a syrup. Where desirable or necessary, flavoring, preserving, suspending, thickening, or emulsifying agents may be included. Tablets and granules are preferred oral administration forms, and these may be coated.

Parenteral administration is generally by injection. Injectables can be prepared in conventional forms, either liquid solutions or suspensions, solid forms suitable for solution or prior to injection, or as suspension in liquid prior to injection or as emulsions.

Various aspects of the present invention are illustrated by the following non-limiting examples. The examples are for illustrative purposes and are not a limitation on any practice of the present invention. It will be understood that variations and modifications can be made without departing from the spirit and scope of the invention. Reagents illustrated herein are commonly cross reactive between mammalian species or alternative reagents with similar properties are commercially available, and a person of ordinary skill in the art readily understands where such reagents may be obtained.

EXAMPLES

Example 1. Ammonium 3-((10-cyclobutyldecyl) sulfonyl)propyl Hydrogen ((((S)-1-(4-amino-2-oxopyrimidin-1(2H)-yl)-3-hydroxypropan-2-yl)oxy) methyl)phosphonate (120)

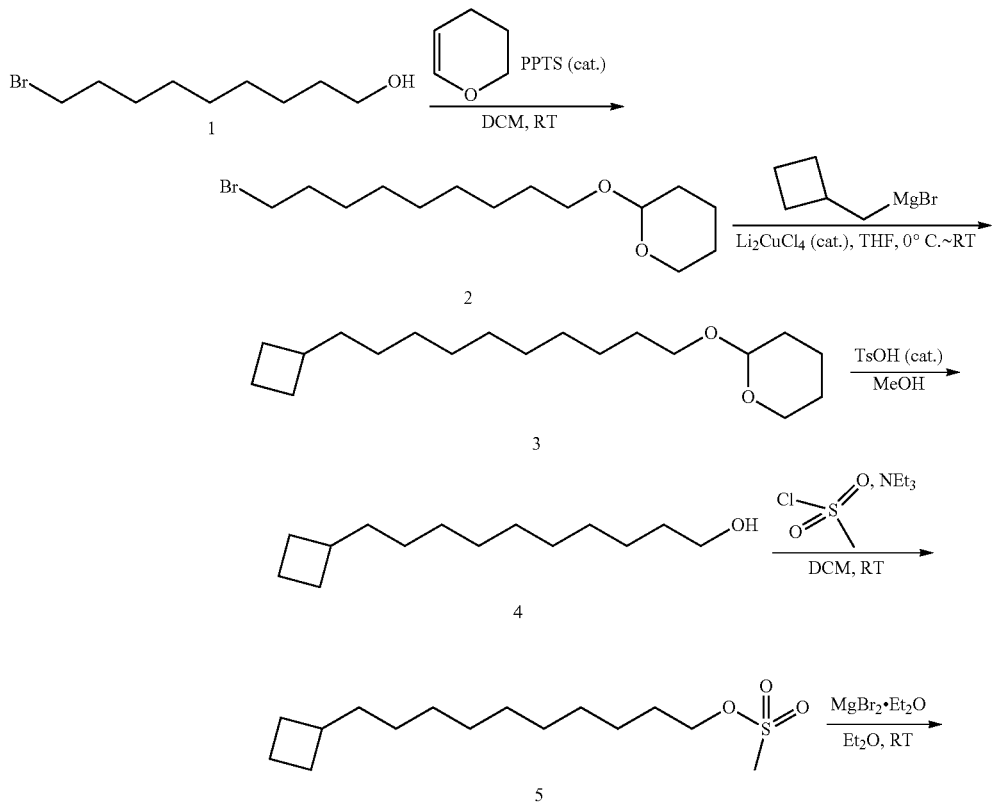

Scheme 1

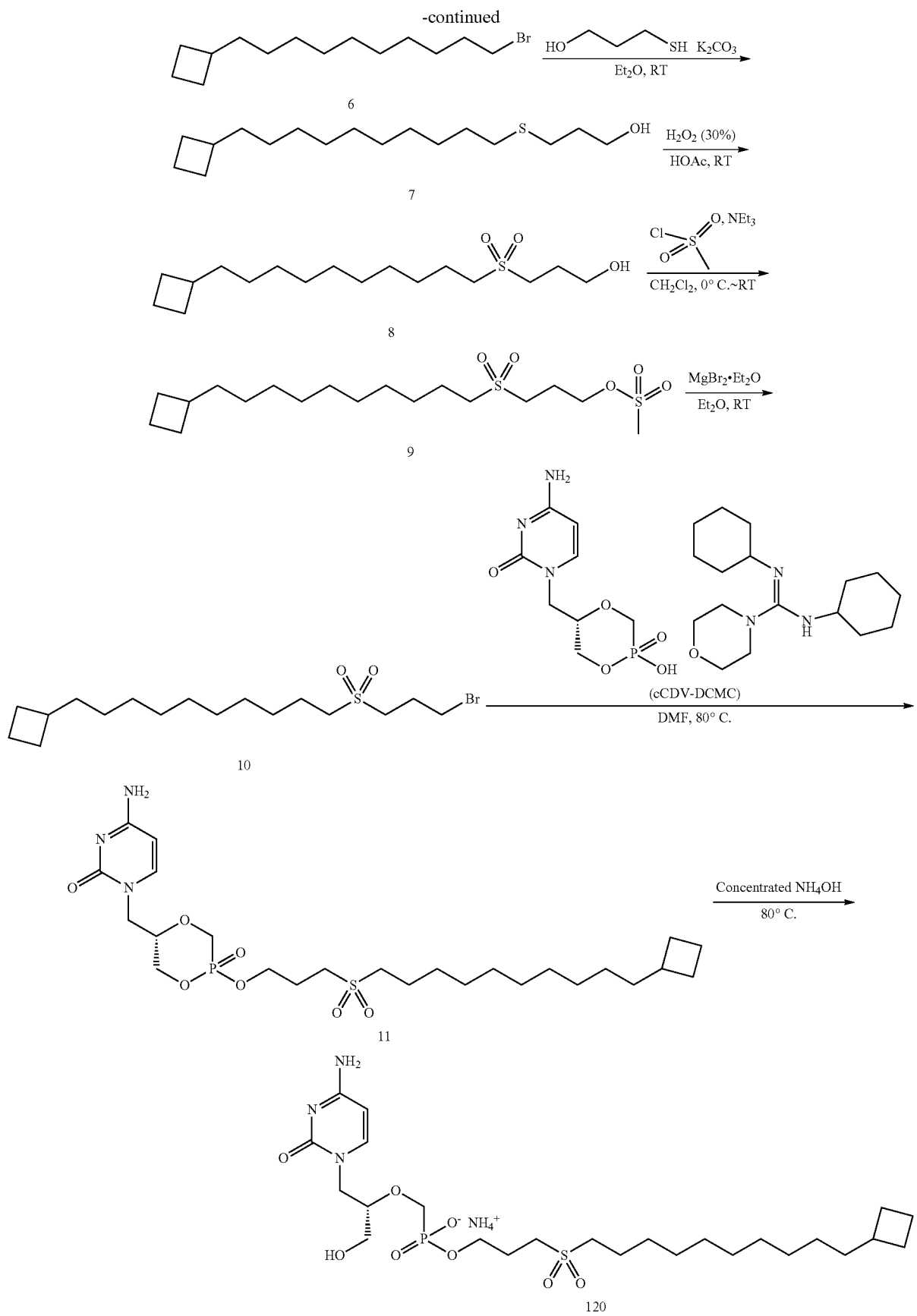

2-((9-Bromononyl)oxy)tetrahydro-2H-pyran (2). To a solution of 1 (10.0 g, 44.8 mmol) and 2,3-dihydro-2H-pyran (3.96 g, 47.1 mmol) in DCM (100 mL) was added pyridinium p-toluenesulfonate (PPTS) (1.69 g, 6.72 mmol) at RT. The mixture was stirred at RT for 16 hr. It was then concentrated. The residue was taken up in hexanes and filtered. The filtrate was concentrated under vacuum to leave a oil. The oil was dissolved in 10 ml hexane and purified by silica gel column chromatography (5% EtOAc in hexanes) to give 2 (11.7 g, 85%) as a colorless oil. 1H NMR (500 MHz, Chloroform-d) δ 4.57 (dd, J=4.5, 2.9 Hz, 1H), 3.87 (ddd, J=11.0, 7.5, 3.2 Hz, 1H), 3.73 (dt, J=9.6, 6.9 Hz, 1H), 3.54-3.45 (m, 1H), 3.43-3.36 (m, 3H), 1.88-1.78 (m, 3H), 1.76-1.69 (m, 1H), 1.63-1.48 (m, 6H), 1.46-1.39 (m, 2H), 1.37-1.25 (m, 8H).

2-((10-Cyclobutyldecyl)oxy)tetrahydro-2H-pyran (3). To a mixed solution of 2 (3.5 g, 11.4 mmol) in THF (30 mL) and $Li_2CuCl_4$ (0.1 M solution in THF, 5.7 mL, 0.57 mmol) at 0° C. was added Grignard reagent cyclobutylmethyl magnesium bromide which was made from (bromomethyl)cyclobutane (4.0 g, 26.8 mmol) and grinded magnesium turnings (1.31 g, 53.7 mmol) in $Et_2O$ (25 mL). After the addition completed, stirred at 0° C. for 30 min and then at RT for 16 hr. The reaction was quenched by $NH_4Cl$ at 0° C. Stirred at RT for 20 min. Then the mixture was treated with hexanes and water. Organic phase was washed by brine, dried over $Na_2SO_4$, and concentrated to give 3 (3.3 g, 98%) as a colorless oil. $^1$H NMR (500 MHz, Chloroform-d) δ 4.58 (t, J=3.7 Hz, 1H), 3.87 (ddd, J=11.0, 7.5, 3.2 Hz, 1H), 3.73 (dt, J=9.7, 6.9 Hz, 1H), 3.50 (dt, J=10.7, 4.8 Hz, 1H), 3.38 (dt, J=9.7, 6.7 Hz, 1H), 2.23 (p, J=7.8 Hz, 1H), 2.01 (dtd, J=11.4, 7.8, 3.2 Hz, 2H), 1.89-1.74 (m, 3H), 1.71 (ddd, J=12.1, 9.1, 3.2 Hz, 1H), 1.56 (dddd, J=20.7, 9.1, 6.1, 3.0 Hz, 9H), 1.42-1.20 (m, 13H), 1.17 (dd, J=10.7, 5.1 Hz, 2H).

10-Cyclobutyldecan-1-ol (4). p-Toluenesulphonic acid monohyfrate (106 mg, 0.557 mmol) was added to an emulsion of 3 (3.3 g, 11.1 mmol) in methanol (20 ml). The mixture was stirred at room temperature for 24 hr. Most of the methanol was removed under reduced pressure. Water (20 mL) was added to the residue, and the mixture was extracted with hexane (3×20 mL). The combined organic layers were washed with saturated aqueous $NaHCO_3$ and brine, dried over $Na_2SO_4$, and concentrated under vacuum to give 4 (2.3 g, 97%) as colorless oil $^1$H NMR (400 MHz, Chloroform-d) δ 3.61 (t, J=6.7 Hz, 2H), 2.23 (hept, J=7.8 Hz, 1H), 2.09-1.92 (m, 2H), 189-1.66 (n, 2H), 1.56 (pd, J=8.9, 3.1 Hz, 4H), 138-1.11 (n, 17H). $^1$C NMR (101 MHz, Chloroform-d) δ 62.87, 37.07, 36.19, 32.74, 29.68, 29.62, 29.59, 29.45, 28.38 (2C), 27.17, 25.75, 18.46 (2C).

10-Cyclobutyldecyl methanesulfonate (5). To a solution of 4 (2.1 g, 9.89 mmol) and triethylamine (1.2 g, 11.87 mmol) were dissolved in DCM (20 mL) and cooled to 0° C. Methanesulfonyl chloride (1.36 g, 11.87 mmol in DCM (10 mL) was added dropwise to the above solution over 5 min. The reaction was stirred at RT for 3 hr, quenched with 0.5 N aq HCl solution, and extracted three times with hexanes. The organic layer was then washed with $H_2O$, $NaHCO_3$, brine, dried over sodium sulfate, filtered, and concentrated under reduced pressure to give 5 (2.74 g, 95%) as wax-like soft solid. $^1$H NMR (400 MHz, Chloroform-d) δ 4.22 (t, J=6.6 Hz, 2H), 3.00 (s, 3H), 2.23 (dt, J=15.5, 7.8 Hz, 1H), 2.06-1.95 (m, 2H), 1.92-1.66 (m, 3H), 1.61-1.49 (m, 2H), 1.44-1.13 (m, 17H).

(10-Bromodecyl)cyclobutane (6). Magnesium bromide etherate (5.78 g, 22.38 mmol) and a stir bar were added to a 250 mL-round bottom flask. The flask was flushed with nitrogen. Anhydrous diethyl ether (50 mL) was added. A solution of 5 (2.6 g, 8.95 mmol) in 20 ml of $Et_2O$ was then added and the suspension was stirred 16 hr at RT. The $Et_2O$ layer of the suspension was poured into 50 mL of chilled water and transferred to a separating funnel. After shaking, the organic phase was separated. The aqueous phase was then extracted with ether (2×60 mL) and all ether phases were combined. The ether phase was washed with water (2×50 mL), brine (50 mL), and dried over anhydrous $Mg_2SO_4$. The solution was filtered, concentrated to afford 6 (2.35 g, 95%) as light orange oil. $^1$H NMR (400 MHz, Chloroform-d) δ 3.41 (t, J=6.9 Hz, 2H), 2.22 (h, J=7.8 Hz, 1H), 2.07-1.95 (m, 2H), 1.90-1.71 (m, 4H), 1.62-1.49 (m, 2H), 1.44-1.14 (m, 16H).

3-((10-Cyclobutyldecyl)thio)propan-1-ol (7). Under nitrogen, to a solution of 6 (2.3 g, 8.36 mmol) and 3-mercaptopropan-1-ol (1.16 g, 12.53 mmol) in acetone (15 mL) was added potassium carbonate (2.31 g, 16.71 mmol). The suspension was stirred at room temperature for 16 hr. The mixture was evaporated and the residue was partitioned between water and hexane. The organic phase was washed with 1 N sodium hydroxide, water, brine, dried over sodium sulfate, and evaporated under reduced pressure to give 7 (2.31 g, 96%) as white wax-like solid. $^1$H NMR (400 MHz, Chloroform-d) δ 3.77 (q, J=5.6 Hz, 2H), 2.64 (t, J=7.0 Hz, 2H), 2.56-2.49 (m, 2H), 2.22 (h, J=7.8 Hz, 1H), 2.08-1.95 (m, 2H), 1.91-1.72 (m, 4H), 1.72-1.65 (m, 1H), 1.64-1.50 (m, 5H), 1.40-1.14 (m, 15H).

3-((10-Cyclobutyldecyl)sulfonyl)propan-1-ol (8). To a solution of 7 (2.0 g, 6.98 mmol) in AcOH (55 mL) was added 30% $H_2O_2$ (14.3 mL, 140 mmol). The solution was kept in the dark for 16 hr. Then the solvent was evaporated under reduced pressure. The white solid residue was treated with DCM and sat. $NaHCO_3$. The organic phase was washed by brine, dried over $Na_2SO_4$, and evaporated to give 8 (2.2 g, 99%) as a white solid. $^1$H NMR (400 MHz, Chloroform-d) δ 3.82 (q, J=5.3 Hz, 2H), 3.18-3.08 (m, 2H), 3.03-2.94 (m, 2H), 2.22 (h, J=7.6 Hz, 1H), 2.15-2.06 (m, 2H), 2.01 (dtd, J=11.4, 7.6, 3.0 Hz, 2H), 1.82 (tddd, J=19.4, 13.8, 9.1, 6.6 Hz, 5H), 1.65-1.50 (m, 4H), 1.44 (p, J=7.1 Hz, 2H), 1.38-1.09 (m, 12H).

3-((10-Cyclobutyldecyl)sulfonyl)propyl methanesulfonate (9). 8 (1.1 g, 3.45 mmol) and triethylamine (0.42 g, 4.14 mmol) were dissolved in DCM (18 mL) and cooled to 0° C. Methanesulfonyl chloride (0.475 g, 4.14 mmol) was added dropwise via syringe to the stirred solution over 2 min. The reaction was stirred at RT for 3 hr, quenched with 0.5 N aq HCl solution and extracted 2 times with DCM. The organic layer was then washed with water, $NaHCO_3$, brine, dried over sodium sulfate, filtered, and concentrated under reduced pressure to give 9 (1.35 g, 99%) as a white soli. $^1$H NMR (400 MHz, Chloroform-d) δ 4.41 (t, J=5.9 Hz, 2H), 3.15-3.08 (m, 2H), 3.05 (s, 3H), 3.03-2.95 (m, 2H), 2.33 (dq, J=7.1, 5.9 Hz, 2H), 2.22 (dq, J=15.2, 7.6 Hz, 1H), 2.05-1.95 (m, 2H), 1.90-1.71 (m, 4H), 1.63-1.50 (m, 4H), 1.44 (p, J=7.1 Hz, 2H), 1.38-1.10 (m, 12H).

(10-((3-Bromopropyl)sulfonyl)decyl)cyclobutane (10). To a solution 9 (1.35 g, 3.40 mmol) in THF (25 mL) was added magnesium bromide etherate (2.2 g, 8.51 mmol) in diethyl ether (25 mL). The suspension was stirred for 16 hr at RT. The mixture was filtered and the solid was washed by $Et_2O$. The filtrate was evaporated and the residue was treated by water (50 mL) and EtOAc (2×60 mL). The EtOAc layer was washed by brine, dried over $Na_2SO_4$, and evaporated to afford 10 (1.26 g, 97%) as an off-white solid. $^1$H NMR (400 MHz, Chloroform-d) δ 3.56 (t, J=6.2 Hz, 2H), 3.17-3.11 (m, 2H), 3.01-2.95 (m, 2H), 2.45-2.38 (m, 2H), 2.23 (dt, J=15.5, 7.8 Hz, 1H), 2.06-1.95 (m, 2H), 1.90-1.74 (m, 4H), 1.61-1.53 (m, 4H), 1.43 (q, J=7.3 Hz, 2H), 1.38-1.10 (m, 12H).

4-Amino-1-(((5S)-2-(3-((10-cyclobutyldecyl)sulfonyl)propoxy)-2-oxido-1,4,2-dioxaphosphinan-5-yl)methyl)pyrimidin-2(1H)-one (11). To a suspension of cCDV-DCMC (cyclic cidofovir-dicyclohexylmorpholinocarboxamindine salt, prepared from cidofovir as described in *ANTIMICROBIAL AGENTS AND CHEMOTHERAPY*, (2002), p. 991-995) (0.250 g, 0.451 mmol) in dry DMF (10 mL) was added 10 (0.774 g, 2.03 mmol) and the mixture was stirred and heated at 80° C. for 16 hr. The reaction mixture was then concentrated in vacuo and the soft solid residue was dissolved in 5 ml of 9:1 DCM/MeOH mixed solvent and purified twice by silica gel preparative TLC plates (9:1 DCM/MeOH) to give 11 (50 mg, 19.8%) as a white solid. $^1$H NMR (400 MHz, Chloroform-d) δ 7.31-7.24 (m, 1H), 5.81 (dd, J=7.2, 2.4 Hz, 1H), 4.42 (dd, J=12.6, 4.7 Hz, 1H), 4.36-4.02 (m, 5H), 3.92 (t, J=14.2 Hz, 1H), 3.61 (ddd, J=14.3, 11.1, 7.4 Hz, 1H), 3.13 (dt, J=15.7, 7.6 Hz, 2H), 3.07-2.94 (m, 2H), 2.25 (dq, J=15.7, 7.8 Hz, 3H), 2.03 (dtd, J=11.2, 7.6, 3.0 Hz, 2H), 1.90-1.74 (m, 4H), 1.57 (dq, J=11.3, 8.9 Hz, 2H), 1.46 (t, J=7.3 Hz, 2H), 1.39-1.07 (m, 17H). $^{31}$P NMR (162 MHz, Chloroform-d) δ 12.63, 11.14. MS: m/z 562.2703 (M+H)$^+$. HPLC: 99.03%

Ammonium 3-((10-cyclobutyldecyl)sulfonyl)propyl hydrogen ((((S)-1-(4-amino-2-oxopyrimidin-1(2H)-yl)-3-hydroxypropan-2-yl)oxy)methyl)phosphonate (120). 11 (44 mg, 0.078 mmol) was put into a screw-cap reaction tube. Concentrated NH$_4$OH (28-30%, 5 mL) was added. The reaction tube was screw capped. The suspension mixture was then stirred at 80° C. for 16 h. The reaction mixture was then cooled to room temperature and evaporated under reduced pressure at 45° C. The soft solid residue was triturated with acetone, collected by filtration, washed by a small amount of acetone and DCM, and dried under vacuum to give 12 (43 mg, 92%) as a white solid. $^1$H NMR (500 MHz, Methanol-d4) δ 7.75 (d, J=7.4 Hz, 1H), 5.92 (d, J=7.3 Hz, 1H), 4.10 (dd, J=14.0, 3.3 Hz, 1H), 3.98 (q, J=6.2 Hz, 2H), 3.80 (dd, J=14.0, 7.7 Hz, 1H), 3.77-3.69 (m, 2H), 3.68-3.64 (m, 1H), 3.60 (dd, J=12.9, 9.3 Hz, 1H), 3.52 (dd, J=12.4, 4.1 Hz, 1H), 3.25-3.16 (m, 2H), 3.13-3.04 (m, 2H), 2.26 (p, J=7.8 Hz, 1H), 2.10-2.01 (m, 4H), 1.90-1.77 (m, 4H), 1.58 (dq, J=11.3, 8.8 Hz, 2H), 1.46 (q, J=7.5 Hz, 2H), 1.41-1.12 (m, 15H). $^{31}$P NMR (202 MHz, Methanol-d4) δ 16.16. MS: m/z 580.2816 (M+H)$^+$, 578. 2676 (M-H)$^-$. HPLC: 98.03%.

Example 2. Ammonium 3-((12-cyclobutyldodecyl)sulfonyl)propyl Hydrogen ((((S)-1-(4-amino-2-oxopyrimidin-1(2H)-yl)-3-hydroxypropan-2-yl)oxy)methyl)phosphonate (121)

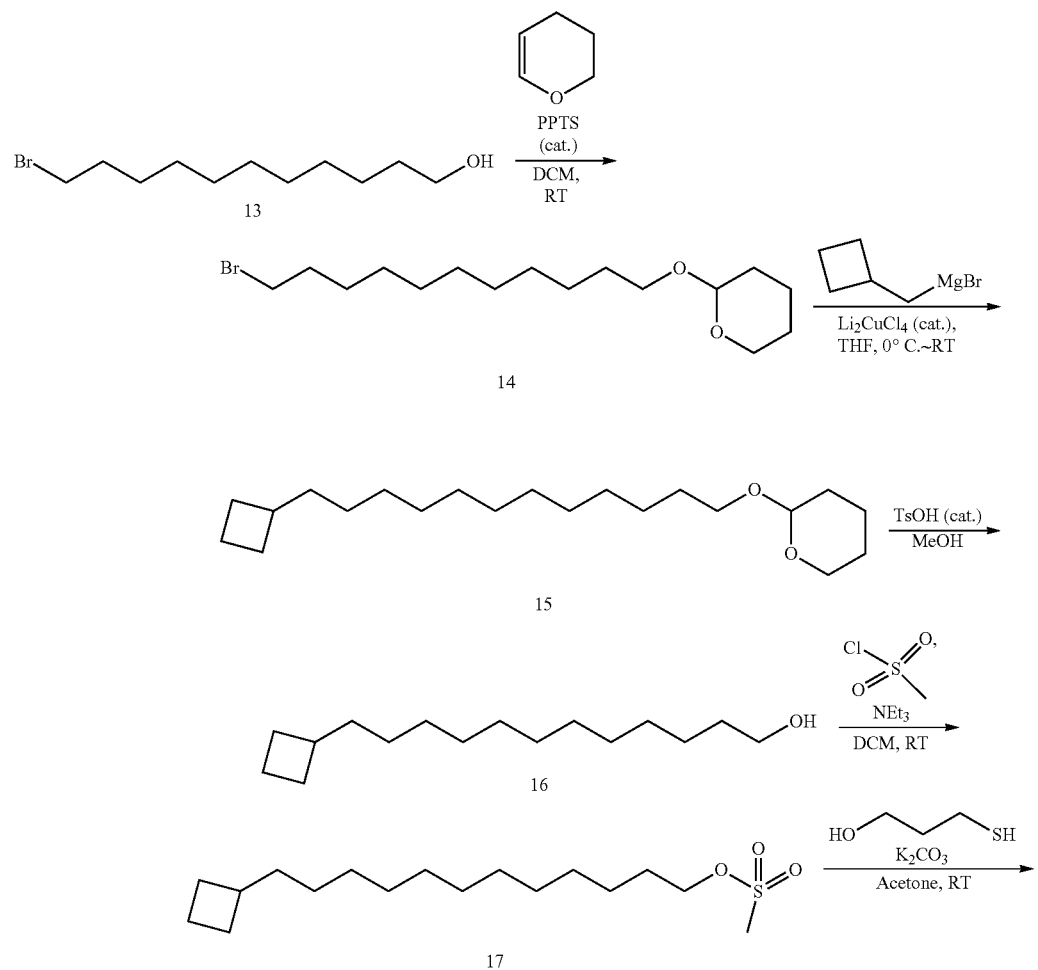

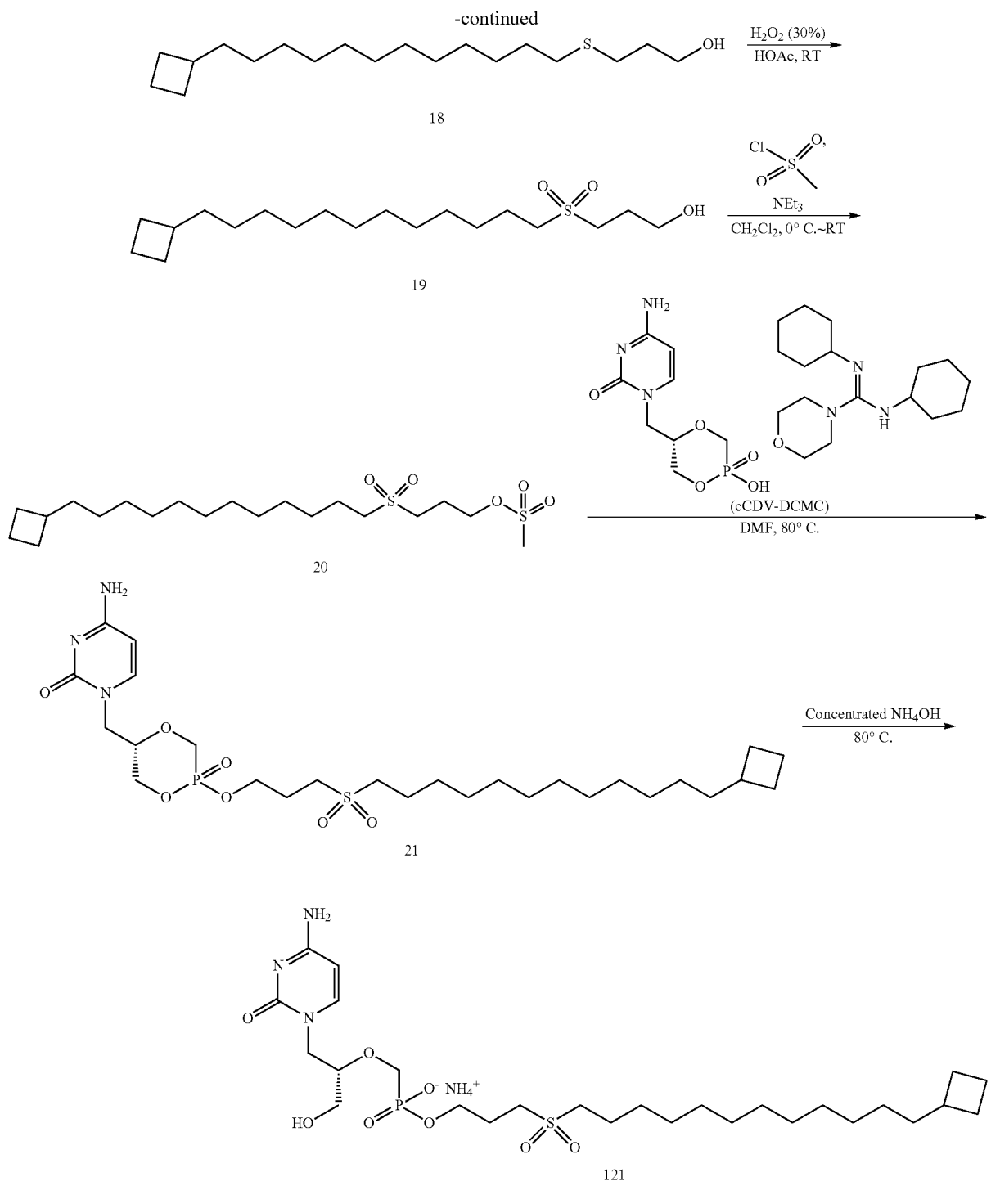

2-((11-Bromoundecyl)oxy)tetrahydro-2H-pyran (14). To a solution of 13 (20 g, 80 mmol) and 2,3-dihydro-2H-pyran (10.05 g, 119 mmol) in DCM (150 mL) was added pyridinium p-toluenesulfonate (PPTS) (3.0 g, 11.94 mmol) at RT. The mixture was stirred for 18 hr at RT. It was then concentrated. The residue was taken up into hexanes and purified by a silica gel column (5% EtOAc in hexanes) to give 14 (26.6 g, 100%) as colorless oil. $^1$H NMR (400 MHz, Chloroform-d) δ 4.58 (dd, J=4.5, 2.7 Hz, 1H), 3.87 (ddd, J=11.1, 7.3, 3.4 Hz, 1H), 3.73 (dt, J=9.5, 6.9 Hz, 1H), 3.55-3.46 (m, 1H), 3.45-3.33 (m, 3H), 1.91-1.77 (m, 3H), 1.72 (ddd, J=12.1, 7.7, 4.4 Hz, 1H), 1.64-1.47 (m, 7H), 1.45-1.25 (m, 13H).

2-((12-Cyclobutyldodecyl)oxy)tetrahydro-2H-pyran (15). To a mixed solution of 14 (3.5 g, 10.44 mmol) in THF (30 mL) and Li$_2$CuCl$_4$ (0.1 M solution in THF, 5.2 mL, 0.522 mmol) at 0° C. was added Grignard reagent cyclobutylmethyl)magnesium bromide which was made from (bromomethyl)cyclobutane (4.0 g, 26.8 mmol) and grinded magnesium turnings (1.31 g, 53.7 mmol) in Et$_2$O (25 mL). After the addition completed, stirred at 0° C. for 30 min and then at RT for 16 hr. The reaction was quenched by NH₄Cl at 0° C. Stirred at RT for 20 min. Then the mixture was treated with hexanes and water. Organic phase was washed by brine, dried over Na₂SO₄, and concentrated to give 15 (3.3 g, 97%) as a colorless oil. 1H NMR (400 MHz, Chloroform-d) δ 4.58 (dd, J=4.5, 2.7 Hz, 1H), 3.87 (ddd, J=11.1, 7.3, 3.4 Hz, 1H), 3.73 (dt, J=9.5, 6.9 Hz, 1H), 3.56-3.46 (m, 1H), 3.38 (dt, J=9.6, 6.7 Hz, 1H), 2.23 (hept, J=7.8 Hz, 1H), 2.01 (dddd, J=13.4, 6.7, 5.2, 3.0 Hz, 2H), 1.91-1.67 (m, 4H), 1.63-1.48 (m, 9H), 1.39-1.14 (m, 19H).

12-Cyclobutyldodecan-1-ol (16). p-Toluenesulphonic acid monohydrate (97 mg, 0.51 mmol) was added to a emulsion of 15 (3.3 g, 10.2 mmol) in methanol (20 ml) and the mixture was stirred at 32° C. for 20 hr. Most of the methanol was removed under reduced pressure. Water (20 mL) was added to the residue, and the mixture was extracted with hexane (3×20 mL). The combined organic layers were washed with saturated aqueous NaHCO₃ and brine, dried over Na₂SO₄, and concentrated under vacuum to give 16 (2.30 g, 94%) as colorless oil. ¹H NMR (400 MHz, Chloroform-d) δ 3.64 (t, J=6.7 Hz, 2H), 2.23 (hept, J=7.7 Hz, 11H), 2.07-1.96 (m, 2H), 180 (tddd, J=14.8, 11.4, 93, 6.3 Hz, 2H), 1.65-1.49 (m, 5H), 1.41-1.11 (m, 20H).

12-Cyclobutyldodecyl methanesulfonate (17). 16 (2.3 g, 9.57 mmol) and triethylamine (1.16 g, 11.48 mmol) were dissolved in DCM (20 mL) and cooled to 0° C. Methanesulfonyl chloride (1.32 g, 11.48 mmol in DCM (10 mL) was added dropwise to the above solution over 5 min. The reaction was stirred at RT for 3 hr, quenched with 0.5 N aq HCl and extracted three times with hexanes. The organic layer was then washed with water, NaHCO₃, brine, dried over sodium sulfate, filtered, and concentrated under reduced pressure to give 17 (2.91 g, 96%) as wax-like solid. ¹H NMR (400 MHz, Chloroform-d) δ 4.22 (t, J=6.6 Hz, 2H), 3.01 (s, 3H), 2.23 (hept, J=7.8 Hz, 1H), 2.06-1.95 (m, 2H), 1.90-1.69 (m, 4H), 1.63-1.49 (m, 3H), 1.47-1.11 (m, 19H), which were used in the next step without further purification.

3-((12-Cyclobutyldodecyl)thio)propan-1-ol (18). Under nitrogen, to a solution of 17 (2.9 g, 9.1 mmol) and 3-mercaptopropan-1-ol (1.26 g, 13.7 mmoL) in acetone (30 mL) was added potassium carbonate (2.52 g, 18.2 mmol). The suspension was stirred at 27° C. for 16 hr. The mixture was evaporated and the residue was partitioned between water and hexanes. The organic phase was washed with 1 N sodium hydroxide, water, brine, dried over sodium sulfate, and evaporated under reduced pressure to afford 18 (2.67 g, 93%) as a white solid. ¹H NMR (400 MHz, Chloroform-d) δ 3.76 (q, J=5.7 Hz, 2H), 2.63 (t, J=7.0 Hz, 2H), 2.56-2.48 (m, 2H), 2.21 (h, J=7.7 Hz, 1H), 2.07-1.94 (m, 2H), 1.90-1.66 (m, 5H), 1.64-1.51 (m, 5H), 1.38-1.15 (m, 19H).

3-((12-Cyclobutyldodecyl)sulfonyl)propan-1-ol (19). To a solution of 18 (2.6 g, 8.27 mmol) in AcOH (65 mL) was added 30% H₂O₂ (17 mL). The solution was stirred in the dark at RT for 16 hr. The solvent was evaporated under reduced pressure. The white solid residue was treated with DCM and sat. NaHCO₃. The organic phase was washed by brine, dried over Na₂SO₄, and evaporated to give 19 (2.80 g, 98%) as a white solid. ¹H NMR (400 MHz, Chloroform-d) δ 3.81 (q, J=5.3 Hz, 2H), 3.16-3.08 (m, 2H), 3.03-2.95 (m, 2H), 2.23 (p, J=7.8 Hz, 1H), 2.15-2.06 (m, 2H), 2.01 (dddd, J=15.2, 7.0, 5.2, 2.9 Hz, 2H), 1.91-1.72 (m, 4H), 1.64-1.49 (m, 4H), 1.48-1.09 (m, 19H).

3-((12-Cyclobutyldodecyl)sulfonyl)propyl methanesulfonate (20). 19 (2.8 g, 8.08 mmol) and triethylamine (0.98 g, 9.7 mmol) were added in DCM (40 mL) and cooled to 0° C. Methanesulfonyl chloride (1.1 g, 9.7 mmol) was added dropwise via syringe to the stirred solution over 2 min. The reaction was stirred at RT for 3 hr, quenched with 0.5 N aq HCl, and extracted 2 times with DCM. The organic layer was then washed with water, NaHCO₃, brine, dried over sodium sulfate, filtered, and concentrated under reduced pressure to afford 20 (3.15 g, 92%) as a white solid. ¹H NMR (400 MHz, Chloroform-d) δ 4.41 (t, J=5.9 Hz, 2H), 3.11 (t, J=7.4 Hz, 2H), 3.05 (s, 3H), 3.03-2.96 (m, 2H), 2.38-2.29 (m, 2H), 2.27-2.18 (m, 1H), 2.05-1.98 (m, 2H), 1.82 (dddd, J=21.6, 12.3, 7.6, 5.6 Hz, 4H), 1.59-1.50 (m, 4H), 1.49-1.40 (m, 2H), 1.36-1.15 (m, 16H).

4-Amino-1-(((5S)-2-(3-((12-cyclobutyldodecyl)sulfonyl) propoxy)-2-oxido-1,4,2-dioxaphosphinan-5-yl)methyl)pyrimidin-2(1H)-one (21). To a suspension of cCDV-DCMC (cyclic cidofovir-dicyclohexylmorpholinocarboxamindine salt, prepared from cidofovir as described in ANTIMICROBIAL AGENTS AND CHEMOTHERAPY, (2002), p. 991-995) (0.20 g, 0.36 mmol) in dry DMF (8 mL) was added 20 (0.383 g, 0.902 mmol). The mixture was stirred and heated at 80° C. for 20 hr. The reaction mixture was then concentrated in vacuo and the soft solid residue was dissolved in 9:1 DCM/MeOH mixed solvent and purified three times by silica gel preparative TLC plates (9:1 DCM/MeOH) to give 21 (0.081 g, 38%) as a white solid. ¹H NMR (400 MHz, Chloroform-d) δ 7.35-7.28 (m, 1H), 5.71 (t, J=7.4 Hz, 1H), 4.41 (dt, J=12.3, 3.3 Hz, 1H), 4.34-4.27 (m, 1H), 4.23-3.98 (m, 4H), 3.91-3.78 (m, 1H), 3.59 (ddd, J=39.2, 14.5, 7.7 Hz, 1H), 3.09 (dt, J=13.4, 7.7 Hz, 2H), 3.04-2.92 (m, 2H), 2.33-2.18 (m, 3H), 2.01 (dtd, J=11.4, 7.5, 2.8 Hz, 2H), 1.81 (dddd, J=16.6, 10.7, 8.1, 3.2 Hz, 6H), 1.57 (qd, J=8.8, 2.4 Hz, 2H), 1.43 (d, J=7.6 Hz, 2H), 1.29 (m, 19H). ³¹P NMR (162 MHz, Chloroform-d) δ 12.42, 10.84. MS: m/z 590.3020 (M+H)⁺, m/z 588.2906 (M−H)⁻. HPLC: 95.63%.

Ammonium 3-((12-cyclobutyldodecyl)sulfonyl)propyl hydrogen (((((S)-1-(4-amino-2-oxopyrimidin-1(2H)-yl)-3-hydroxypropan-2-yl)oxy)methyl)phosphonate (121). 21 (55 mg, 0.093 mmol) was put into a screw-cap reaction tube. Concentrated NH₄OH (28-30%, 6 mL) was added. The reaction tube was screw capped. The suspension mixture was then stirred at 80° C. for 18 h. The reaction mixture was then cooled to room temperature and evaporated under reduced pressure at 55° C. The soft solid residue was triturated with acetonoe, collected by filtration, washed by a small amount of acetone, and dried under vacuum to give 22 (50 mg, 86%) as a white solid. ¹H NMR (400 MHz, Methanol-d4) δ 7.81 (d, J=7.4 Hz, 1H), 5.95 (d, J=7.4 Hz, 1H), 4.13 (d, J=14.0 Hz, 1H), 3.99 (q, J=6.1 Hz, 2H), 3.88-3.48 (m, 7H), 3.21 (dd, J=9.7, 6.0 Hz, 2H), 3.14-3.06 (m, 2H), 2.26 (p, J=7.8 Hz, 1H), 2.09-1.97 (m, 4H), 1.81 (dq, J=16.2, 8.9, 7.8 Hz, 4H), 1.60 (d, J=9.6 Hz, 1H), 1.46 (d, J=7.4 Hz, 1H), 1.41-1.11 (m, 19H). ³¹P NMR (162 MHz, Methanol-d4) δ 16.15. MS: m/z 608.3124 (M+H)⁺, 606.2981 (M−H)⁻. HPLC: 95.57%.

Example 3. Ammonium 3-((13-cyclobutyltridecyl)sulfonyl)propyl Hydrogen ((((S)-1-(4-amino-2-oxopyrimidin-1(2H)-yl)-3-hydroxypropan-2-yl)oxy)methyl)phosphonate (122)
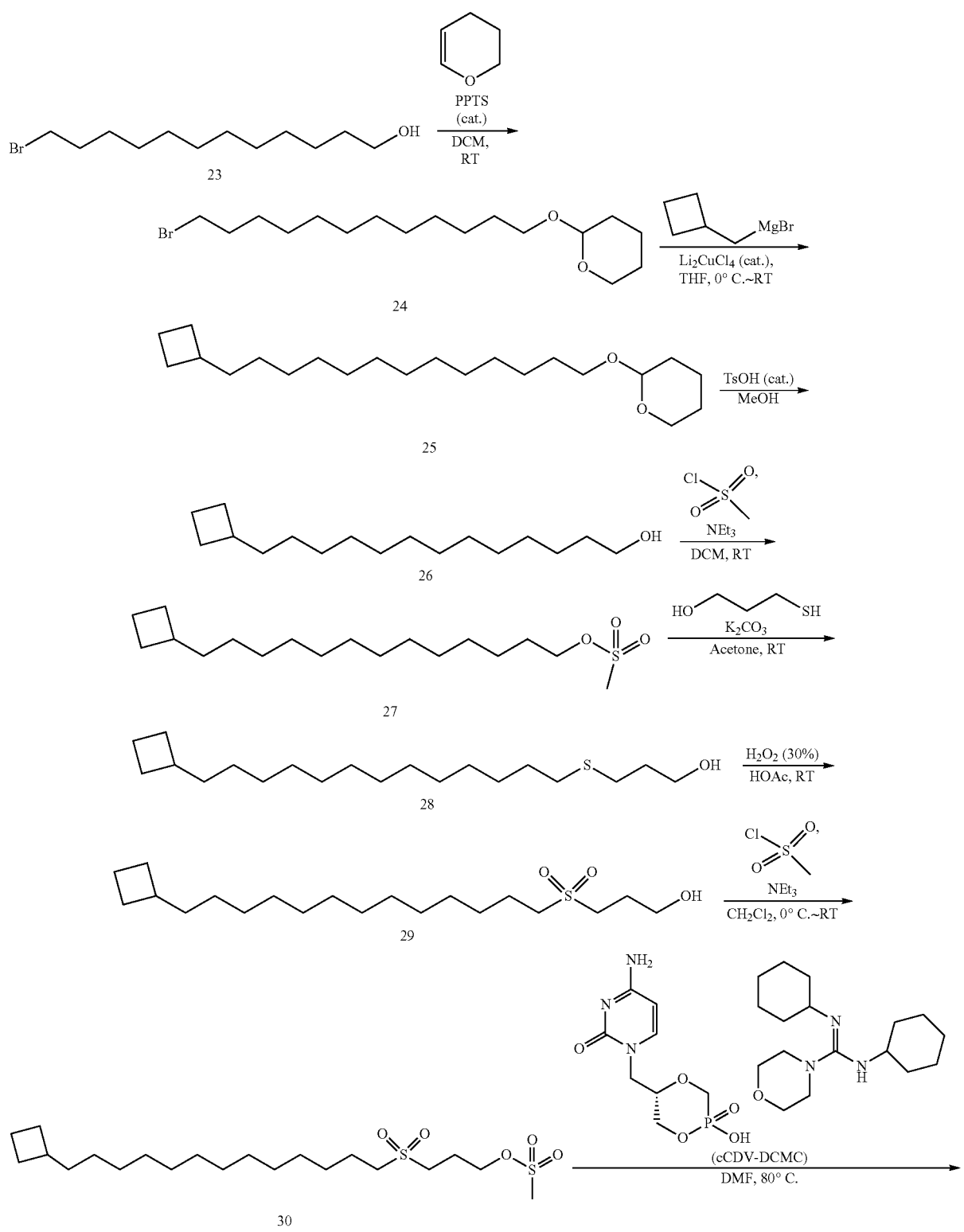

-continued

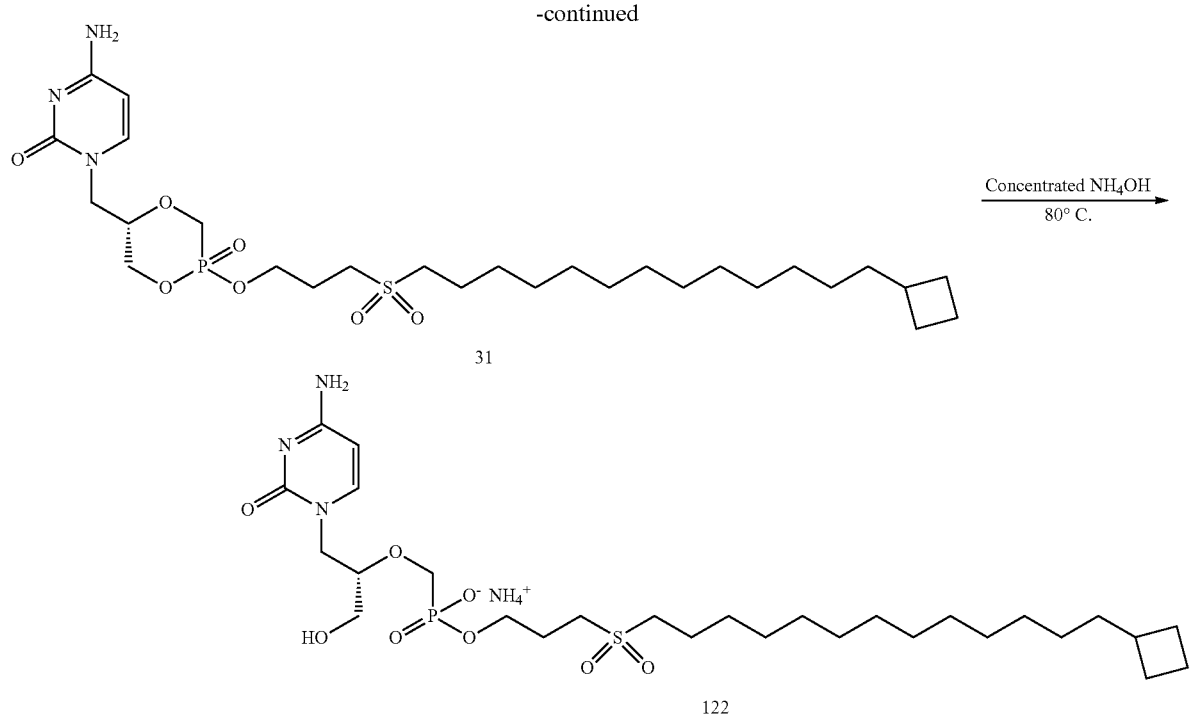

2-((12-Bromododecyl)oxy)tetrahydro-2H-pyran (24). To a solution of 23 (5.2 g, 19.61 mmol, commercial) and 2,3-dihydro-2H-pyran (2.47 g, 29.4 mmol) in DCM (35 mL) was added pyridinium p-toluenesulfonate (PPTS) (0.74 g, 2.94 mmol) at RT. The mixture was stirred for 18 hr at RT. The mixture was concentrated. The residue was taken up in hexanes and purified by a silica gel column (5% EtOAc in hexanes) to give 24 (6.8 g, 99%) as a colorless oil. $^1$H NMR (400 MHz, Chloroform-d) δ 4.58 (dd, J=4.5, 2.7 Hz, 1H), 3.87 (ddd, J=11.1, 7.4, 3.4 Hz, 1H), 3.73 (dt, J=9.5, 6.9 Hz, 1H), 3.55-3.47 (m, 1H), 3.45-3.33 (m, 3H), 1.90-1.78 (m, 3H), 1.76-1.68 (m, 1H), 1.64-1.47 (m, 6H), 1.46-1.23 (m, 16H).

2-((13-Cyclobutyltridecyl)oxy)tetrahydro-2H-pyran (25). To a mixed solution of 24 (3.64 g, 10.42 mmol) in THF (30 mL) and Li$_2$CuCl$_4$ (0.1 M solution in THF, 5.2 mL, 0.522 mmol) at 0° C. was added Grignard reagent cyclobutylmethyl)magnesium bromide which was made from (bromomethyl)cyclobutane (4.0 g, 26.8 mmol) and grinded magnesium turnings (1.31 g, 53.7 mmol) in Et$_2$O (25 mL). After the addition completed, stirred at 0° C. for 30 min and then at RT for 16 hr. The reaction was quenched by NH$_4$Cl at 0° C. Stirred at RT for 20 min. Then the mixture was treated with hexanes and water. Organic phase was washed by brine, dried over Na$_2$SO$_4$, and concentrated to give 25 (3.5 g, 99%) as a colorless oil. $^1$H NMR (400 MHz, Chloroform-d) δ 4.58 (dd, J=4.5, 2.7 Hz, 1H), 3.87 (ddd, J=11.0, 7.4, 3.4 Hz, 1H), 3.73 (dt, J=9.6, 6.9 Hz, 1H), 3.58-3.45 (m, 1H), 3.38 (dt, J=9.6, 6.7 Hz, 1H), 2.23 (dt, J=15.5, 7.8 Hz, 1H), 2.01 (dddd, J=13.6, 6.7, 5.2, 3.0 Hz, 2H), 1.91-1.66 (m, 4H), 1.62-1.49 (m, 9H), 1.40-1.11 (m, 21H).

13-Cyclobutyltridecan-1-ol (26). To an emulsion of 25 (3.45 g, 10.2 mmol) in Methanol (20 mL) was added p-toluenesulphonic acid monohydrate (97 mg, 0.51 mmol). The mixture was stirred at 40° C. for 48 hr. Most of the methanol was removed under reduced pressure. Water (20 mL) was added to the residue and the mixture was extracted with hexane (2×40 mL). The combined organic layers were washed with saturated aqueous NaHCO$_3$ and brine, dried over Na$_2$SO$_4$, and concentrated under reduced pressure to give 26 (2.42 g, 93%) as an wax-like solid. $^1$H NMR (400 MHz, Chloroform-d) δ 3.64 (t, J=6.6 Hz, 2H), 222 (h, J=7.8 Hz, 1H), 2.08-1.92 (m, 2H), 1.80 (tddd, J=14.8, 11.4, 9.3, 6.4 Hz, 2H), 1.57 (dtd, J=11.2, 7.4, 6.2, 2.3 Hz, 4H), 1.42-1.06 (m, 23H).

13-Cyclobutyltridecyl methanesulfonate (27). 26 (2.4 g, 9.43 mmol) and triethylamine (1.15 g, 11.32 mmol) were dissolved in DCM (30 mL) and the solution was cooled to 0° C. Methanesulfonyl chloride (1.30 g, 11.32 mmol) was added dropwise. The reaction was stirred at RT for 3 hr, quenched with 0.5 N aq HCl and extracted two times with hexanes. The organic layer was then washed with H$_2$O, NaHCO$_3$, brine, dried over sodium sulfate, filtered, and concentrated under reduced pressure to give 27 (3.0 g, 96%) as an wax-like solid. $^1$H NMR (400 MHz, Chloroform-d) δ 4.22 (t, J=6.6 Hz, 2H), 3.01 (s, 3H), 2.23 (p, J=7.8 Hz, 1H), 2.07-1.93 (m, 2H), 1.87-1.68 (m, 4H), 1.61-1.52 (m, 2H), 1.42-1.12 (m, 22H).

3-((13-Cyclobutyltridecyl)thio)propan-1-ol (28). Under nitrogen, to a solution of 27 (3.0 g, 9.02 mmol) and 3-mercaptopropan-1-ol (1.25 g, 13.53 mmoL) in acetone (30 mL) was added potassium carbonate (2.49 g, 18.04 mmol). The suspension was stirred at 30° C. for 16 hr. The mixture was evaporated and the residue was partitioned between water and hexane. The organic phase was washed with 1 N sodium hydroxide, water, brine, dried over sodium sulfate, and the volatiles was removed under vacuum to give 28 (2.9 g, 98%) as a white solid. $^1$H NMR (400 MHz, Chloroform-d) δ 3.77 (q, J=5.4 Hz, 2H), 2.64 (t, J=7.0 Hz, 2H), 2.53 (dd, J=8.1, 6.8 Hz, 2H), 2.28-2.19 (m, 1H), 2.07-1.95 (m, 2H), 1.92-1.72 (m, 4H), 1.65-1.48 (m, 5H), 1.47-1.07 (m, 22H).

3-((13-Cyclobutyltridecyl)sulfonyl)propan-1-ol (29). To a solution of 28 (2.85 g, 8.67 mmol) in AcOH (65 mL) was added 30% H$_2$O$_2$ (17.7 mL, 30%, 173 mmol). The solution was stirred in the dark at RT for 16 h. The solvent was evaporated under reduced pressure. The white solid residue was treated with DCM and sat. NaHCO$_3$. The organic phase was washed by brine, dried over Na$_2$SO$_4$, and evaporated to afford 29 (2.98 g, 95%) as a white solid. $^1$H NMR (400 MHz, Chloroform-d) δ 3.82 (d, J=5.6 Hz, 2H), 3.17-3.07 (m, 2H), 3.00 (d, J=8.2 Hz, 2H), 2.27-2.19 (m, 1H), 2.16-2.07 (m, 2H), 2.04-1.98 (m, 2H), 1.88-1.73 (m, 4H), 1.56-1.47 (m, 1H), 1.43 (q, J=7.3 Hz, 2H), 1.38-1.10 (m, 22H).

3-((13-Cyclobutyltridecyl)sulfonyl)propyl methanesulfonate (30). 29 (2.95 g, 8.18 mmol) and triethylamine (0.99 g, 9.82 mmol) were added in DCM (40 mL) and cooled to 0° C. Methanesulfonyl chloride (1.12 g, 9.82 mmol) was added dropwise via syringe to the stirred solution over 2 min. The reaction was stirred at RT for 3 hr, quenched with 0.5 N aq HCl, and extracted 2 times with DCM. The organic layer was then washed with H$_2$O, NaHCO$_3$, brine, dried over sodium sulfate, filtered, and concentrated under reduced pressure to give 30 (3.3 g, 92%) as a white solid. $^1$H NMR (400 MHz, Chloroform-d) δ 4.41 (t, J=5.9 Hz, 2H), 3.16-3.08 (m, 2H), 3.05 (s, 3H), 3.02-2.96 (m, 2H), 2.41-2.28 (m, 2H), 2.28-2.19 (m, 1H), 2.05-1.95 (m, 2H), 1.92-1.69 (m, 4H), 1.59-1.50 (m, 4H), 1.45 (d, J=7.3 Hz, 1H), 1.29 (d, J=35.3 Hz, 19H).

4-Amino-1-(((5S)-2-(3-((13-cyclobutyltridecyl)sulfonyl) propoxy)-2-oxido-1,4,2-dioxaphosphinan-5-yl)methyl)pyrimidin-2(1H)-one (31). To a suspension of cCDV-DCMC (cyclic cidofovir-dicyclohexylmorpholinocarboxamindine salt, prepared from cidofovir as described in *ANTIMICROBIAL AGENTS AND CHEMOTHERAPY*, (2002), p. 991-995) (0.270 g, 0.487 mmol) in dry DMF (10 mL) was added 30 (0.534 g, 1.22 mmol) and the mixture was stirred and heated at 80° C. for 16 hr. The reaction mixture was then concentrated in vacuo and the soft solid residue was dissolved in 6 ml of 9:1 DCM/MeOH mixed solvent and purified by silica gel preparative TLC plate (9:1 DCM/MeOH) to give 31 (0.147 g, 50%) as a white solid. $^1$H NMR (400 MHz, Chloroform-d) δ 7.28 (dd, J=7.3, 5.6 Hz, 1H), 5.97 (d, J=7.2 Hz, 1H), 4.39 (dd, J=11.5, 6.1 Hz, 1H), 4.33-4.11 (m, 2H), 4.09-4.03 (m, 1H), 3.89 (dd, J=14.8, 3.0 Hz, 1H), 3.77 (s, 2H), 3.45 (s, 2H), 3.15 (t, J=7.6 Hz, 1H), 3.07-2.96 (m, 2H), 2.25 (dt, J=15.4, 8.7 Hz, 2H), 2.01 (dt, J=9.7, 3.8 Hz, 1H), 1.91-1.76 (m, 9H), 1.64-1.49 (m, 3H), 1.43 (d, J=7.2 Hz, 1H), 1.37-1.15 (m, 20H). $^{31}$P NMR (162 MHz, Chloroform-d) δ 12.52, 11.12. MS: m/z 604.3185 (M+H)$^+$, m/z 602.3011 (M−H)$^-$.

Ammonium 3-((13-cyclobutyltridecyl)sulfonyl)propyl hydrogen ((((S)-1-(4-amino-2-oxopyrimidin-1(2H)-yl)-3-hydroxypropan-2-yl)oxy)methyl)phosphonate (122). 31 (0.135 g, 0.224 mmol) was put into a screw-cap reaction tube. Concentrated NH$_4$OH (28-30%, 15 mL) was added. The reaction tube was screw capped. The suspension mixture was then stirred at 80° C. for 18 h. The reaction mixture was then cooled to room temperature and evaporated under reduced pressure at 55° C. The soft solid residue was triturated with acetonoe, collected by filtration, washed by a small amount of acetone and DCM, and dried under vacuum to give 32 (76 mg, 53%) as white solid. $^1$H NMR (400 MHz, Methanol-d4) δ 7.82 (d, J=7.5 Hz, 1H), 5.95 (d, J=7.4 Hz, 1H), 4.13 (dd, J=14.0, 3.2 Hz, 1H), 3.99 (q, J=6.2 Hz, 2H), 3.88-3.48 (m, 6H), 3.21 (dd, J=9.6, 6.1 Hz, 2H), 3.16-3.04 (m, 2H), 2.24 (dt, J=16.6, 8.3 Hz, 1H), 2.14-1.97 (m, 5H), 1.96-1.72 (m, 3H), 1.60 (qd, J=8.8, 2.5 Hz, 2H), 1.46 (q, J=7.3 Hz, 2H), 1.40-1.09 (m, 20H). $^{31}$P NMR (162 MHz, Methanol-d4) δ 16.13. MS: m/z 622.3294 (M+H)$^+$, 620.3132 (M−H)$^-$. HPLC: 97.57%.

Example 4. Ammonium 3-((12-(3-methyloxetan-3-yl)dodecyl)sulfonyl)propyl Hydrogen ((((S)-1-(4-amino-6-oxopyrimidin-1(6H)-yl)-3-hydroxypropan-2-yl)oxy)methyl)phosphonate (110)

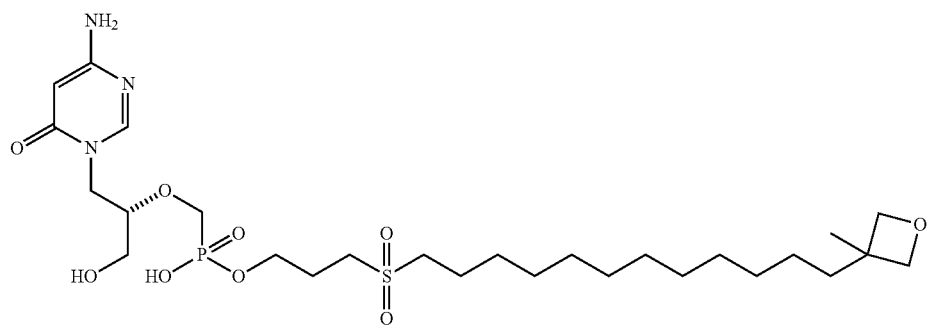

110

(11-hydroxyundecyl)triphenylphosphonium Bromide

To a solution of 11-bromoundecan-1-ol (5.0 g, 20 mmol) in acetonitrile (100 mL) was added triphenylphosphine (7.8 g, 30 mmol). The reaction was heated to 80° C. and left overnight. Additional triphenylphosphine (2 g, 7.6 mmol) was added and the reaction stirred overnight again at 80° C. The reaction was cooled to room temperature, filtered, and concentrated. The reaction mixture was partitioned between toluene and 1:1 methanol/water. The aqueous layer was washed with another portion of toluene, then with a portion of hexanes. The aqueous layer was concentrated to give the title compound as a clear colorless gum (10 g, 97%) shown below.

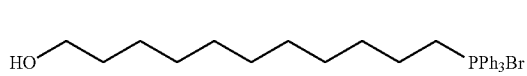

32

(Z)-12-(3-methyloxetan-3-yl)dodec-11-en-1-ol

To (11-hydroxyundecyl)triphenylphosphonium bromide (3.1 g, 6.0 mmol) in dioxane (20 mL) was added potassium carbonate (1.7 g, 12 mmol), water (90 uL, 5.0 mmol), and 3-methyloxetane-3-carbaldehyde (500 mg, 5.0 mmol). The reaction was heated to reflux and stirred for 4 h. The reaction was cooled to room temperature, diluted with dichloromethane and washed with water and brine. The organic layer was dried over magnesium sulfate, filtered, and concentrated. The crude residue was purified by column chromatography eluting with 20-30% ethyl acetate in hexanes to afford the title compound as a colorless oil (760 mg, 60%) shown below.

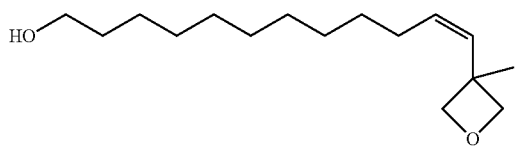

33

12-(3-methyloxetan-3-yl)dodecan-1-ol

10% palladium on carbon (catalytic) was added to a solution of (Z)-12-(3-methyloxetan-3-yl)dodec-11-en-1-ol (1.5 g, 6.0 mmol) in ethanol (50 mL). The flask was evacuated and filled with hydrogen gas by balloon. The reaction stirred overnight. The reaction mixture was evacuated and backfilled with nitrogen gas, then filtered over celite and concentrated to give the title compound as a colorless oil (1.5 g, 98%) shown below.

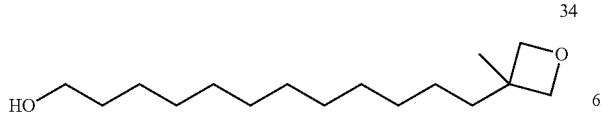

34

12-(3-methyloxetan-3-yl)dodecyl 4-methylbenzenesulfonate

To a solution of 12-(3-methyloxetan-3-yl)dodecan-1-ol (1.5 g, 5.9 mmol) in dichloromethane (30 mL) was added triethylamine (1.6 mL, 12 mmol) followed by TsCl (1.7 g, 8.9 mmol). The reaction stirred at room temperature overnight. The reaction was poured into dichloromethane and washed with water and brine. The organic layer was dried over magnesium sulfate, filtered, and concentrated. The crude residue was purified by column chromatography eluting with 0-20% ethyl acetate in hexanes to afford the title compound as a colorless oil (1.9 g, 79%) shown below.

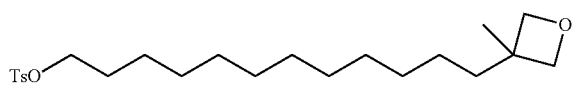

35

3-((12-(3-methyloxetan-3-yl)dodecyl)thio)propan-1-ol

To a solution of 3-mercaptopropan-1-ol (520 uL, 6.0 mmol) in ethanol (15 mL) was added potassium hydroxide (310 mg, 5.6 mmol). After 25 min, 12-(3-methyloxetan-3-yl)dodecyl 4-methylbenzenesulfonate (1.9 g, 4.6 mmol) as a solution in ethanol (20 mL) was added. After 3 h, additional 3-mercaptopropan-1-ol (520 uL, 6.0 mmol) followed by potassium hydroxide (310 mg, 5.6 mmol) was added. 2 h later, the reaction was concentrated, dissolved in ethyl acetate, and washed with 1N HCl, water, and brine. The organic layer was dried over magnesium sulfate, filtered and concentrated to afford the title compound as a clear colorless oil (1.4 g, 90%).

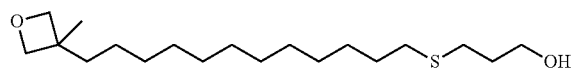

36

3-((12-(3-methyloxetan-3-yl)dodecyl)sulfonyl)propan-1-ol

To a solution of 3-((12-(3-methyloxetan-3-yl)dodecyl)thio)propan-1-ol (1.3 g, 3.9 mmol) in methanol (20 mL) was added a solution of Oxone (7.2 g, 12 mmol) in water (25 mL). The reaction stirred at room temperature for 2 h. The reaction mixture was partitioned between dichloromethane and water. The aqueous layer was extracted twice more with dichloromethane. The combined organic layers were washed with brine, dried over magnesium sulfate, filtered, and concentrated to give the title compound as a white solid (1.2 g, 82%) shown below.

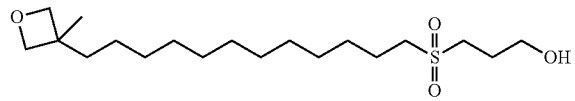

37

3-(12-((3-bromopropyl)sulfonyl)dodecyl)-3-methyl-oxetane

To a solution of 3-((12-(3-methyloxetan-3-yl)sulfonyl)propan-1-ol (1.2 g, 3.2 mmol) in dichloromethane (30 mL) was added triphenylphosphine (1.7 g, 6.4 mmol) followed by perbromomethane (1.6 g, 4.8 mmol). The reaction stirred at room temperature for 2 h. The reaction was concentrated then purified by flash column chromatography eluting with 20-30% ethyl acetate in hexanes to give the title compound as a white solid (900 mg, 65%) shown below.

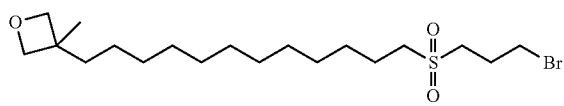

38

4-amino-1-(((5S)-2-(3-((12-(3-methyloxetan-3-yl)dodecyl)sulfonyl)propoxy)-2-oxido-1,4,2-dioxaphosphinan-5-yl)methyl)pyrimidin-2(1H)-one To a suspension of cCDV-DCMC (cyclic cidofovir-dicyclohexylmorpholinocarboxamindine salt, prepared from cidofovir as described in *ANTIMICROBIAL AGENTS AND CHEMOTHERAPY*, (2002), p. 991-995)(300 mg, 0.54 mmol) in DMF (10 mL) was added 3-(12-((3-bromopropyl)sulfonyl)dodecyl)-3-methyloxetane (230 mg, 0.54 mmol). The reaction was heated to 80° C. and stirred for 6.5 h. The reaction was cooled to room temperature and stirred overnight, concentrated and purified by column chromatography eluting with 0-10% methanol in dichloromethane to afford the title compound 110 (160 mg, 49%).

Example 5. Ammonium 3-((14-cyclobutyltetradecyl)sulfonyl)propyl (S)-(((1-(4-amino-2-oxopyrimidin-1(2H)-yl)-3-hydroxypropan-2-yl)oxy)methyl)phosphonate (105)

Scheme 5

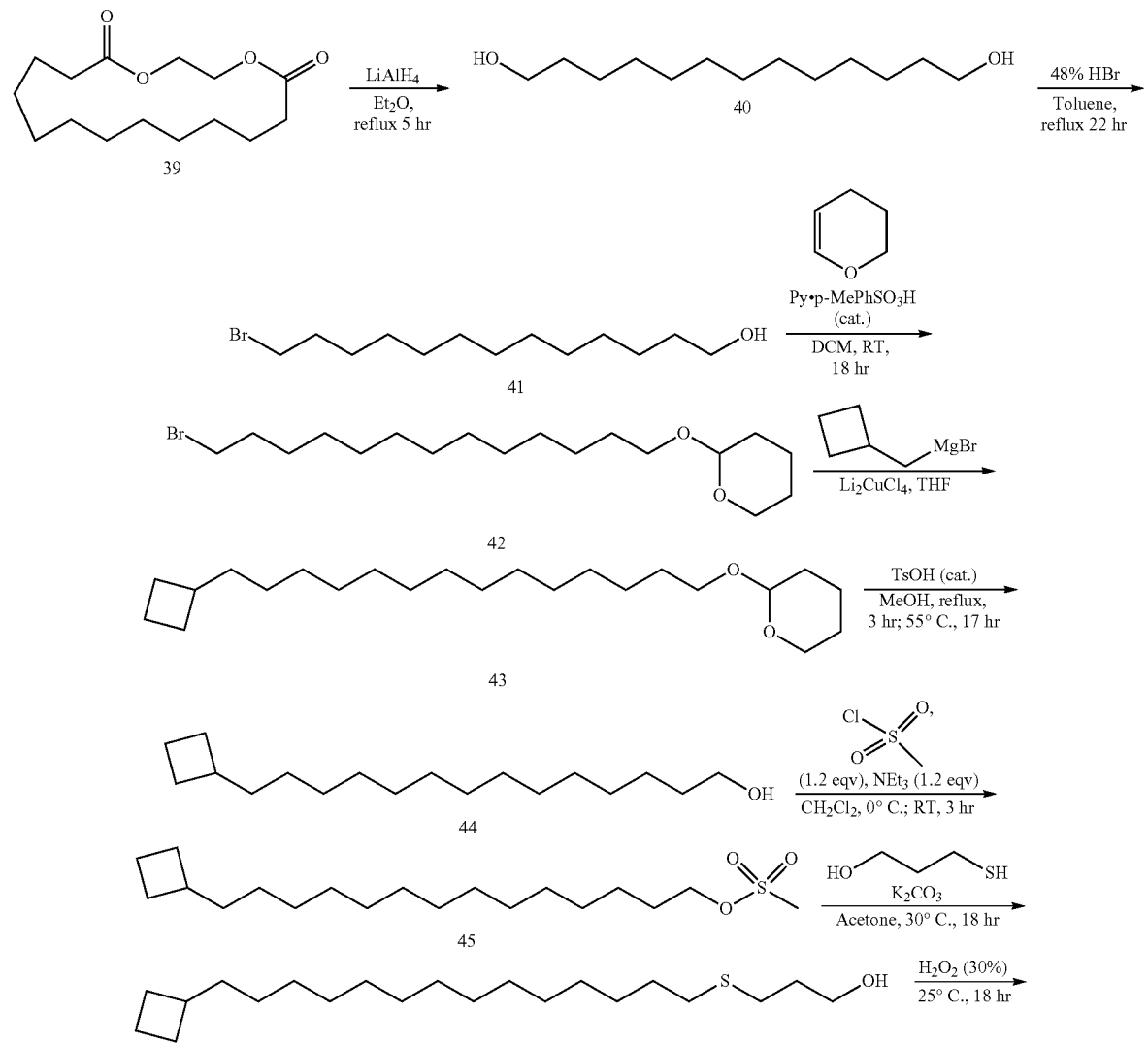

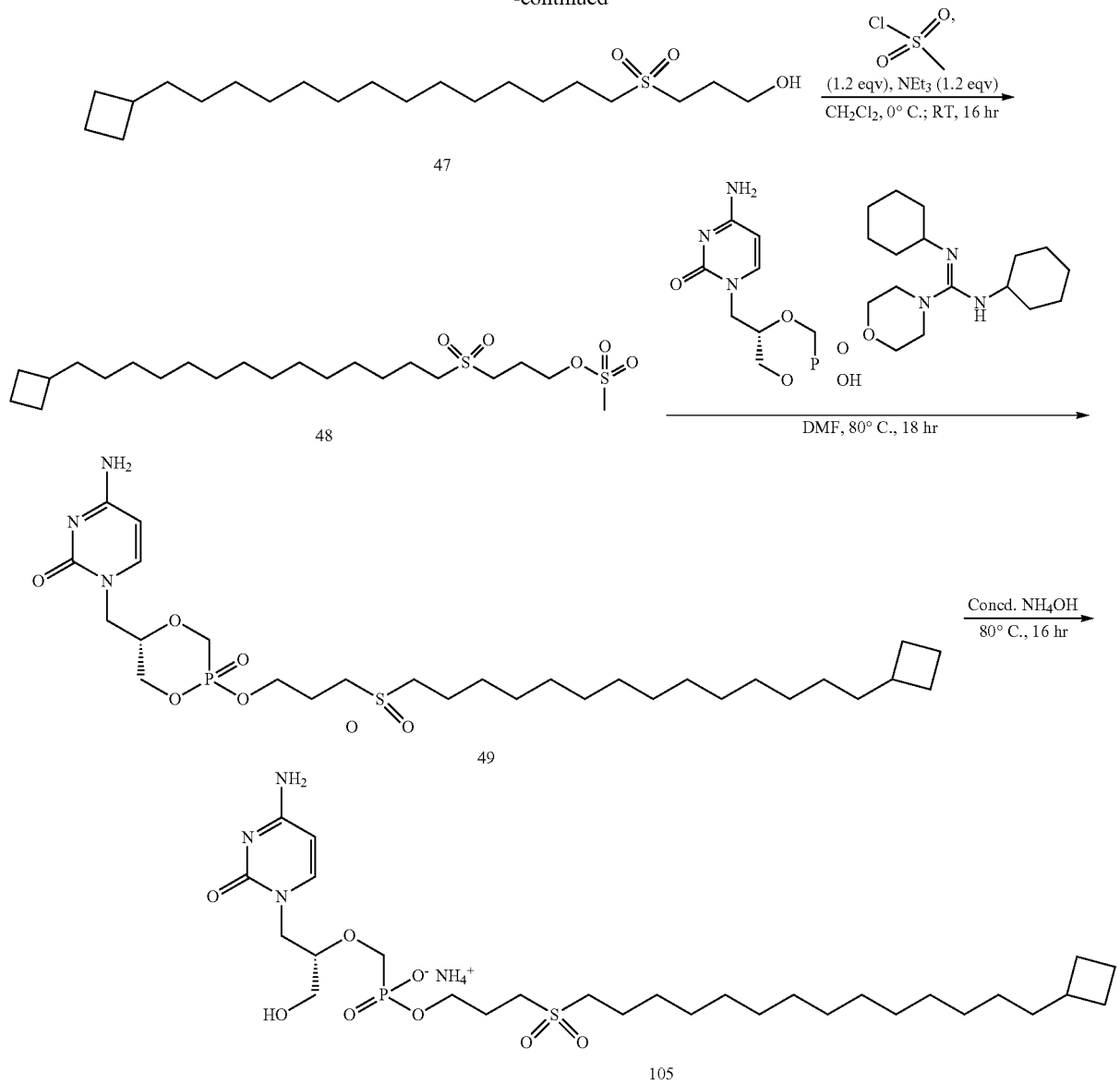

Tridecane-1,13-diol (40). To a suspension of LiAlH$_4$ (33.5 mL, 2 M in THF, 67.0 mmol) in Et$_2$O (50 mL) at 0° C. was slowly added 1,4-dioxacycloheptadecane-5,17-dione (39) (8.25 g, 30.5 mmol) in Et$_2$O (100 mL) via addition funnel. Then the mixture was warmed to RT and refluxed for 5 hr and then standed at RT overnight. After being cooled to 0° C. the reaction was quenched by slowly dropwise adding water (~10 mL) until almost no no bubbles released. Then the mixture was acidified by 4 N HCl (60 mL) and water (40 mL) to pH~6 and extracted by Et$_2$O (2×200 mL). The organic phase was washed by brine, dried over Na$_2$SO$_4$, and evaporated to afford 2 (5.0 g, 76%) as a white solid. $^1$H NMR (400 MHz, Chloroform-d) δ 3.64 (t, J=6.7 Hz, 4H), 1.61-1.48 (m, 4H), 1.40-1.22 (m, 20H).

13-Bromotridecan-1-ol (41). To a suspension of 40 (5.0 g, 23.1 mmol) in toluene (130 mL) was added HBr (48% aq., 2.9 mL, 25.4 mmol). The mixture was refluxed for 17 hr, while trapping the water by using a Dean-Stark trap. An aliquot was taken and evaporated to dryness. NMR showed it still contained 40. Additional HBr (48% aq., 8.1 mL, 71 mmol) and toluene (60 mL) were added and continued to reflux for additional 5 hr, trapping the water by using a Dean-Stark trap. Stop the reaction. The reaction mixture was evaporated to dryness to leave the crude product 41 (6.3 g, 98%) as off-white solid. $^1$H NMR (500 MHz, Chloroform-d) δ 3.64 (t, J=6.6 Hz, 2H), 3.41 (t, J=6.9 Hz, 2H), 1.85 (dt, J=14.5, 7.0 Hz, 2H), 1.66-1.49 (m, 2H), 1.49-1.17 (m, 19H).

2-((13-Bromotridecyl)oxy)tetrahydro-2H-pyran (42). To a suspension of 41 (6.3 g, 22.2 mmol) and 2,3-dihydro-2H-pyran (3.80 g, 45.1 mmol) in DCM (80 mL) was added pyridinium p-toluenesulfonate (0.567 g, 2.26 mmol) at RT. The mixture turned into a solution and was stirred at RT for 18 hr. The reaction mixture was concentrated to remove DCM. The residue was treated with hexanes and water. The hexanes phase was washed by brine, dried over Na$_2$SO$_4$, and evaporated to afford 42 (8.8 g, 99%) as an oil. $^1$H NMR (400 MHz, Chloroform-d) δ 4.60-4.56 (m, 1H), 3.89-3.85 (m, 1H), 3.75-3.70 (m, 1H), 3.50 (dd, J=7.7, 3.6 Hz, 1H), 3.42-3.36 (m, 3H), 1.89-1.81 (m, 3H), 1.71 (dd, J=7.7, 4.3 Hz, 1H), 1.60-1.53 (m, 8H), 1.44-1.18 (m, 16H).

2-((14-Cyclobutyltetradecyl)oxy)tetrahydro-2H-pyran (43). To a mixed solution of 42 (4.1 g, 11.3 mmol) in THF (30 mL) and Li$_2$CuCl$_4$ (0.1 M solution in THF, 5.6 mL, 0.56 mmol) at 0° C. was added Grignard reagent cyclobutylmethyl)magnesium bromide which was made from (bromomethyl)cyclobutane (4.2 g, 28.2 mmol) and grinded magnesium turnings (1.37 g, 56.4 mmol) in Et$_2$O (25 mL). After the addition completed, stirred at 0° C. for 30 min and then at RT for 18 hr. The reaction was quenched by NH$_4$Cl at 0° C. Stirred at RT for 20 min. Then the mixture was treated with hexanes and water. Organic phase was washed by brine, dried over Na$_2$SO$_4$, and concentrated to give 43 (3.9 g, 98%) as a colorless oil. $^1$H NMR (400 MHz, Chloroform-d) δ 4.58 (dd, J=4.5, 2.7 Hz, 1H), 3.87 (ddd, J=11.0, 7.4, 3.4 Hz, 1H), 3.73 (dt, J=9.6, 6.9 Hz, 1H), 3.55-3.45 (m, 1H), 3.38 (dt, J=9.6, 6.7 Hz, 1H), 2.22 (h, J=7.8 Hz, 1H), 2.09-1.93 (m, 2H), 1.91-1.66 (m, 4H), 1.66-1.44 (m, 9H), 1.44-1.08 (m, 23H).

14-Cyclobutyltetradecan-1-ol (44). p-Toluenesulphonic acid monohydrate (105 mg, 0.553 mmol) was added to a emulsion of 43 (3.90 g, 11.1 mmol) in methanol (40 ml) and the mixture was refluxed for 3 hr. Most of the methanol was removed under reduced pressure, water (20 ml) and saturated aqueous NaHCO$_3$ (10 ml) were added to the residue, and the mixture was extracted with hexane (3×20 ml). The combined organic layers were washed with brine, dried over Na$_2$SO$_4$, and concentrated under vacuum to give 3.3 g of off-white solid. NMR indicated it contained 17% of starting material. The solid was dissolved in 40 ml MeOH again. The reaction was repeated with p-Toluenesulphonic acid monohydrate (105 mg, 0.553 mmol) and stirred at 55° C. for 17 hr. Most of the methanol was removed under reduced pressure, water (20 ml) was added to the residue, and the mixture was extracted with hexane (3×20 ml). The combined organic layers were washed with saturated aqueous NaHCO$_3$ and brine, dried over Na$_2$SO$_4$, and concentrated under vacuum to give 44 (2.8 g, 94%) as colorless oil. $^1$H NMR (400 MHz, Chloroform-d) δ 3.65 (d, J=6.7 Hz, 2H), 2.22 (h, J=7.8 Hz, 1H), 2.01 (tdd, J=11.3, 7.6, 2.9 Hz, 2H), 1.90-1.69 (m, 2H), 1.63-1.47 (m, 4H), 1.34-1.21 (m, 25H).

14-Cyclobutyltetradecyl methanesulfonate (45). 44 (2.8 g, 10.4 mmol) and triethylamine (1.42 g, 14.1 mmol) were dissolved in DCM (40 mL) and cooled to 0° C. Methanesulfonyl chloride (1.61 g, 14.1 mmol) was added dropwise to the stirred solution over 1 min. The reaction was stirred at RT for 3 hr, quenched with 0.5 N aq HCl and extracted three times with hexanes. The organic layer was then washed with water, NaHCO$_3$, brine, dried over sodium sulfate, filtered, and concentrated under reduced pressure to give 45 (3.45 g, 95%) as an wax-like soft solid. $^1$H NMR (400 MHz, Chloroform-d) δ 4.22 (t, J=6.6 Hz, 2H), 3.01 (s, 3H), 2.23 (p, J=7.8 Hz, 1H), 2.08-1.96 (m, 2H), 1.89-1.68 (m, 4H), 1.64-1.49 (m, 2H), 1.49-1.09 (m, 24H).

3-((14-Cyclobutyltetradecyl)thio)propan-1-ol (46). Under nitrogen, to a solution of 45 (3.45 g, 9.95 mmol) and 3-mercaptopropan-1-ol (1.83 g, 19.9 mmoL) in acetone (50 mL) was added potassium carbonate (3.44 g, 24.9 mmol) The suspension was at 30° C. for 18 hr. TLC showed the SM consumed. The mixture was evaporated and the residue was partitioned between water and Et$_2$O. The organic phase was washed with 1 N sodium hydroxide, water, brine, dried over sodium sulfate, and evaporated under vacuum to give 46 (3.30 g, 97%) as an oil. $^1$H NMR (400 MHz, Chloroform-d) δ 3.76 (t, J=6.0 Hz, 2H), 2.64 (t, J=7.0 Hz, 2H), 2.53 (t, J=7.4 Hz, 2H), 2.30-2.13 (m, 1H), 2.10-1.90 (m, 2H), 1.90-1.65 (m, 6H), 1.62-1.47 (m, 4H), 1.43-1.10 (m, 23H).

3-((14-Cyclobutyltetradecyl)sulfonyl)propan-1-ol (47). To a solution of 46 (3.30 g, 9.63 mmol) in AcOH (85 mL) was added 30% H$_2$O$_2$ (19.7 ml, 193 mmol). The solution was stirred at RT for 18 hr. Evaporation of the solvent under reduced pressure to leave a white solid. The solid was washed with Et$_2$O and dried under vacuum to give the first batch of 9 (2.83 g) as a white solid. Some white solid was precipitated from the Et$_2$O filtrate and it was collected by filtration and dried under vacuum to give the second of 47 (0.23 g) as white solid. Total yield 85%. H NMR (400 MHz, Chloroform-d) δ 3.82 (t, J=5.9 Hz, 2H), 3.17-3.09 (m, 2H), 3.03-2.94 (m, 2H), 2.22 (dq, J=14.4, 7.2, 6.6 Hz, 1H), 2.15-2.06 (m, 2H), 2.01 (dddd, J=15.3, 7.0, 5.2, 2.9 Hz, 2H), 1.90-1.66 (m, 7H), 1.57 (qd, J=8.7, 2.4 Hz, 2H), 1.43 (q, J=7.3 Hz, 2H), 1.37-1.11 (m, 20H).

3-((14-Cyclobutyltetradecyl)sulfonyl)propyl methanesulfonate (48). A suspension mixture of 47 (3.0 g, 8.01 mmol) and triethylamine (1.30 g, 12.8 mmol) in DCM (120 mL) was cooled to 0° C. Methanesulfonyl chloride (1.47 g, 12.8 mmol) was added dropwise via syringe to the stirred mixture over 1 min. The reaction was stirred at RT for 16 hr. The reaction mixture was purified by a silica gel column (2.0% MeOH in DCM) to offer 48 (0.87 g, 24%) as a white solid. $^1$H NMR (400 MHz, Chloroform-d) δ 4.41 (t, J=5.9 Hz, 2H), 3.11 (t, J=7.4 Hz, 2H), 3.05 (s, 3H), 3.02-2.96 (m, 2H), 2.37-2.29 (m, 2H), 2.27-2.18 (m, 1H), 2.01 (dtd, J=11.5, 7.6, 7.1, 3.0 Hz, 2H), 1.82 (dddd, J=19.8, 12.5, 10.2, 7.9 Hz, 5H), 1.56 (dq, J=11.4, 8.9 Hz, 3H), 1.44 (p, J=7.2 Hz, 2H), 1.38-1.06 (m, 20H). $^{13}$C NMR (101 MHz, Chloroform-d) δ 67.54, 53.55, 48.41, 37.47, 37.45, 37.09, 36.20, 29.71, 29.69, 29.66, 29.64, 29.58, 29.50, 29.26, 29.05, 28.45, 28.41 (2C), 27.18, 21.97, 21.95, 18.49.

4-Amino-1-(((5S)-2-(3-((14-cyclobutyltetradecyl)sulfonyl)propoxy)-2-oxido-1,4,2-dioxaphosphinan-5-yl)methyl) pyrimidin-2(1H)-one (49). To a suspension of cCDV-DCMC (cyclic cidofovir-dicyclohexylmorpholinocarboxamindine salt, prepared from cidofovir as described in *ANTIMICROBIAL AGENTS AND CHEMOTHERAPY*, (2002), p. 991-995) (0.41 g, 0.74 mmol) in dry DMF (20 mL) was added 48 (0.836 g, 1.85 mmol) and the mixture was stirred and heated at 80° C. for 18 hr. The reaction mixture was concentrated in vacuo and the soft solid residue was dissolved in 10 ml of a mixed solvent (DCM/MeOH 90:12) and purified by two silica preparative-TLC plates (20 cm×20 cm, 2000 um, 90:12 DCM/MeOH) to give 49 (0.35 g, 77%) as a white waxy solid. $^1$H NMR (400 MHz, Chloroform-d) δ 7.29 (d, J=2.9 Hz, 1H), 5.79 (dd, J=7.2, 4.7 Hz, 1H), 4.49-4.36 (m, 1H), 4.35-4.00 (m, 5H), 3.96-3.83 (m, 1H), 3.79 (t, J=4.6 Hz, 3H), 3.64 (s, 4H), 3.10 (dt, J=15.5, 7.6 Hz, 2H), 3.04-2.94 (m, 2H), 2.28-2.21 (m, 2H), 2.00 (ddt, J=11.3, 7.1, 3.6 Hz, 2H), 1.86-1.80 (m, 5H), 1.56 (dd, J=6.5, 1.6 Hz, 4H), 1.25-1.08 (m, 19H). $^{31}$P NMR (162 MHz, Chloroform-d) δ 12.43, 10.88. MS: m/z 618.3336 (M+H)$^+$, 616.3210 (M−H)$^−$.

Ammonium 3-((14-cyclobutyltetradecyl)sulfonyl)propyl (S)-(((1-(4-amino-2-oxopyrimidin-1(2H)-yl)-3-hydroxypropan-2-yl)oxy)methyl)phosphonate (105). 49 (0.35 g, 0.567 mmol) was put into a screw-cap reaction tube. Concentrated NH$_4$OH (28-30%, 20 mL) was added. The reaction tube was screw capped. The suspension mixture was then stirred at 80° C. for 16 h. The reaction mixture was then cooled to room temperature and evaporated under reduced pressure at 45° C. The soft solid residue was triturated with acetonoe, collected by filtration, washed by acetone, and dried under vacuum to give 123 (189 mg, 51%) as a white solid. $^1$H NMR (400 MHz, Methanol-d4) δ 7.81 (d, J=7.4 Hz, 1H), 5.95 (d, J=7.4 Hz, 1H), 4.13 (d, J=14.1 Hz, 1H), 3.99 (d, J=6.5 Hz, 2H), 3.86-3.50 (m, 6H), 3.21 (t, J=8.0 Hz, 2H), 3.09 (t, J=8.1 Hz, 2H), 2.34-2.15 (m, 1H), 2.05 (s, 4H), 1.92-1.72 (m, 4H), 1.65-1.52 (m, 2H), 1.46 (s, 2H), 1.28 (s, 22H). $^{31}$P NMR (162 MHz, Methanol-d4) δ 16.18. MS: m/z 636.3438 (M+H)$^+$, 634.3319 (M–H)$^-$. HPLC: 98.14%.

Example 6. Ethyl (bis(3-((7-(3-methyloxetan-3-yl)heptyl)sulfonyl)-propoxy)phosphoryl)formate (116)

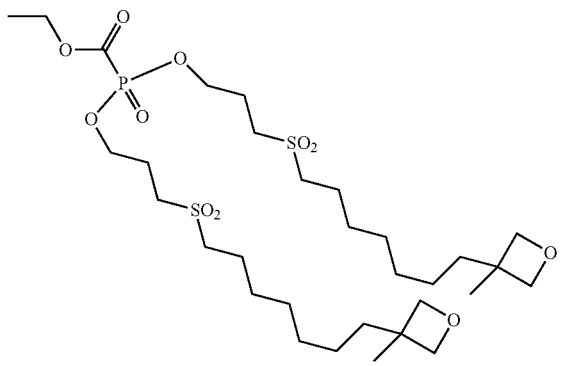

(E)-7-(3-methyloxetan-3-yl)hept-6-en-1-ol (50)

To a solution of 6-(bromotriphenyl-15-phosphaneyl)hexan-1-ol 50 (12.6 g, 28.4 mmol) in dioxane (23 mL) was added potassium carbonate (12.6 g, 90.9 mmol), water (0.050 g, 0.097 Eq, 2.77 mmol) and 3-methyloxetane-3-carbaldehyde (3.41 g, 1.2 Eq, 34.1 mmol). Heated to reflux for 18 hours. Cooled and concentrated. Purified residue by flash chromatography (EtOAc/hexane). Isco Combiflash (EtOAc/Hexane eluent). Obtained (E)-7-(3-methyloxetan-3-yl)hept-6-en-1-ol (2.5 g, 48%) shown below.

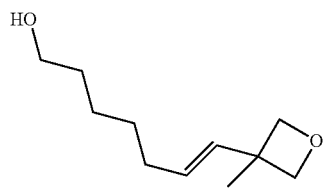

(E)-3-(7-bromohept-1-en-1-yl)-3-methyloxetane (52)

To a solution of (E)-7-(3-methyloxetan-3-yl)hept-6-en-1-ol 51 (2.5 g, 14 mmol) in CH$_2$C2 (15 mL) was added perbromomethane (5.4 g, 1.2 Eq, 16 mmol) followed by triphenylphosphane (4.3 g, 16 mmol). The resulting mixture was stirred 18 hours. Diluted with CH$_2$C2 and washed with satd. NaCl solution 2x. Dried, MgSO$_4$, filtered and concentrated. Purified by flash chromatography (EtOAc/hexane). Obtained (E)-3-(7-bromohept-1-en-1-yl)-3-methyloxetane (2.9 g, 86%) Oil shown below.

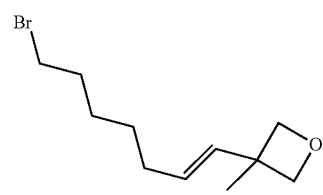

(E)-3-((7-(3-methyloxetan-3-yl)hept-6-en-1-yl)thio)propan-1-ol (53)

To a solution of (E)-3-(7-bromohept-1-en-1-yl)-3-methyloxetane 52 (2.1 g, 8.5 mmol) in EtOH (7 mL) was added 1.0 N NaOH (0.44 g, 11 mmol). The resulting mixture was stirred 15 minutes before adding 3-mercaptopropan-1-ol (1.0 g, 11 mmol). The resulting mixture was stirred 18 hours at room temperature. Concentrated. Diluted with ether and washed with 2 M HCl. extracted aqueous again with EtOAc. Combined organic layers and washed with satd. NaCl and dried (MgSO$_4$). Purified by flash chromatography. (10% EtOAc/hexane) Vizualize with iodine. Obtained (E)-3-((7-(3-methyloxetan-3-yl)hept-6-en-1-yl)thio)propan-1-ol (0.80 g, 36%) shown below.

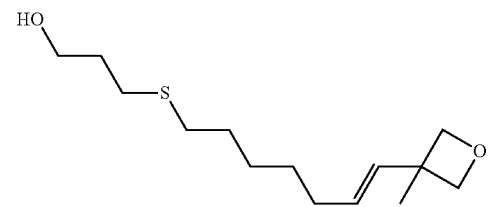

(E)-3-((7-(3-methyloxetan-3-yl)hept-6-en-1-yl)sulfonyl)propan-1-ol (54)

To a 0° C. solution of (E)-3-((7-(3-methyloxetan-3-yl)hept-6-en-1-yl)thio)propan-1-ol 53 (0.8 g, 3 mmol) in MeOH (20 mL) was added a solution of oxone (6 g, 9 mmol) in water (20 mL). Stirred 2 hours at room temp. Diluted with CH$_2$C2 and washed with water, satd. NaCl (2x) and dried (MgSO$_4$). Filtered and concentrated. Obtained an oil. (E)-3-((7-(3-methyloxetan-3-yl)hept-6-en-1-yl)sulfonyl)propan-1-ol (0.45 g, 50%) shown below.

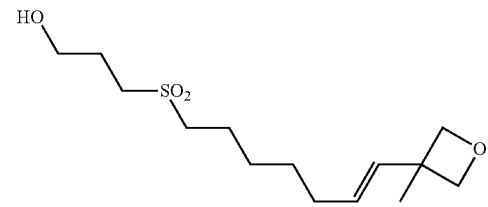

3-((7-(3-methyloxetan-3-yl)heptyl)sulfonyl)propan-1-ol (55)

To a solution of (E)-3-((7-(3-methyloxetan-3-yl)hept-6-en-1-yl)sulfonyl)propan-1-ol 54 (0.6 g, 2 mmol) in MeOH (20 mL) was added 10% Pd—C (0.10 g, 94 µmol). Stirred 18 hours at room temperature under hydrogen gas atmosphere. Evacuated hydrogen gas and filtered through celite with MeOH eluent. Concentration followed by purification by flash chromatography (EtOAc/Hexane) provided 3-((7-(3-methyloxetan-3-yl)heptyl)sulfonyl)propan-1-ol 55 (0.49 g, 82%) clear oil shown below.

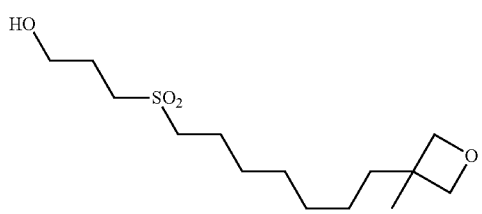

Ethyl (bis(3-((7-(3-methyloxetan-3-yl)heptyl)sulfonyl)-propoxy)phosphoryl)formate (116)

To a room temp flask of 3-((7-(3-methyloxetan-3-yl)heptyl)sulfonyl)propan-1-ol 55 (0.57 g, 2.2 Eq, 1.9 mmol) was added dropwise a solution of ethyl (dichlorophosphoryl)formate[1] (0.17 g, 1 Eq, 0.89 mmol) in THF (15 mL), and DMAP (0.11 g, 1 Eq, 0.89 mmol). The resulting mixture was stirred at room temperature for 18 hours. Diluted with 1:1 EtOAc/ether and washed with 10% Citric acid, satd. NaCl and dried (MgSO$_4$). Purified on Isco Flash chromatography with ELSD detector. Obtained ethyl (bis(3-((7-(3-methyloxetan-3-yl)heptyl)sulfonyl)-propoxy)phosphoryl)formate (0.24 g, 39%) Waxy solid. $^1$H NMR (400 MHz, Chloroform-d) δ 4.52-4.24 (m, 10H), 4.11 (q, J=7.1 Hz, 4H), 3.26-3.04 (m, 4H), 3.04-2.83 (m, 4H), 2.28 (m, 4H), 1.72-1.53 (m, 4H), 1.49-1.26 (m, 23H), 1.25 (s, 6H). $^{31}$P NMR (162 MHz, Chloroform-d) 6-4.43 title compound 124.

Vaghefi, Morteza M.; McKernan, Patricia A.; Robins, Roland K. *Journal of Medicinal Chemistry* 29 (8) 1389-1393, 1986

Example 7. Ethyl (bis(3-(octadecylsulfonyl)propoxy)phosphoryl)formate (125)

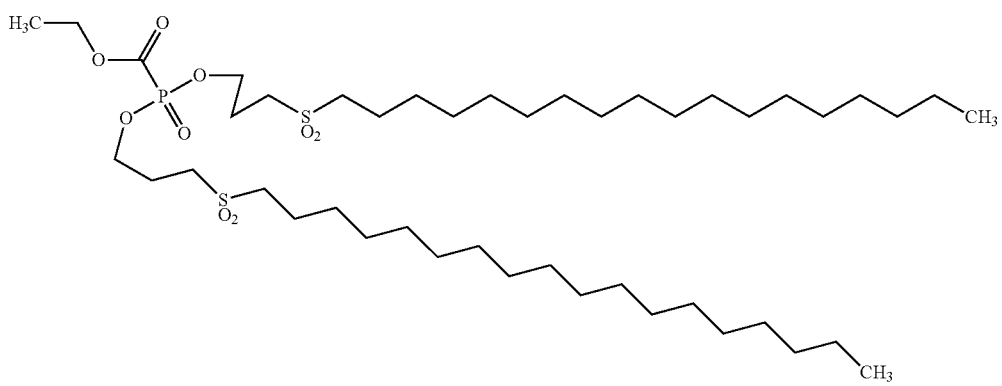

3-(octadecylthio)propan-1-ol (57)

To a solution of 1-bromooctadecane 56 (2.6 g, 7.8 mmol) in EtOH (20 mL) was added 3-mercaptopropan-1-ol (0.93 g, 10 mmol). The resulting mixture was stirred 15 minutes before adding 1 N NaOH (0.53 g, 9.4 mmol). The resulting mixture was stirred 18 hours at room temperature. Concentrated. Diluted with ether and washed with 2 M HCl. Extracted aqueous again with EtOAc. Combined organic layers and washed with satd. NaCl and dried (MgSO$_4$). Purified by flash chromatography on Isco CombiFlash (EtOAc/hexane) Obtained 3-(octadecylthio)propan-1-ol 57 (1.9 g, 71%) shown below.

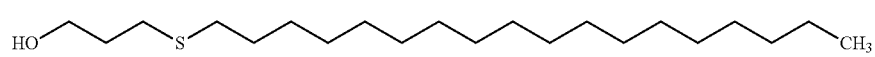

3-(octadecylsulfonyl)propan-1-ol (58)

To a 0° C. solution of 3-(octadecylthio)propan-1-ol 57 (2.00 g, 1 Eq, 5.80 mmol) in MeOH (20 mL) was added a solution of oxone (10.7 g, 3 Eq, 17.4 mmol) in water (20 mL). Stirred 2 hours at room temp. Diluted with CH$_2$C2 and washed with water, satd. NaCl (2×) and dried (MgSO$_4$). Filtered and concentrated. Dried overnight under high vacuum. TLC (10%) MeOH/CH$_2$C2 indicated one major product. Obtained an oil. 3-(octadecylsulfonyl)propan-1-ol 58 (1.4 g, 64%) shown below.

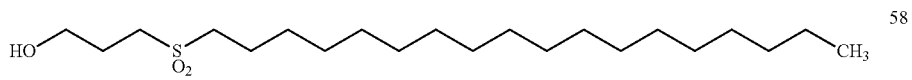 [SMILES: CCCCCCCCCCCCCCCCCCS(=O)(=O)CCCO]

Ethyl (bis(3-(octadecylsulfonyl)propoxy)phosphoryl)formate (125)

To a room temp flask of 3-(octadecylsulfonyl)propan-1-ol 58 (1.10 g, 2.92 mmol) was added drop wise a solution of ethyl (dichlorophosphoryl)formate (253 mg, 1.33 mmol) in THE (15 mL), and trimethyl phosphate (8 mL) and DMAP (162 mg, 1.33 mmol) followed The resulting mixture was stirred at RT for 18 hours. Diluted with EtOAc/ether and washed with 10% citric acid, satd. NaCl and dried (MgSO$_4$). Purified by Isco Flash chromatography with ELSD detector. (EtOAc/Hexane). Obtained ethyl (bis(3-(octadecylsulfonyl)propoxy)phosphoryl)formate 125 (0.43 g, 37%) as a waxy solid. $^1$H NMR (400 MHz, Chloroform-d) δ 4.58-4.19 (m, 4H), 3.81 (t, J=5.8 Hz, 4H), 3.27-3.07 (m, 4H), 2.99 (dt, J=11.1, 3.9 Hz, 4H), 2.29 (m, 2H), 2.11 (m, 4H), 2.00-1.77 (m, 4H), 1.25 (s, 59H), 0.88 (t, J=6.7 Hz, 6H). $^{31}$P NMR (162 MHz, Chloroform-d) δ −4.42.

Example 8. Sodium 3-((12-cyclobutyldodecyl)sulfonyl)propyl(ethoxycarbonyl)-phosphonate (112)

Scheme 6.

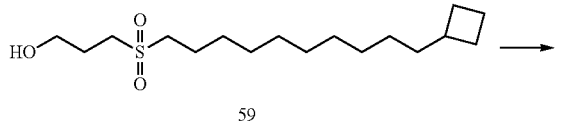

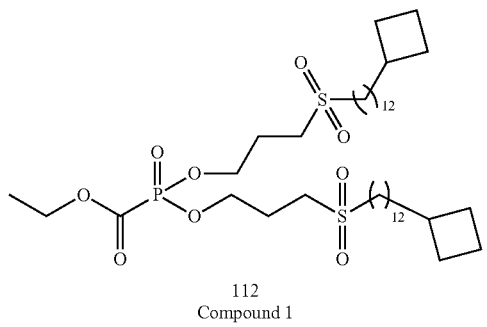

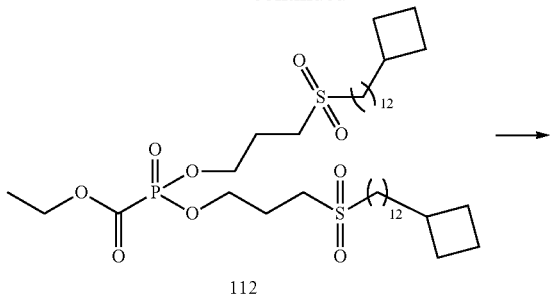

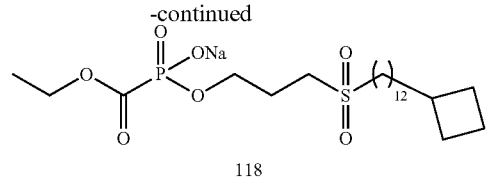

Ethyl (bis(3-((12-cyclobutyldodecyl)sulfonyl)propoxy)phosphoryl)formate (112)

To a solution of (3-((12-cyclobutyldodecyl)sulfonyl)propan-1-ol 59 (240 mg, 0.70 mmol) in 3 mL of dichloromethane was added ethyl(dichlorophosphoryl)formate (67 mg, 0.35 mmol) followed by triethylamine (150 uL, 1.1 mmol). After stirring at room temperature for 5 h, an additional 24 mg of (3-((12-cyclobutyldodecyl)sulfonyl)propan-1-ol was added. The reaction stirred at room temperature overnight, then was poured into dichloromethane and washed with water and brine. The organic layer was dried over magnesium sulfate, filtered, and concentrated. The crude residue was purified by column chromatography eluting with 40-60% ethyl acetate in hexanes to afford 112 as a white solid (144 mg, 51%). 1H NMR (400 MHz, Chloroform-d) δ 4.47-4.25 (m, 6H), 3.11 (dd, J=8.5, 6.7 Hz, 4H), 3.04-2.92 (m, 4H), 2.34-2.14 (m, 6H), 2.06-1.92 (m, 4H), 1.88-1.68 (m, 8H), 1.54 (m, 4H), 1.48-1.06 (m, 43H).

Sodium 3-((12-cyclobutyldodecyl)sulfonyl)propyl (ethoxycarbonyl)phosphonate (118)

To ethyl(bis(3-((12-cyclobutyldodecyl)sulfonyl)propoxy) phosphoryl)formate 112 (118 mg, 0.145 mmol) in methylethylketone (2 mL) was added sodium iodide (33 mg, 0.218 mmol). The reaction was heated to 50° C. and stirred overnight. The reaction mixture was concentrated and the crude residue was purified by column chromatography to afford 118 (45 mg, 64%). $^1$H NMR (400 MHz, Deuterium Oxide) δ 4.11 (q, J=7.1 Hz, 2H), 3.94 (q, J=6.2 Hz, 2H), 3.11 (m, 2H), 2.97 (t, J=7.9 Hz, 2H), 2.12 (m, 1H), 2.03-1.81 (m, 4H), 1.67 (m, 4H), 1.46 (m, 2H), 1.31-1.06 (m, 23H). MS: m/z 483.2533 (M+H)$^+$, 505.2360 (M+Na)$^+$ the title compound of example 8.

Example 9. Ethyl (bis(3-((4-cyclobutylbutyl)sulfonyl)propoxy)phosphoryl)formate (119)

Scheme 7.

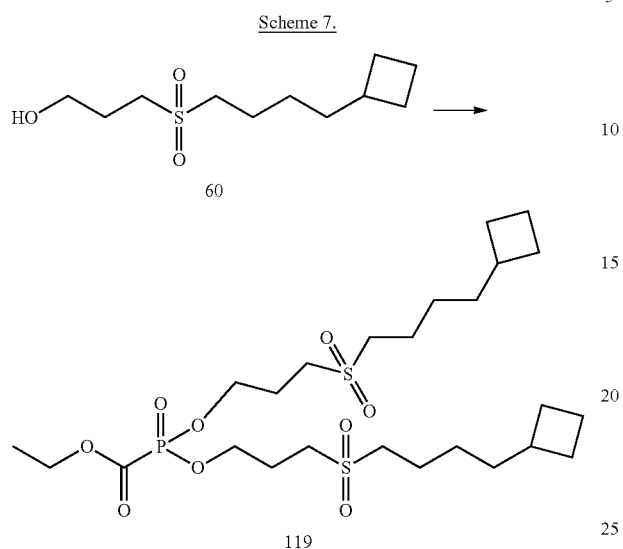

To a solution of 3-((4-cyclobutylbutyl)sulfonyl)propan-1-ol 60 (330 mg, 1.41 mmol) in 3 mL dichloromethane was added ethyl (dichlorophosphoryl)formate (134 mg, 0.70 mmol) followed by triethylamine (294 uL, 2.11 mmol). The reaction stirred at room temperature overnight. An additional 30 mg of ethyl (dichlorophosphoryl)formate was added, and the reaction stirred for an additional 16 h. The reaction was poured into dichloromethane and washed with water and brine. The organic layer was dried over magnesium sulfate, filtered, and concentrated. The crude residue was purified by column chromatography eluting with 0-10% methanol in dichloromethane to afford compound 119 as a white waxy solid (311 mg, 75%). $^1$H NMR (400 MHz, Chloroform-d) δ 4.48-4.25 (m, 6H), 3.12 (m, 4H), 2.98 (m, 4H), 2.35-2.17 (m, 6H), 2.02 (m, 4H), 1.82 (m, 8H), 1.55 (m, 4H), 1.38 (m, 11H). MS: m/z 587.2453 (M+H)$^+$, 609.2273 (M+Na)$^+$.

Example 10. Bis(3-((4-cyclobutylbutyl)sulfonyl)propyl) (((2R,3R,4R,5R)-5-(2,4-dioxo-3,4-dihydropyrimidin-1(2H)-yl)-4-fluoro-3-hydroxy-4-methyltetrahydrofuran-2-yl)methyl) Phosphate (115)

Scheme 8

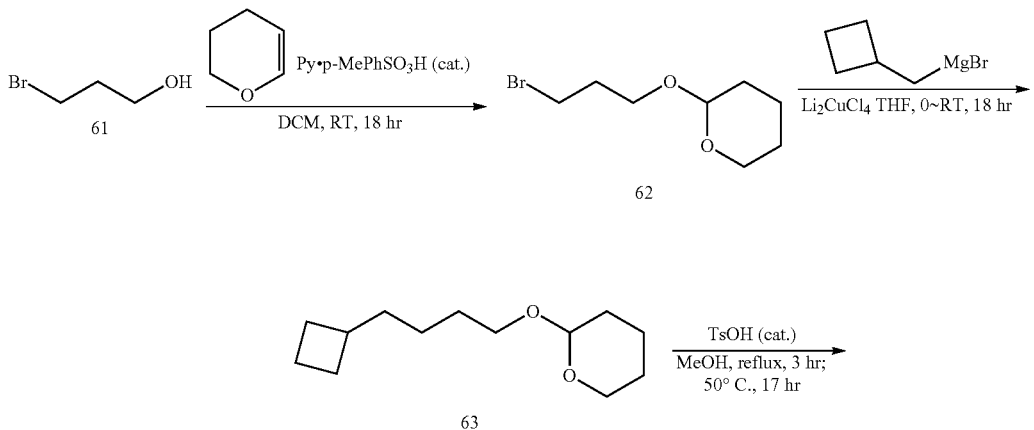

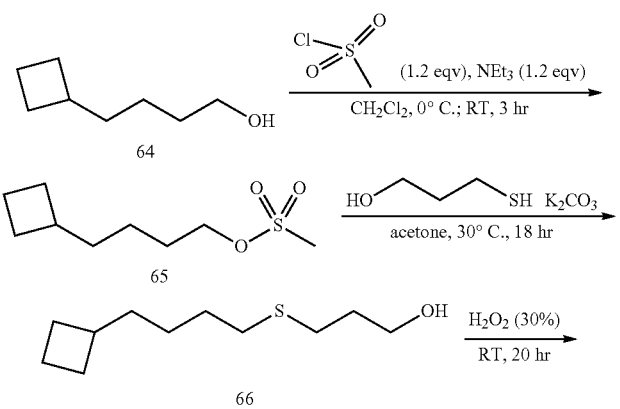

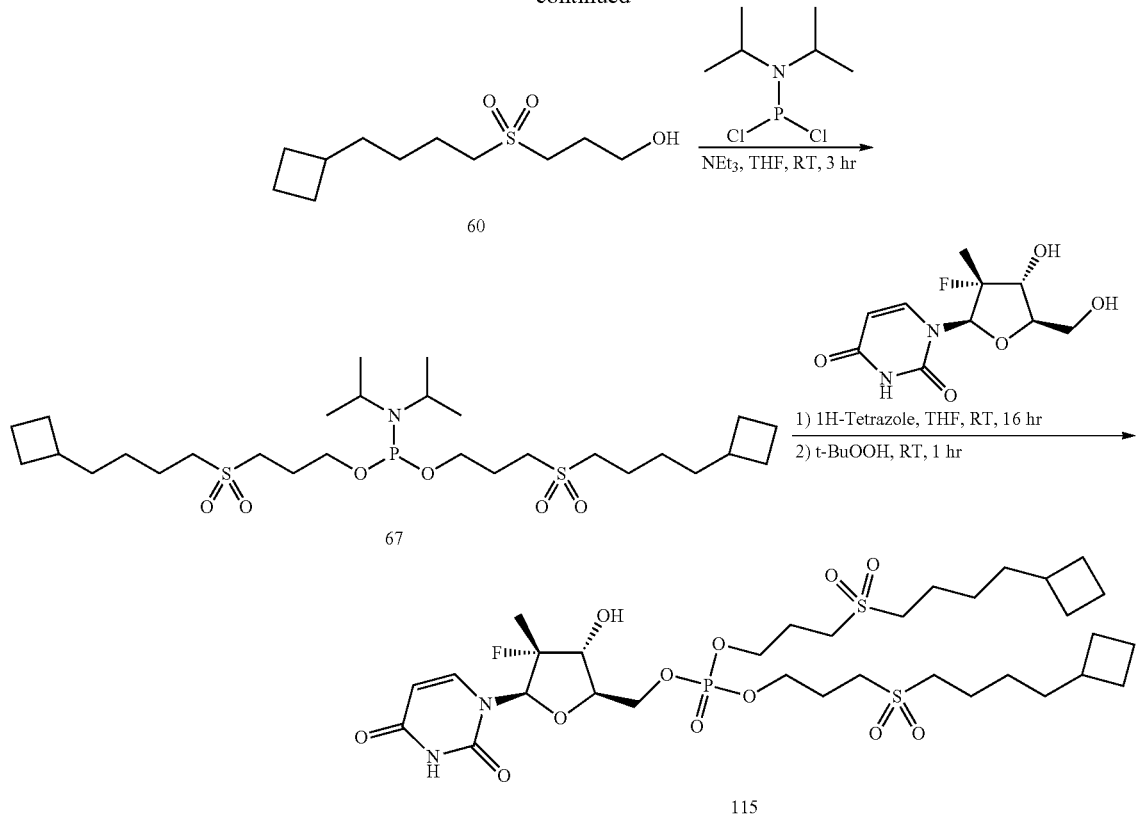

2-(3-Bromopropoxy)tetrahydro-2H-pyran (62). To a suspension of 3-bromopropan-1-ol 61 (7.0 g, 50.4 mmol) and 2,3-dihydro-2H-pyran (8.47 g, 101 mmol) in DCM (80 mL) was added pyridinium p-toluenesulfonate (1.27 g, 5.04 mmol) at RT. The mixture was stirred for 18 hr at RT. It was then concentrated to remove DCM. The residue was treated with hexanes and water. The hexanes phase was washed by brine, dried over $Na_2SO_4$, and evaporated to afford a crude product as brown oil. The crude brown oil was taken up in hexanes and purified by a silica gel column (2% EtOAc in hexanes), collecting first fraction to give 62 (7.65 g, 68%) as colorless oil. $^1$H NMR (400 MHz, Chloroform-d) δ 4.61 (dd, J=4.3, 2.8 Hz, 1H), 3.92-3.80 (m, 2H), 3.58-3.45 (m, 4H), 2.14 (p, J=6.3 Hz, 2H), 1.90-1.45 (m, 6H).

2-(4-Cyclobutylbutoxy)tetrahydro-2H-pyran (63). To a mixed solution of 62 (7.25 g, 32.5 mmol) and $Li_2CuCl_4$ (16.2 mL, 0.1 M solution in THF, 1.62 mmol, 5 mol %) in THF (50 mL) at 0° C. was slowly added Grignard reagent ((cyclobutylmethyl)magnesium bromide) that was made from (bromomethyl)cyclobutane (9.69 g, 65.0 mmol) and grinded magnesium turnings (3.16 g, 130 mmol) in $Et_2O$ (50 mL). After the addition completed, stirred at 0° C. for 30 min and then at RT for 18 hr. The reaction was quenched by $NH_4Cl$ at 0° C. and stirred at RT for 20 min. Then the mixture was treated with hexanes and water. Organic phase was washed by brine, dried over $Na_2SO_4$, and concentrated to give 63 (6.9 g, 100%) as a colorless oil. $^1$H NMR (400 MHz, Chloroform-d) δ 4.57 (dd, J=4.5, 2.7 Hz, 1H), 3.87 (ddd, J=11.1, 7.4, 3.4 Hz, 1H), 3.72 (dt, J=9.6, 6.9 Hz, 1H), 3.56-3.45 (m, 1H), 3.37 (dt, J=9.6, 6.7 Hz, 1H), 2.24 (dq, J=15.5, 7.8 Hz, 1H), 2.10-1.93 (m, 3H), 1.91-1.64 (m, 4H), 1.62-1.45 (m, 7H), 1.39 (q, J=7.4 Hz, 2H), 1.25 (tdd, J=10.0, 7.2, 3.9 Hz, 2H). $^{13}$C NMR (101 MHz, Chloroform-d) δ 98.78, 67.65, 62.28, 36.79, 36.06, 30.73, 29.70, 28.32 (2C), 25.46, 23.77, 19.66, 18.43.

4-Cyclobutylbutan-1-ol (64). To a solution of 63 (6.9 g, 32.5 mmol) in methanol (40 mL) was added p-toluenesulphonic acid monohydrate (309 ng, 1.62 mmol). The mixture was refluxed for 3 hr and then stirred at 50° C. for 16 hr. Most of the methanol was removed under reduced pressure. Water (20 mL) was added to the residue and the mixture was extracted with hexane (4×30 mL). The combined organic layers were washed with saturated aqueous $NaHCO_3$ and brine, dried over $Na_2SO_4$, and concentrated under reduced pressure to give 64 (4.1 g, 98%) as an oil. $^1$H NMR (400 MHz, Chloroform-d) δ 4.56 (s, 1H), 3.64 (t, J=6.7 Hz, 2H), 2.24 (p, J=7.8 Hz, 1H), 2.06-1.95 (m, 2H), 1.88-1.71 (m, 2H), 1.60-1.51 (m, 4H), 1.38 (q, J=7.4 Hz, 2H), 1.31-1.17 (m, 2H).

4-Cyclobutylbutyl methanesulfonate (65). 64 (4.1 g, 32.0 mmol) and triethylamine (4.37 g, 43.2 mmol) were dissolved in DCM (60 mL) and cooled to 0° C. Methanesulfonyl chloride (4.94 g, 43.2 mmol) was added dropwise to the stirred solution. The reaction was stirred at RT for 3 hr, quenched with 0.5 N aq HCl. 25 ml hexanes was added. The organic phase was separated and evaporated. The residual oil and above aqueous phase were combined and extracted with hexanes (3×50 mL). The organic layer was then washed with $H_2O$, sat. $NaHCO_3$, brine, dried over sodium sulfate, filtered, and concentrated under reduced pressure to give 65 (6.23 g, 94%) as an orange oil. $^1$H NMR (400 MHz, Chloroform-d) δ 4.21 (t, J=6.6 Hz, 2H), 3.00 (s, 3H), 2.25 (p, J=7.8 Hz, 1H), 2.08-1.97 (m, 2H), 1.88-1.68 (m, 4H), 1.57 (td, J=8.7, 2.5 Hz, 2H), 1.45-1.36 (m, 2H), 1.34-1.20 (m, 2H).

3-((4-Cyclobutylbutyl)thio)propan-1-ol (66). Under nitrogen, to a solution of 65 (6.23 g, 30.2 mmol) and 3-mercaptopropan-1-ol (5.57 g, 60.4 mmoL) in acetone (150 mL) was added potassium carbonate (10.4 g, 75.5 mmol). The suspension mixture was stirred at 30° C. for 18 hr. TLC showed the SM consumed. The mixture was evaporated and the residue was partitioned between water and hexanes. The hexanes phase was washed with 1 N sodium hydroxide, water, brine, dried over sodium sulfate, and the volatiles was removed under vacuum to give 66 (6.0 g, 98%) as oil. $^1$H NMR (400 MHz, Chloroform-d) δ 3.75 (d, J=6.0 Hz, 2H), 2.63 (t, J=7.0 Hz, 2H), 2.56-2.45 (m, 2H), 2.24 (p, J=7.8 Hz, 1H), 2.08-1.93 (m, 2H), 1.93-1.68 (m, 5H), 1.63-1.47 (m, 4H), 1.45-1.35 (m, 2H), 1.28 (tdd, J=12.4, 6.5, 3.5 Hz, 2H). MS: m/z 203.1460 (M+H)$^+$.

3-((4-Cyclobutylbutyl)sulfonyl)propan-1-ol (60). To a solution of 66 (6.0 g, 29.7 mmol) in AcOH (120 mL) was added 30% $H_2O_2$ (27.3 ml, 267 mmol). The solution was stirred at RT for 20 h. Evaporation of the solvent at 50° C. under reduced pressure. The residual oil was treated with DCM and sat. $NaHCO_3$. The organic phase was washed by brine, dried over $Na_2SO_4$, and evaporated to leave a white solid. The solid was washed by hexanes (3×35 mL) to afford 60 (5.77 g, 83%) as a white solid. $^1$H NMR (400 MHz, Chloroform-d) δ 3.82 (q, J=5.6 Hz, 2H), 3.19-3.08 (m, 2H), 3.02-2.92 (m, 2H), 2.24 (h, J=7.6 Hz, 1H), 2.13-1.98 (m, 3H), 1.89-1.73 (m, 5H), 1.69-1.47 (m, 4H), 1.47-1.30 (m, 3H). MS: m/z 235.1361 (M+H)$^+$.

Bis(3-((4-cyclobutylbutyl)sulfonyl)propyl) diisopropylphosphoramidite (67). 1,1-dichloro-N,N-diisopropylphosphanamine (1.0 g, 4.95 mmol) was added in THF (5 mL) at 0° C. under $N_2$. Triethylamine (1.05 g, 10.4 mmol) was added. Then a solution of 60 (2.32 g, 9.90 mmol) in THF (6 mL) was added under stirring via a syringe. Continued to stir at RT for 3 hr. The reaction mixture was filtered. The solid was washed by THF. The filtrate was evaporated to afford 67 (2.94 g, 99%) as a light orange oil. $^1$H NMR (400 MHz, Chloroform-d) δ 3.85-3.64 (m, 4H), 3.61-3.48 (m, 2H), 3.12-3.03 (m, 4H), 3.00-2.90 (m, 4H), 2.24 (h, J=7.7 Hz, 2H), 2.16-1.93 (m, 6H), 1.93-1.73 (m, 10H), 1.57 (td, J=8.7, 2.5 Hz, 4H), 1.44-1.23 (m, 8H), 1.17 (d, J=6.8 Hz, 12H). $^{13}$C NMR (101 MHz, Chloroform-d) δ 61.45, 61.27, 52.96 (2C), 49.74 (2C), 43.00, 42.88, 36.28 (2C), 35.63 (2C), 28.25 (4C), 26.11 (2C), 25.59, 24.67, 24.59 (2C), 23.96, 23.89, 21.87 (2C), 18.40 (2C). $^{31}$P NMR (162 MHz, Chloroform-d) δ 147.14. MS: m/z 598.3358 (M+H)$^+$.

Bis(3-((4-cyclobutylbutyl)sulfonyl)propyl) (((2R,3R,4R,5R)-5-(2,4-dioxo-3,4-dihydropyrimidin-1(2H)-yl)-4-fluoro-3-hydroxy-4-methyltetrahydrofuran-2-yl)methyl) phosphate (115). 67 (300 mg, 0.502 mmol) was added in THF (10 mL) under $N_2$. 1H-tetrazole (1.67 mL, 0.45 M in acetonitrile, 0.753 mmol) was added. Then 1-((2R,3R,4R,5R)-3-fluoro-4-hydroxy-5-(hydroxymethyl)-3-methyltetrahydrofuran-2-yl)pyrimidine-2,4(1H,3H)-dione (131 mg 0.502 mmol) was added at 0° C. The mixture was stirred at RT for 16 hr. The reaction mixture was cooled to 0° C. 2-Hydroperoxy-2-methylpropane (5.5 M in nonane, 0.55 mL, 3.01 mmol) was added. Stirred at RT for 1 hr. DCM (5 mL) and 10% $Na_2SO_3$ aqueous solution (6 mL) were added and extracted. The organic phase was separated. The aqueous phase was washed by DCM. The organic phase was washed by sat. $NaHCO_3$ solution and brine, dried over $Na_2SO_4$, and evaporated to leave a colorless oil. It was purified by Prep-TLC plate (DCM/MeOH 100:5.5) to give 115 (58 mg, 15%) as a white solid. $^1$H NMR (400 MHz, Chloroform-d) δ 9.62 (s, 1H), 7.44 (d, J=8.1 Hz, 1H), 5.78 (d, J=8.1 Hz, 1H), 4.49 (dd, J=11.4, 6.0 Hz, 1H), 4.38 (ddd, J=11.1, 6.7, 3.3 Hz, 1H), 4.27 (q, J=6.4 Hz, 4H), 4.13 (d, J=7.2 Hz, 1H), 3.96 (s, 1H), 3.12 (t, J=7.5 Hz, 4H), 3.03-2.91 (m, 4H), 2.33-2.12 (m, 8H), 2.03 (dtd, J=11.3, 7.7, 7.3, 2.9 Hz, 4H), 1.89-1.72 (m, 8H), 1.58 (qd, J=8.8, 2.4 Hz, 4H), 1.48-1.30 (m, 11H). $^{31}$P NMR (162 MHz, Chloroform-d) δ -1.35. MS: m/z 773.2905 (M+H)$^+$, 771.2777 (M−H)$^-$. HPLC: 96.14%.

Example 11. 3-((4-Cyclobutylbutyl)sulfonyl)propyl (((2R,3R,4R,5R)-5-(2,4-dioxo-3,4-dihydropyrimidin-1(2H)-yl)-4-fluoro-3-hydroxy-4-methyltetrahydrofuran-2-yl)methyl)phenyl Phosphate (114)

Scheme 9

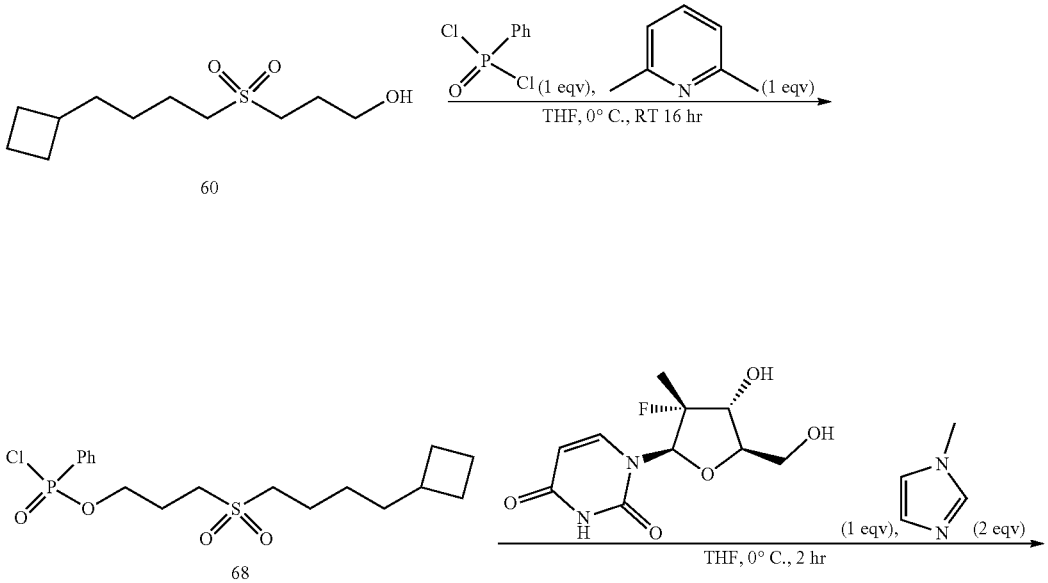

-continued

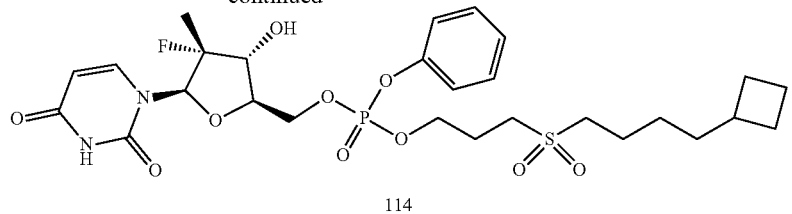

114

3-((4-Cyclobutylbutyl)sulfonyl)propyl phenyl (S)-phosphorochloridate (68). To a cooled (0° C.) solution of phenyl phosphorodichloridate (300 mg, 1.42 mmol) in THF (5 mL) was slowly added a solution of 60 (340 mg, 1.45 mmol) in THF (2 mL) followed by dropwise addition of 2,6-lutidine (152 mg, 1.42 mmol) in THF (1 mL) via a syringe within 10 min. After stirring at 0° C. for 5 min, the cooling bath was removed. Stirred at RT for 18 hr. The reaction mixture was filtered. the solid was washed by THF. The filtrate was evaporated to leave crude 68 (0.58 g, 100%) as a colorless oil. $^1$H NMR (400 MHz, Chloroform-d) δ 7.44-7.36 (m, 2H), 7.29-7.23 (m, 3H), 4.49 (dt, J=8.5, 5.9 Hz, 2H), 3.17-3.03 (m, 2H), 3.01-2.94 (m, 2H), 2.36 (ddt, J=10.9, 5.9, 1.6 Hz, 2H), 2.24 (p, J=7.7 Hz, 2H), 2.09-1.98 (m, 3H), 1.86-1.77 (m, 3H), 1.60-1.51 (m, 2H), 1.43-1.30 (m, 3H). $^{31}$P NMR (162 MHz, Chloroform-d) δ −0.39.

3-((4-Cyclobutylbutyl)sulfonyl)propyl (((2R,3R,4R,5R)-5-(2,4-dioxo-3,4-dihydropyrimidin-1(2H)-yl)-4-fluoro-3-hydroxy-4-methyltetrahydrofuran-2-yl)methyl)phenyl phosphate (114). To a suspension of 1-((2R,3R,4R,5R)-3-fluoro-4-hydroxy-5-(hydroxymethyl)-3-methyltetrahydrofuran-2-yl)pyrimidine-2,4(1H,3H)-dione (369 mg, 1.42 mmol) in THF (10 mL) at 0° C. was added 1-methyl-1H-imidazole (233 mg, 2.84 mmol), followed by dropwise addition of a solution of 68 (580 mg, 1.42 mmol) in THF (6 mL). Stirred at 0° C. for 2 hr. The cooling bath was removed and the mixture was stirred at RT for 5 min. Reaction was quenched by sat. NH$_4$Cl aqueous solution (3 mL). Most of THF was removed under reduced pressure. The residue was treated with EtOAc/water. Organic phase was washed by brine, dried over Na$_2$SO$_4$, and evaporated to leave 0.78 g colorless sticky oil. It was dissolved in DCM and purified by two prep-TLC plates (20 cm×20 cm size, 1000 um thick, DCM/MeOH 100:5) to give 0.34 g solid foam. It was dissolved in DCM and purified the second time by one Prep-TLC plate (20 cm×20 cm size, 1000 um thick, EtOAc/DCM 3:1) to afford 0.31 g of colorless gum. It was dissolved in DCM and purified the third time by four Prep-TLC plates (20 cm×20 cm size, 250 um thick, EtOAc/DCM 3:1) to afford 280 mg of colorless gum. TLC showed it still not pure. It was dissolved in DCM and purified the fourth time by four prep-TLC (20 cm×20 cm size, 250 um thick, EtOAc/DCM 3:1) to afford 126 (252 mg, 28%) as a white solid. $^1$H NMR (499 MHz, Chloroform-d) δ 9.24 (s, 1H), 7.51-7.28 (m, 3H), 7.22 (t, J=7.3 Hz, 3H), 6.12 (s, 1H), 5.63 (t, J=7.8 Hz, 1H), 4.59 (t, J=9.1 Hz, 1H), 4.49 (ddd, J=11.7, 7.3, 3.5 Hz, 1H), 4.36 (dq, J=12.8, 5.8 Hz, 2H), 4.12 (d, J=9.1 Hz, 1H), 3.92 (s, 1H), 3.54 (dd, J=31.6, 8.8 Hz, 1H), 3.05 (t, J=7.9 Hz, 2H), 2.94 (t, J=8.1 Hz, 2H), 2.25 (h, J=8.0, 7.4 Hz, 3H), 2.09-1.96 (m, 2H), 1.90-1.74 (m, 5H), 1.65- 1.50 (m, 2H), 1.37 (d, J=23.3 Hz, 6H). $^{31}$P NMR (202 MHz, Chloroform-d) δ −6.39, −6.49. MS m/z 633.2038 (M+H)$^+$, 631.1923 (M−H)$^−$. HPLC: 96.33%.

Example 12. Antiviral Activity of Prodrugs

Screening Assays for HSV-1, HSV-2, CMV, and VZV

Cells. Human foreskin fibroblast (HFF) cells were prepared from human foreskin tissue. The tissue was incubated at 4° C. for 4 h in Clinical Medium and then placed in phosphate buffered saline (PBS) to remove the red blood cells, and resuspended in trypsin/EDTA solution. The tissue suspension was incubated at 37° C. and gently agitated to disperse the cells, which were collected by centrifugation. Cells were resuspended in 4 ml Clinical Medium and placed in a flask and incubated at 37° C. in a humidified CO$_2$ incubator for 24 h. The media was then replaced with fresh Clinical Medium and the cell growth was monitored daily until a confluent monolayer has formed. The HFF cells were then expanded through serial passages in standard growth medium of MEM with Earl's salts supplemented with 10% FBS and antibiotics. The cells were passaged routinely and used for assays at or below passage 10.

Primary Cytopathic Effect (CPE) Reduction Assay. Low passage (3-10) HFF cells were trypsinized, counted, and seeded into 96 well tissue culture plates in 0.1 ml of MEM supplemented with 10% FBS. The cells were then incubated for 24 h at 37° C. The media was then removed and 100 µl of MEM containing 2% FBS was added to all but the first row. In the first row, 125 µl of media containing the experimental drug was added in triplicate wells. Media alone was added to both cell and virus control wells. The drug in the first row of wells was then diluted serially 1:5 throughout the remaining. The plates were then incubated for 60 min and 100 µl of a virus suspension was added to each well, excluding cell control wells which received 100 µl of MEM. The plates were then incubated at 37° C. in a CO$_2$ incubator for three days for HSV-1 and HSV-2, 10 days for VZV, or 14 d for CMV. After the incubation period, media was aspirated and the cells stained with crystal violet in formalin for 4 h. The stain was then removed and the plates were rinsed until all excess stain was removed. The plates were allowed to dry for 24 h and the amount of CPE in each row determined using a BioTek Multiplate Autoreader. EC$_{50}$ and CC$_{50}$ values were determined by comparing drug treated and untreated cells using a computer program.

TABLE 1

In vitro antiviral activity for prodrugs. EC50 is the concentration of the test material in µM producing a 50% reduction in the Cytopathic Effect of the virus (CPE). The TI is the therapeutic index derived from EC50/CC50.

| Test Compound Number | EC50 and TI | HSV1 E377 | HSV2 G | hCMV1 AD169 | hCMV2 GDGRK17 | mCMV Smith | VZV Ellen |
|---|---|---|---|---|---|---|---|
| 120 | EC50 | 0.07 | 0.01 | 0.008 | <0.0003 | <0.0003 | 0.02 |
|  | TI | 149 | >3950 | 74 | >2772 | >3125 | 25 |
| 121 | EC50 | 0.01 | 0.01 | <0.01 | <0.0003 | <0.0003 | 0.01 |
|  | TI | 1159 | 498 | >19 | >2753 | >3125 | 23 |
| 122 | EC50 | 0.02 | 0.14 | <0.01 | <0.0003 | <0.0003 | 0.007 |
|  | TI | 469 | >14 | >19 | >2209 | >3125 | 31 |
| 110 | EC50 | 0.16 | 0.04 | 0.01 | <0.0003 | <0.0003 | 0.01 |
|  | TI | >313 | >1250 | 184 | >3125 | 2213 | 225 |
| 123 | EC50 | <0.05$^a$ |  | <0.05 |  |  |  |
|  | TI | >142$^a$ |  | >5 |  |  |  |
| 124 | EC50 | >150 |  | >150 |  |  |  |
|  | TI | 1 |  | 1 |  |  |  |
| 125 | EC50 |  |  | 132 |  |  |  |
|  | TI |  |  | >1 |  |  |  |
| 118 | EC50 | 0.63 |  | 0.23 |  |  |  |
|  | TI | 128 |  | 198 |  |  |  |
| 119 | EC50 |  |  | >30 |  |  |  |
|  | TI |  |  | <3 |  |  |  |
| Control Acyclovir or Ganciclovir | Control EC50 TI | Acy. 0.96 >156 | Acy. 0.38 >395 | Gan. 1.63 >92 | Gan. 0.15 >1030 | Gan. 0.17 >882 | Acy. 3.24 >46 |

HSV1 is Herpes Simplex Virus 1, HSV2 is Herpes Simplex Virus 2, hCMV is human Cytomegalovirus, mCMV is murine Cytomegalovirus, and VZV is Vericella Zoster Virus.
$^a$HSV1 strain used was DM2.1

Figure 2:
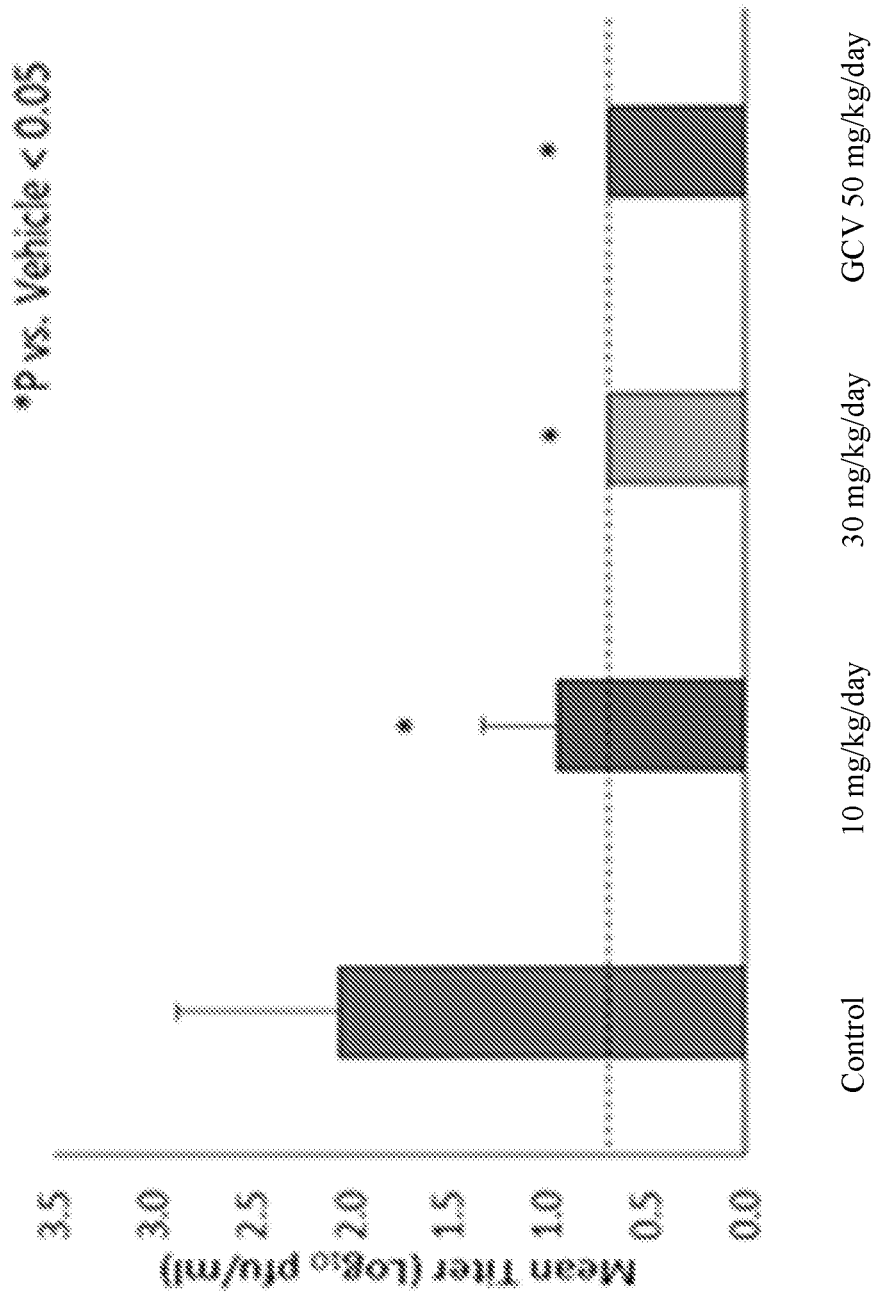
FIG. 2 illustrates in vivo efficacy of compound 122 against mCMV infection relative to ganciclovir (GCV) or vehicle control measured in liver following oral dosing.
Figure 3:
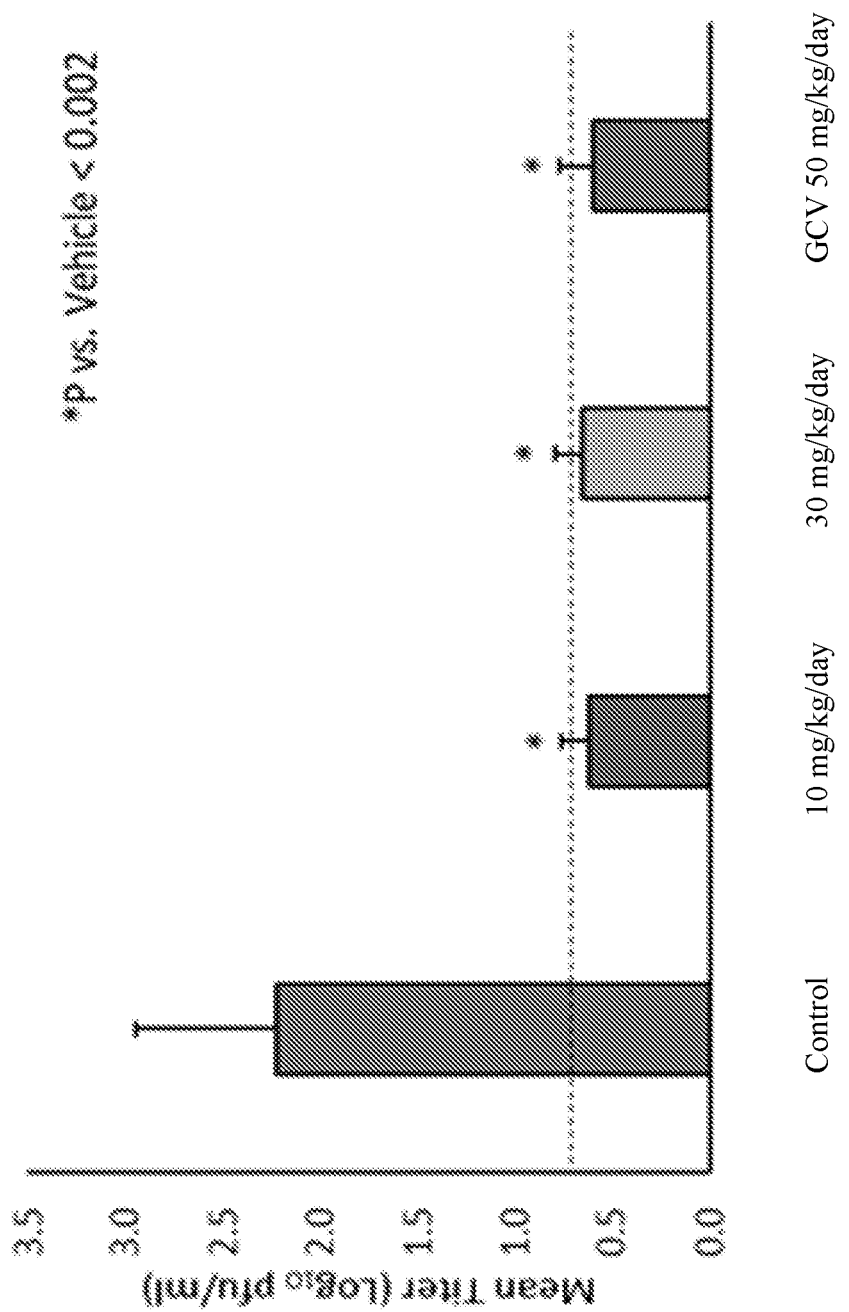
FIG. 3 illustrates in vivo efficacy of compound 122 against mCMV infection relative to ganciclovir (GCV) or vehicle control measured in spleen following PO dosing.
Figure 4:
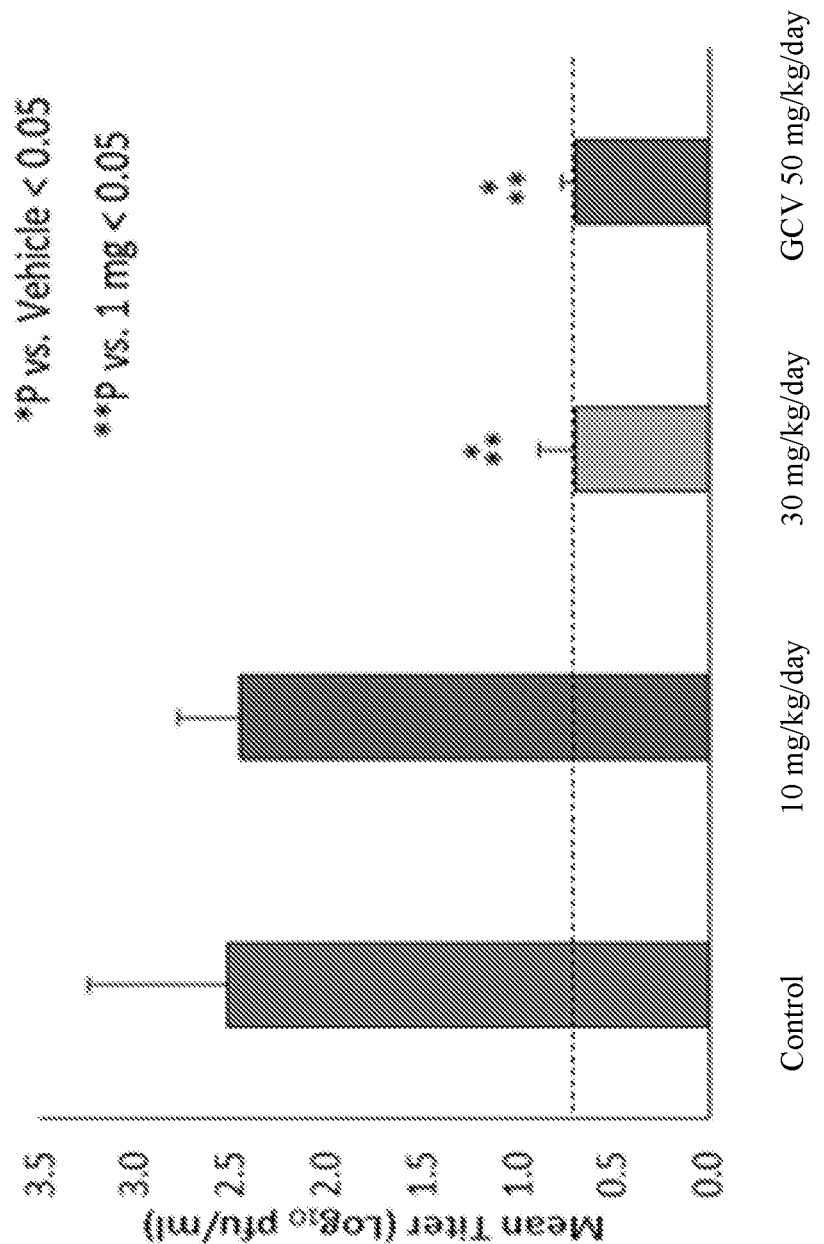
FIG. 4 illustrates in vivo efficacy of compound 122 against mCMV infection relative to ganciclovir (GCV) or vehicle control measured in spleen following oral dosing.

Antiviral Efficacy of Compound 122 in mCMV Infected Mice:

For the in vivo efficacy study, two doses of 5 and 15 mg/kg (n=8/group) of compound 122 was administered PO twice a day for 4 days, beginning one day prior to viral challenge with mCMV strain K181 in Balb/c mice. In a second study the same procedure was used but with oral doses of 0.5 and 1.5 mg/kg. Controls for the study include a vehicle group (0.5% CMC) and a ganciclovir (GCV) group (n=4, 25 mg/kg bid IP). At the end of the study, the mice were sacrificed and the spleen and liver harvested and stored at −80° C. The tissues were shipped to Louisiana State University (Rhonda Cardin, Baton Rouge, LA) and evaluated for liver or spleen titers against mCMV infection. Results are illustrated in FIGS. 1-4.

Additional studies in HFF cells were performed using the procedures as outlined in US Patent Application Publication No: 2011/0263535 A1 with compounds of 120, 121, and 122. Each of the compounds were tested versus Human Cytomegalovirus Strain AD169 in HFF cells using ganciclovir as a comparator. Results are shown in Table 2.

TABLE 2

| Compound | EC$_{90}$ µM | Therapeutic index EC$_{90}$/HFF Cytotoxicity 50% |
|---|---|---|
| Ganciclovir | >150 | 1 |
| 120 | <0.02 | >37 |
| 121 | <0.02 | >15 |
| 122 | <0.02 | >13 |

The foregoing description of particular embodiment(s) is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only. While the processes or compositions are described as an order of individual steps or using specific materials, it is appreciated that steps or materials may be interchangeable such that the description of the invention may include multiple parts or steps arranged in many ways as is readily appreciated by one of skill in the art.

It will be understood that, although the terms "first," "second," "third" etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, "a first element," "component," "region," "layer," or "section" discussed below could be termed a second (or other) element, component, region, layer, or section without departing from the teachings herein.

The terminology used herein is for the purpose of describing particular embodiments only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof. The term "or a combination thereof" means a combination including at least one of the foregoing elements.

Unless otherwise defined, all terms (including technical and scientific terms) used herein have the same meaning as commonly understood by one of ordinary skill in the art to which this disclosure belongs. It will be further understood that terms such as those defined in commonly used dictionaries, should be interpreted as having a meaning that is consistent with their meaning in the context of the relevant art and the present disclosure, and will not be interpreted in an idealized or overly formal sense unless expressly so defined herein.

Specific embodiments of the prodrug are described herein. It should be understood that the prodrugs of this disclosure may be embodied in different forms and should not be construed as limited to the specific embodiments set forth in this disclosure.

Unless otherwise defined, all terms (including technical and scientific terms) used herein have the same meaning as commonly understood by one of ordinary skill in the art to which this disclosure belongs. It will be further understood that terms such as those defined in commonly used dictionaries, should be interpreted as having a meaning that is consistent with their meaning in the context of the relevant art and the present disclosure, and will not be interpreted in an idealized or overly formal sense unless expressly so defined herein.

Various modifications of the present invention, in addition to those shown and described herein, will be apparent to those skilled in the art of the above description. Such modifications are also intended to fall within the scope of the appended claims.

It is appreciated that all reagents are obtainable by sources known in the art unless otherwise specified.

Patents, publications, and applications mentioned in the specification are indicative of the levels of those skilled in the art to which the invention pertains. These patents, publications, and applications are incorporated herein by reference to the same extent as if each individual patent, publication, or application was specifically and individually incorporated herein by reference.

The foregoing description is illustrative of particular embodiments of the invention, but is not meant to be a limitation upon the practice thereof.

The invention claimed is:
1. A prodrug consisting of an anti-infective therapeutic agent and a cap having a structure according to formula (I):
the anti-infective therapeutic agent comprising a phosphonate, said anti-infective therapeutic agent covalently attached to the cap by said phosphonate, the cap having a structure according to formula (I)

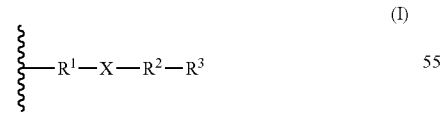

(I)

where:
$R^1$ is a branched or linear substituted or unsubstituted C2-C6 alkyl, alkenyl, or alkynyl;
X is $—S(O)_2—$;
$R^2$ is a linear substituted or unsubstituted C4-C20 alkyl, alkenyl, or alkynyl; and
$R^3$ is substituted or unsubstituted C3-C5 cycloalkyl, an unsubstituted C3-C5 cycloheteroalkyl, or a substituted or unsubstituted phenyl; or $R^3$ is a radical having a structure according to formula (III) or formula (IV):

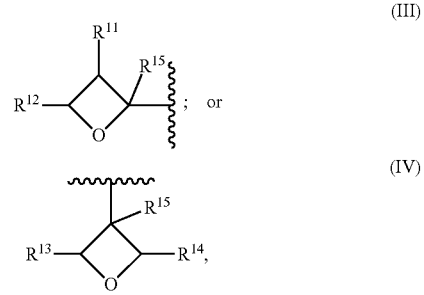

where: $R^{11}$, $R^{12}$, $R^{13}$, $R^{14}$, and $R^{15}$ are independently chosen from $(C_1-C_{12})$ alkyl, $—CF_3$, or $—OH$, or $—H$;
wherein said anti-infective therapeutic agent has a structure according to formula (II):

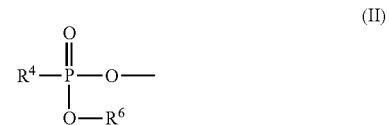

(II)

where $R^4$ is chosen from the following groups:

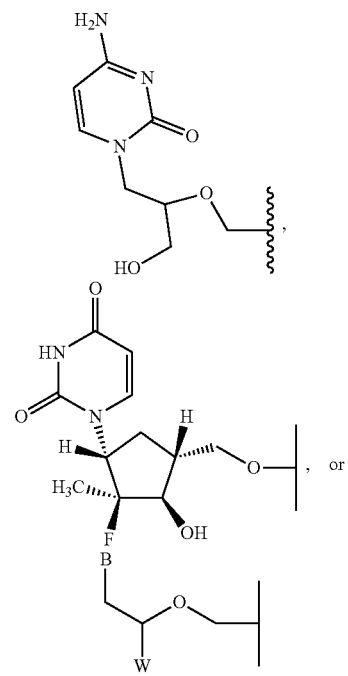

where B=A and W=$CH_2OH$ and the therapeutic agent is (S)-9-[(2S)-3-hydroxy-2-phosphonylmethoxypropyl] adenine;
or B=A and W=H and the therapeutic agent is phosphonomethoxy-ethyl-adenine;
or B=DAP and W=$CH_3$ and the therapeutic agent is 9-[2-(R)-(phosphonomethoxy) propyl]-2,6-diaminopurine;

or B=A and W=CH$_2$F and the therapeutic agent is(S)-9-(3-fluoro-2-phosphonylmethoxypropyl) adenine;
or B=DAP and W=CH$_2$F and the therapeutic agent is(S)-9-[3-fluoro-2-phosphonylmethoxypropyl]diaminopurine;
or B=G and W=CH$_2$F and the therapeutic agent is(S)-9-(3-fluoro-2-phosphonylmethoxypropyl) guanine;
or B=DAP and W=CH$_2$F and the therapeutic agent is (R)-(S)-9-[3-fluoro-2-phosphonylmethoxypropyl]diaminopurine;
or B=G and W=CH$_2$F and the therapeutic agent is (R)-9-(3-fluoro-2-phosphonylmethoxypropyl) guanine;
or B=7-deaza-G and W=H and the therapeutic agent is 7-deaza-9-(2-phosphonylmethoxyethyl) guanine;
or B=8-aza-G and W=H and the therapeutic agent is 9-(2-phosphonylmethoxyethyl)-8-aza-guanine;
or B=8-aza-G and W=CH$_3$ and the therapeutic agent is (R)-(2-(phosphonomethoxy) propyl)-8-aza-guanine;
or B=DAPy and W=H and the therapeutic agent is 6-[2-(phosphonomethoxy) ethyl]-2,4-diaminopyrimidine;
or B=DAPy and W=CH$_3$ and the therapeutic agent is (R)-6-[2-(phosphonomethoxy) ethyl]-2,4-diaminopyrimidine;
and R$^6$ is H or —R$^1$XR$^2$R$^3$ (formula I)
thereby forming said prodrug;
or salts thereof,
wherein as defined as element B, A is adenine, G is guanine, DAP is 2,6-diaminopurine, 7-deaza-G is 7-deaza-guanine, 8-aza-G is 8-aza-guanine, and DAPy is 2,4-diaminopyrimidine.

2. The prodrug of claim 1 wherein:
when R$^3$ is a (C$_3$-C$_4$) cycloheteroalkyl, the heteroatom is oxygen.

3. The prodrug of claim 1 wherein the therapeutic agent has a structure according to formula (II):

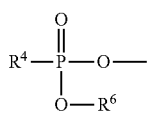

where R$^4$ is

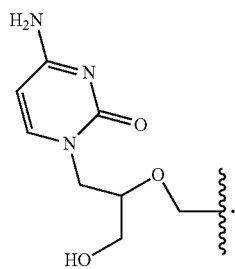 [SMILES: *COC(CO)Cn1ccc(N)nc1=O ; "."]

4. The prodrug according to claim 1 wherein the therapeutic agent has a structure according to formula (II):

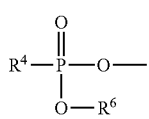

and wherein R$^4$ is

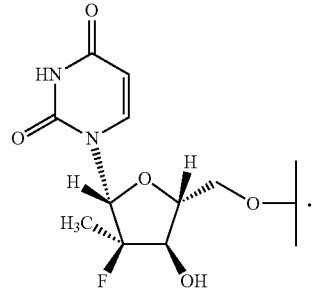 [SMILES: CC(C)OC[C@H]1O[C@@H](n2ccc(=O)[nH]c2=O)[C@](C)(F)[C@@H]1O]

5. The prodrug of claim 1 wherein the therapeutic agent has a structure according to formula (II):

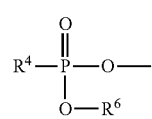

and wherein R$^4$ is

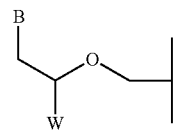

where B=A and W=CH$_2$OH and the therapeutic agent is(S)-9-[(2S)-3-hydroxy-2-phosphonylmethoxypropyl]adenine;
or B=A and W=H and the therapeutic agent is phosphonomethoxy-ethyl-adenine;
or B=DAP and W=CH$_3$ and the therapeutic agent is 9-[2-(R)-(phosphonomethoxy) propyl]-2,6-diaminopurine;
or B=A and W=CH$_2$F and the therapeutic agent is(S)-9-(3-fluoro-2-phosphonylmethoxypropyl) adenine;
or B=DAP and W=CH$_2$F and the therapeutic agent is(S)-9-[3-fluoro-2-phosphonylmethoxypropyl]diaminopurine;
or B=G and W=CH$_2$F and the therapeutic agent is(S)-9-(3-fluoro-2-phosphonylmethoxypropyl) guanine;
or B=DAP and W=CH$_2$F and the therapeutic agent is (R)-(S)-9-[3-fluoro-2-phosphonylmethoxypropyl]diaminopurine;
or B=G and W=CH$_2$F and the therapeutic agent is (R)-9-(3-fluoro-2-phosphonylmethoxypropyl) guanine;
or B=7-deaza-G and W=H and the therapeutic agent is 7-deaza-9-(2-phosphonylmethoxyethyl) guanine;
or B=8-aza-G and W=H and the therapeutic agent is 9-(2-phosphonylmethoxyethyl)-8-aza-guanine;
or B=8-aza-G and W=CH$_3$ and the therapeutic agent is (R)-(2-(phosphonomethoxy) propyl)-8-aza-guanine;
or B=DAPy and W=H and the therapeutic agent is 6-[2-(phosphonomethoxy) ethyl]-2,4-diaminopyrimidine;
or B=DAPy and W=CH$_3$ and the therapeutic agent is (R)-6-[2-(phosphonomethoxy) ethyl]-2,4-diaminopyrimidine;
wherein as defined as element B, A is adenine and G is guanine, DAP is 2,6-diaminopurine, 7-deaza-G is 7-deaza-guanine, 8-aza-G is 8-aza-guanine, and DAPy is 2,4-diaminopyrimidine.

6. The prodrug according to claim 1, wherein $R^3$ is cyclopropyl, cyclobutyl, oxetan-2-yl, 2-trifluoromethyl cyclopropane-1-yl, 1-trifluoromethyl cyclopropane-1-yl, 3-methyl-oxetan-1-yl and 3-ethyl-3-methyl-oxetan-1-yl.

7. The prodrug according to claim 1, wherein $R^3$ is a radical having a structure according to formula (III) or formula (IV):

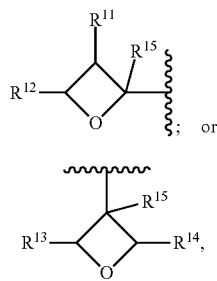

where: $R^{11}$, $R^{12}$, $R^{13}$, $R^{14}$, and $R^{15}$ are independently chosen from ($C_1$-$C_{12}$) alkyl, —$CF_3$, —OH, or —H.

8. The prodrug according to claim 1, wherein $R^2$ is linear $C_7$-$C_{20}$ alkyl, alkenyl, or alkynyl.

9. The prodrug according to claim 1, wherein $R^3$ is cyclopropyl, $R^2$ is —$CH_2$ ($CH_2$)$_{12}$$CH_2$—, X is $SO_2$, and $R^1$ is -$CH_2$ ($CH_2$)$_2$$CH_2$—.

10. The compound of claim 1, wherein the therapeutic agent is cidofovir, and wherein said $R^1$ is a linear C3 alkyl, $R^2$ is a linear C10 alkyl, and $R^3$ is a cyclobutyl.

11. A method of treating a viral disease or viral infection in a subject comprising administering to the subject a therapeutically effective amount of the prodrug according to claim 1.

12. The method of claim 11, wherein the therapeutically effective amount is from 0.5 to 500 milligrams per kilogram per day.

13. The method of claim 11 wherein the viral infection is herpes virus, a herpes virus related disease selected from the group consisting of shingles, chicken pox, blisters or sores on the mouth or genital organs, cytomegalovirus infections after organ transplant, mononucleosis, and a cancer, Epstein-Barr virus, or cytomegalovirus.

14. The method of claim 11 wherein the step of administering is orally.

15. The method of claim 13 wherein the herpes virus related disease is shingles, chicken pox, blisters or sores on the mouth or genital organs, mononucleosis, or a cancer.

* * * * *